US012721552B2

(12) United States Patent

Bechtel et al.

(10) Patent No.: US 12,721,552 B2

(45) Date of Patent: Sep. 1, 2026

(54) BATTERY-OPERATED HANDHELD TISSUE OXIMETER

(71) Applicant: ViOptix, Inc., Newark, CA (US)

(72) Inventors: Kate LeeAnn Bechtel, Pleasant Hill, CA (US); Joseph Heanue, Oakland, CA (US); Lester John Lloyd, Orinda, CA (US); Edward Solomon, Menlo Park, CA (US)

(73) Assignee: ViOptix, Inc., Newark, CA (US)

( * ) Notice: Subject to any disclaimer, the term of this patent is extended or adjusted under 35 U.S.C. 154(b) by 218 days.

(21) Appl. No.: 18/480,437

(22) Filed: Oct. 3, 2023

(65) Prior Publication Data

US 2024/0023841 A1 Jan. 25, 2024

Related U.S. Application Data

(60) Continuation of application No. 16/667,866, filed on Oct. 29, 2019, now Pat. No. 11,771,348, which is a (Continued)

(51) Int. Cl.

*A61B 5/1455* (2006.01)

*A61B 5/00* (2006.01)

(Continued)

(52) U.S. Cl.

CPC ........ *A61B 5/14551* (2013.01); *A61B 5/0059* (2013.01); *A61B 5/0075* (2013.01); (Continued)

(58) Field of Classification Search

CPC ............................ A61B 5/1455; A61B 5/1452

See application file for complete search history.

(56) References Cited

U.S. PATENT DOCUMENTS 4,223,680 A 9/1980 Jobsis 4,286,599 A 9/1981 Hahn et al.

(Continued)

FOREIGN PATENT DOCUMENTS

JP 5261088 10/1993

JP 10216115 A 8/1998

(Continued)

OTHER PUBLICATIONS

PCT International Search Report, PCT/US2013/054585, Dec. 17, 2013.

(Continued)

*Primary Examiner* — Marjan Fardanesh

(74) *Attorney, Agent, or Firm* — Aka Chan LLP

(57) ABSTRACT

A system includes an enclosure having a processor and a memory coupled to the processor. The enclosure includes a display coupled to the processor where the display is visible from an exterior of the enclosure; and a battery within the enclosure coupled to the processor and the display. The enclosure includes a probe tip coupled to an exterior of the enclosure. The probe tip includes first, second, and third sensor openings. A first distance between the first and second sensor openings is different than a second distance between the first and third sensor openings. The enclosure includes code stored in the memory where the code is executable by the processor, and includes code to receive first data associated with the first and second sensor openings, code to receive second data associated with the first and second sensor openings, and code to perform SRS using the first and the second data.

31 Claims, 39 Drawing Sheets

Related U.S. Application Data continuation of application No. 15/220,354, filed on Jul. 26, 2016, now Pat. No. 10,456,066, which is a division of application No. 13/965,156, filed on Aug. 12, 2013, now Pat. No. 9,398,870, which is a continuation-in-part of application No. 13/887,220, filed on May 3, 2013, now Pat. No. 9,345,439, and a continuation-in-part of application No. 13/887,213, filed on May 3, 2013, now Pat. No. 9,392,978, and a continuation-in-part of application No. 13/887,152, filed on May 3, 2013, now Pat. No. 9,498,157, and a continuation-in-part of application No. 13/887,130, filed on May 3, 2013, now Pat. No. 9,186,112, and a continuation-in-part of application No. 13/887,178, filed on May 3, 2013, now Pat. No. 9,216,000.

(60) Provisional application No. 61/682,146, filed on Aug. 10, 2012, provisional application No. 61/642,399, filed on May 3, 2012, provisional application No. 61/642,389, filed on May 3, 2012, provisional application No. 61/642,393, filed on May 3, 2012, provisional application No. 61/642,395, filed on May 3, 2012.

(51) Int. Cl.

| | |
|---|---|
| ***A61B 5/145*** | (2006.01) |
| ***A61B 5/1459*** | (2006.01) |
| ***A61B 5/1495*** | (2006.01) |
| ***A61B 90/00*** | (2016.01) |
| ***A61B 90/11*** | (2016.01) |
| ***A61M 35/00*** | (2006.01) |
| *A61B 90/30* | (2016.01) |

(52) U.S. Cl.

CPC ........ *A61B 5/14546* (2013.01); *A61B 5/1455* (2013.01); *A61B 5/14552* (2013.01); *A61B 5/1459* (2013.01); *A61B 5/1495* (2013.01); *A61B 5/72* (2013.01); *A61B 5/7246* (2013.01); *A61B 5/7282* (2013.01); *A61B 5/74* (2013.01); *A61B 5/7405* (2013.01); *A61B 5/742* (2013.01); *A61B 5/7475* (2013.01); *A61B 90/11* (2016.02); *A61B 90/39* (2016.02); *A61M 35/003* (2013.01); *A61B 2090/065* (2016.02); *A61B 2090/306* (2016.02); *A61B 2090/395* (2016.02); *A61B 2560/0431* (2013.01); *A61B 2560/0475* (2013.01); *A61B 2562/0271* (2013.01); *A61B 2562/166* (2013.01)

(56) References Cited

U.S. PATENT DOCUMENTS

| | | | | |
|---|---|---|---|---|
| 5,088,493 | A | 2/1992 | Giannini et al. | |
| 5,218,962 | A | 6/1993 | Mannheimer et al. | |
| 5,517,301 | A | 5/1996 | Dave | |
| 5,517,987 | A | 5/1996 | Tsuchiya | |
| 5,551,422 | A * | 9/1996 | Simonsen ............ | A61B 5/6826 600/476 |
| 5,690,113 | A | 11/1997 | Sliwa et al. | |
| 6,056,692 | A | 5/2000 | Schwartz | |
| 6,070,093 | A | 5/2000 | Oosta et al. | |
| 6,078,833 | A | 6/2000 | Hueber | |
| 6,197,034 | B1 | 3/2001 | Gvozdic et al. | |
| 6,285,904 | B1 | 9/2001 | Weber et al. | |
| 6,453,183 | B1 | 9/2002 | Walker | |
| 6,516,209 | B2 | 2/2003 | Cheng et al. | |
| 6,549,284 | B1 | 4/2003 | Boas et al. | |
| 6,587,701 | B1 | 7/2003 | Stranc et al. | |
| 6,587,703 | B2 | 7/2003 | Cheng et al. | |
| 6,597,931 | B1 | 7/2003 | Cheng et al. | |
| 6,708,048 | B1 | 3/2004 | Chance | |
| 6,735,458 | B2 | 5/2004 | Cheng et al. | |
| 6,766,188 | B2 | 7/2004 | Soller | |
| 6,839,580 | B2 | 1/2005 | Zonios et al. | |
| 7,247,142 | B1 | 7/2007 | Elmandjra et al. | |
| 7,254,427 | B2 | 8/2007 | Cho et al. | |
| 7,344,587 | B2 | 3/2008 | Kahn et al. | |
| D567,949 | S | 4/2008 | Lash et al. | |
| 7,355,688 | B2 | 4/2008 | Lash et al. | |
| D568,479 | S | 5/2008 | Mao et al. | |
| 7,657,293 | B2 | 2/2010 | Lash et al. | |
| 8,798,700 | B1 | 8/2014 | Heaton et al. | |
| 2002/0019587 | A1 | 2/2002 | Cheng et al. | |
| 2002/0179094 | A1 | 12/2002 | Perlow | |
| 2004/0111016 | A1 | 6/2004 | Casscells et al. | |
| 2004/0260161 | A1 | 12/2004 | Melker | |
| 2005/0177069 | A1 | 8/2005 | Takizawa et al. | |
| 2005/0250998 | A1 | 11/2005 | Huiku | |
| 2005/0277818 | A1 | 12/2005 | Myers | |
| 2006/0129037 | A1 | 6/2006 | Kaufman et al. | |
| 2007/0149886 | A1 | 6/2007 | Kohls | |
| 2008/0015422 | A1 | 1/2008 | Wessel | |
| 2008/0015424 | A1 | 1/2008 | Bernreuter | |
| 2008/0139908 | A1 | 6/2008 | Kurth | |
| 2008/0181715 | A1 | 7/2008 | Cohen | |
| 2008/0275317 | A1 * | 11/2008 | Cho ......................... | A61B 5/01 600/310 |
| 2008/0319290 | A1 | 12/2008 | Mao et al. | |
| 2009/0234209 | A1 | 9/2009 | Lash et al. | |
| 2009/0275805 | A1 | 11/2009 | Lane et al. | |
| 2010/0010486 | A1 | 1/2010 | Mehta et al. | |
| 2011/0028814 | A1 | 2/2011 | Petersen et al. | |
| 2011/0046458 | A1 | 2/2011 | Pinedo et al. | |
| 2011/0205535 | A1 | 8/2011 | Soller et al. | |
| 2011/0224518 | A1 | 9/2011 | Tindi et al. | |
| 2011/0237911 | A1 | 9/2011 | Lamego et al. | |

FOREIGN PATENT DOCUMENTS

| | | |
|---|---|---|
| JP | 11244268 A | 12/1999 |
| JP | 2006109964 | 4/2006 |
| KR | 1020000075056 | 12/2000 |
| KR | 1020090016744 | 2/2009 |
| WO | 2011-008382 A1 | 1/2011 |

OTHER PUBLICATIONS

Alexandrakis, et al., "Accuracy of the Diffusion Approximation in Determining the Optical Properties of a Two-Layer Turbid Medium," Applied Optics, vol. 37, No. 31, Nov. 1, 1998, pp. 7403-7409.

Cen, et al., "Optimization of Inverse Algorithm for Estimating the Optical Properties of Biological Materials Using Spatially-Resolved Diffuse Reflectance," Inverse Problems in Science and Engineering, vol. 18, No. 6, Sep. 2010, pp. 853-872.

Dam, et al., "Determination of Tissue Optical Properties from Diffuse Reflectance Profiles by Multivariate Calibration," Applied Optics, vol. 37, No. 4, Feb. 1, 1998, pp. 772-778.

Farrell, et al., "Influence of Layered Tissue Architecture on Estimates of Tissue Optical Properties Obtained from Spatially Resolved Diffuse Reflectometry," Applied Optics, vol. 37, No. 10, Apr. 1, 1998, pp. 1958-1972.

Fawzi, et al., "Determination of the Optical Properties of a Two-Layer Tissue Model by Detecting Photons Migrating at Progressively Increasing Depths," Applied Optics, vol. 42, No. 31, Nov. 1, 2003, pp. 6398-6411.

Kienle, et al., "Spatially Resolved Absolute Diffuse Reflectance Measurements for Noninvasive Determination of the Optical Scattering and Absorption Coefficients of Biological Tissue," Applied Optics, vol. 35, No. 13, May 1, 1996, pp. 2304-2314.

Nichols, et al., "Design and Testing of a White-Light, Steady-State Diffuse Reflectance Spectrometer for Determination of Optical Properties of Highly Scattering Systems," Applied Optics, vol. 36, No. 1, Jan. 1, 1997, pp. 93-104.

(56) References Cited

OTHER PUBLICATIONS

Seo, et al., "Perturbation and Differential Monte Carlo Methods for Measurement of Optical Properties in a Layered Epithelial Tissue Model," Journal of Biomedical Optics, vol. 12(1), 014030, Jan./Feb. 2007, pp. 1-15.
Tseng, et al., "In Vivo Determination of Skin Near-Infrared Optical Properties Using Diffuse Optical Spectroscopy," Journal of Biomedical Optics, vol. 13(1), 014016, Jan./Feb. 2008, pp. 1-7.
Tseng, et al., "Analysis of a Diffusion-Model-Based Approach for Efficient Quantification of Superficial Tissue Properties," Optics Letters, vol. 35, No. 22, Nov. 15, 2010, pp. 3739-3741.
Hueber, Dennis et al., "New Optical Probe Designs for Absolute (Self-Calibrating) NIR Tissue Hemoglobin Measurements," in Proceedings of Optical Tomography and Spectroscopy of Tissue III, vol. 3597, 618-631(Jan. 1999).
Mittnacht, et al., "Methylene Blue Administration is Associated with Decreased Cerebral Oximetry Values," Anesthesia & Analgesia, Aug. 2008, vol. 105, No. 2, pp. 549-550.

* cited by examiner

BATTERY-OPERATED HANDHELD TISSUE OXIMETER

CROSS-REFERENCE TO RELATED APPLICATIONS

This patent application is a continuation of U.S. patent application Ser. No. 16/667,866, filed Oct. 29, 2019, issued as U.S. Pat. No. 11,771,348 on Oct. 3, 2023, which is a continuation of U.S. patent application Ser. No. 15/220,354, filed Jul. 26, 2016, issued as U.S. Pat. No. 10,456,066 on Oct. 29, 2019, which is a divisional of U.S. patent application Ser. No. 13/965,156, filed Aug. 12, 2013, issued as U.S. Pat. No. 9,398,870 on Jul. 26, 2016, which claims the benefit of U.S. patent application 61/682,146, filed Aug. 10, 2012. U.S. patent application Ser. No. 13/965,156 is a continuation-in-part of U.S. patent applications Ser. Nos. 13/887,130, 13/887,152, 13/887,220, 13/887,213, and 13/887,178, filed May 3, 2013, which claim the benefit of U.S. patent applications 61/642,389, 61/642,393, 61/642,395, and 61/642,399, filed May 3, 2012. These applications are incorporated by reference along with all other references cited in this application.

BACKGROUND OF THE INVENTION

The present invention relates generally to optical systems that monitor oxygen levels in tissue. More specifically, the present invention relates to optical probes, such as compact, handheld oximeters, that include sources and detectors on sensor heads of the optical probes.

Oximeters are medical devices used to measure oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions. While existing oximeters have been sufficient for post-operative tissue monitoring where absolute accuracy is not critical and trending data alone is sufficient, accuracy is, however, required during surgery in which spot-checking can be used to determine whether tissue can remain viable or needs to be removed.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated and deoxygenated hemoglobins, melanin, water, lipid, and cytochrome. Oxygenated and deoxygenated hemoglobins are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these.

Therefore, there is a need for an improved tissue oximetry devices and methods of making measurements using these devices.

BRIEF SUMMARY OF THE INVENTION

Embodiments relate to a compact, handheld, tissue oximetry device that includes light sources and light detectors. Device implementations are entirely self-contained, without any need to connect, via wires or wirelessly, to a separate system unit for making oxygen saturation measurements. The sources and detectors are arranged in a circular arrangement having various source-detector pair distances that allow for robust calibration, self-correction, and spatially-resolved spectroscopy in a compact probe. Other source-detector arrangements are also possible.

In an implementation, the device is a tissue oximeter, which can measure oxygen saturation without requiring a pulse or heart beat. A tissue oximeter of the invention is applicable to many areas of medicine and surgery including plastic surgery. The tissue oximeter can make oxygen saturation measurements of tissue where there is no pulse; such tissue, for example, may have been separated from the body (e.g., a flap) and will be transplanted to another place in the body.

According to one embodiment, a tissue oximetry system includes an enclosure that includes a first printed circuit board, housed within the enclosure. The first printed circuit board includes a processor and a memory where the memory is coupled to the processor. The enclosure includes a display, coupled to the processor where the display is visible from an exterior side of the enclosure. The enclosure includes a battery, housed within the enclosure where the battery is coupled to the processor and the display. The enclosure includes a probe tip, coupled to an exterior side of the enclosure where the probe tip includes at least a first sensor opening, a second sensor opening, and a third sensor opening. A first distance is between the first and second sensor openings, and a second distance is between the first and third sensor openings. The first distance is different from the second distance. The enclosure includes executable code, stored in the memory. The executable code is executable by the processor and includes a first code to receive first data associated with the first and second sensor openings of the first distance, a second code to receive second data associated with the first and second sensor openings of the second distance, and a third code to perform spatially-resolved spectroscopy using the first and second data.

According to a specific embodiment, the first sensor opening comprises a light source and the second and the third sensor openings comprise light detectors. In an alternative embodiment, the first sensor opening comprises a light detector and the second and the third sensor openings comprise light sources.

According to another specific embodiment, the probe tip includes a first layer comprising a second printed circuit board comprising a first light source, and includes a second layer, below the first layer. The probe tip further includes a third printed circuit board comprising a first light detector and a second light detector. A third layer of the probe tip is between the first and second layer and includes a first lens positioned below the first light source. A fourth layer of the probe tip is below the third layer and includes a waveguide positioned below the first lens. The third printed circuit board may include a first aperture positioned below the first lens. The waveguide may include an optical fiber.

According to another specific embodiment, the executable code includes a fourth code to calculate an estimated oxygen saturation value based on the first and second data; and a fifth code to cause the display to show the estimated oxygen saturation value.

According to another specific embodiment, the spatially-resolved spectroscopy is dependent on the first distance and the second distance being different.

According to another specific embodiment at least one of the first, the second, and the third sensor opening comprises a light source; and the probe tip comprises a temperature sensing unit positioned adjacent to the light source. The temperature sensor is configured to generate temperature information that represents the temperature of the light source. The processor is configured to receive the temperature information and adjust a duty cycle of an oscillating control signal supplied to the light source to adjust the luminosity generated by the light source based on the temperature information if the temperature of the light source changes.

According to another specific embodiment, the probe tip is rigidly attached to the housing and includes a pressure sensor for sensing pressure of the probe tip on tissue. The enclosure can be ten inches in length or less and can be five inches or less across any lateral axis of the enclosure.

According to another embodiment, a method includes enclosing in a housing a first printed circuit board comprising a processor and a memory, wherein the memory is coupled to the processor. The method includes providing a display, coupled to the processor and the housing, wherein the display is visible from an exterior side of the housing. The method includes enclosing a battery within the housing where the battery is coupled to the processor and the display. The method includes forming a structure of the housing to retain the probe tip. The probe tip is coupled to an exterior side of the enclosure, and the probe tip comprises at least a first sensor opening, a second sensor opening, and a third sensor opening. A first distance is between the first and second sensor openings, and a second distance is between the first and third sensor openings. The first distance is different from the second distance. The method includes configuring the probe tip to receive first data associated with the first and the second sensor openings; and configuring the probe tip to receive second data associated with the first and the third sensor openings. The method includes configuring the processor to perform spatially-resolved spectroscopy using the first and the second data to determine an oxygen saturation value.

According to a specific embodiment, the method includes providing a light source for the first sensor opening; and providing light detectors for the second and the third sensor openings comprise light detectors. According to one alternative embodiment, the method includes providing a light detector for the first sensor opening; and providing light sources for the second and the third sensor openings.

According to another specific embodiment, the method includes providing in the probe tip: a first layer comprising a second printed circuit board comprising a first light source; a second layer, below the first layer, comprising a third printed circuit board comprising a first light detector and a second light detector; a third layer, between the first and second layer, comprising a first lens positioned below the first light source; and a fourth layer, below the third layer, comprising a waveguide positioned below the first lens. The method includes forming in the third printed circuit board a first aperture positioned to be below the first lens. The waveguide may include an optical fiber.

According to another specific embodiment, the method further includes configuring the processor to calculate an estimated oxygen saturation value based on the first and second data; and configuring the processor to cause the display to the estimated oxygen saturation value. The spatially-resolved spectroscopy is dependent on the first distance and the second distance being different.

Other objects, features, and advantages of the present invention will become apparent upon consideration of the following detailed description and the accompanying drawings, in which like reference designations represent like features throughout the figures.

DETAILED DESCRIPTION OF INVENTION

Figure 1:
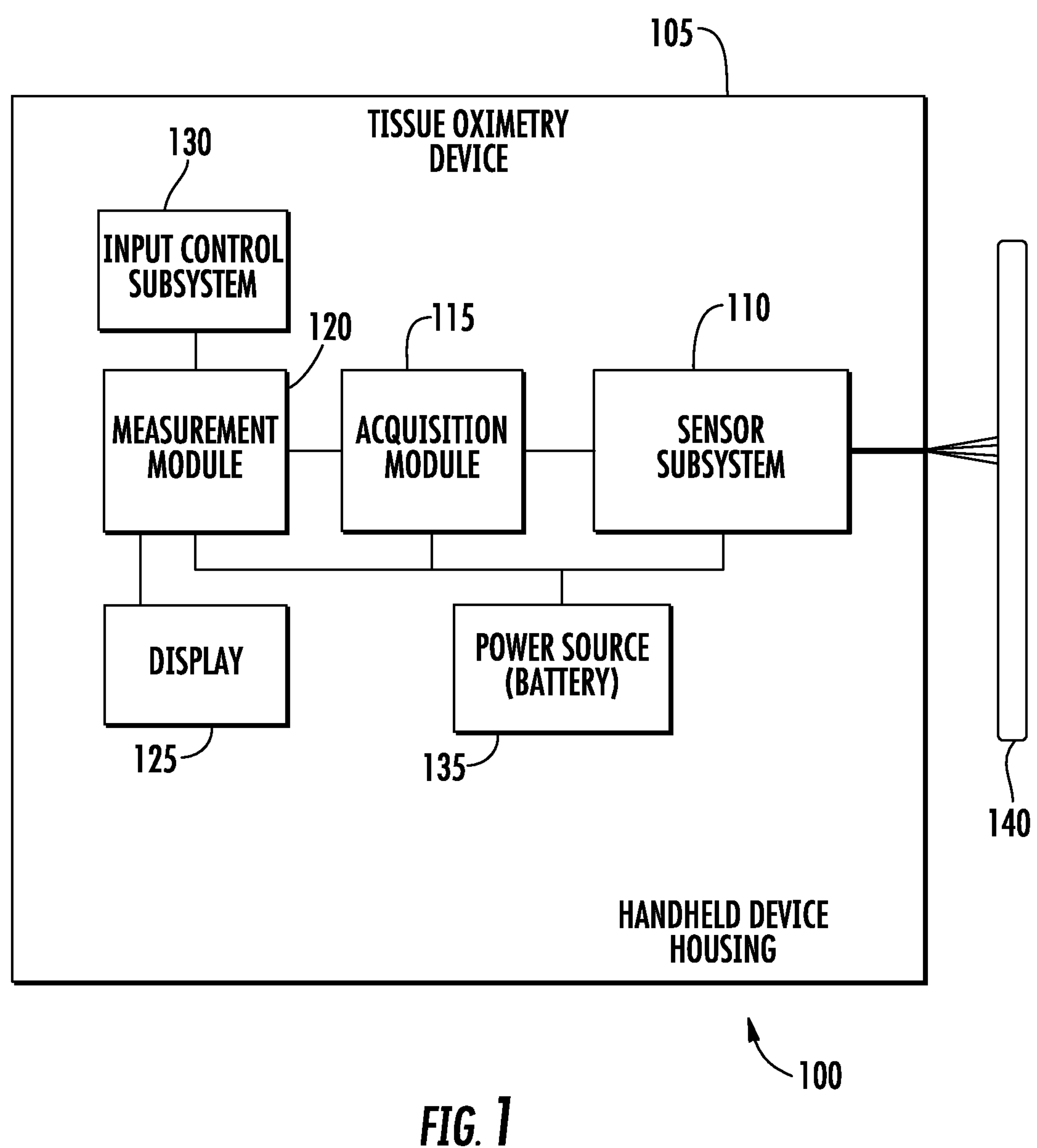
FIG. 1 is a simplified block diagram of a tissue oximetry device according to one embodiment, and shows a number of processing modules that can be included in the tissue oximetry device.

Spectroscopy has been used for noninvasive measurements of various physiological properties in animal and human subjects. Visible (e.g., red light) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy have been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficient and the reduced scattering coefficient of the physiological medium by use of the photon diffusion approximation or Monte Carlo models. From the absorption coefficients at multiple wavelengths, concentrations of oxygenated and deoxygenated hemoglobins can be determined and from these concentrations, the tissue oxygen saturation can be calculated.

CWS generally does not possess enough information to separate the effects of scattering and absorption. Accordingly, concentrations of oxygenated and deoxygenated hemoglobins cannot typically be isolated from one another. CWS has typically been used to solve a modified Beer-Lambert equation that requires assumptions about tissue scattering and two or more wavelengths are used ratiometrically to cancel out optical path length, which would otherwise be required to solve the equation. CWS, in its commonly-used form, provides relative oxygen saturation only and cannot provide absolute oxygen saturation or concentrations of oxygenated and deoxygenated hemoglobins.

Despite the capability of TRS and PMS of providing hemoglobin concentrations and absolute oxygen saturation, one major drawback of TRS and PMS equipment is that the equipment is bulky and relatively expensive. Another major drawback is that both of these techniques have difficulty measuring through relatively small volumes of tissue (i.e., "local" measurement, within a few millimeters). These techniques are typically used for "regional" measurements (minimum of 1 centimeter) due to the small time changes or phase shifts associated with short transit times through small volumes of tissue. In contrast, CWS equipment can be manufactured at a relatively lower cost, but is typically limited in its utility as described above unless enhancements are made by either including broadband spectral information or by including spatial information. While current probes based on CWS have proven sufficient for post-operative tissue monitoring where speed of measurement is less critical and relative rather than where absolute saturation measurements are of concern. However, currently available probes have been shown to give inaccurate saturation measurements when used intraoperatively due to common CWS assumptions. Embodiments of the presently described invention provide improvements in tissue oximetry over known devices.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes in index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations and therefore oxygen saturation within the volume of the tissue probed. Further, the wavelengths of the light source or light sources and the relative positions of the light source(s) with respect to the detectors, allow tissue oximetry measurements to be made for a predetermined tissue depth.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions. U.S. patent applications Ser. Nos. 13/887,130, 13/887,220, 13/887,213, 13/887,178, and 13/887,152, filed May 3, 2013, describing tissue oximetry devices that can use spatially-resolved spectroscopy, are incorporated by reference.

Tissue Oximetry Device

Embodiments of the present invention relate to tissue oximetry devices that use SRS to provide concentrations of oxygenated hemoglobin and deoxygenated hemoglobin from which the tissue oximetry devices can determine the estimated oxygen saturation. Embodiments of the tissue oximetry devices are relatively compact providing for ease of handheld use by a single user.

FIG. 1 is a simplified block diagram of a tissue oximetry device 100 according to one embodiment, and shows a number of processing modules that can be included in the tissue oximetry device. Tissue oximetry device 100 is a handheld device configured for handheld use by a single user and uses SRS for determining absolute oxygen saturation of tissue.

In an implementation, the tissue oximetry device displays an absolute oxygen saturation which is a percentage value from 0 to 100 (or 0 to 99 for a 2-digit display). In other implementations, the tissue oximetry device displays a value or other indication representation of an absolute oxygen saturation. This representative value can be another range (e.g., 0 to 20 or 0 to 50), indicator lights (e.g., LED lights), bar graph or gauge, or other indictor that is representative of the absolute oxygen saturation. The scale of this alternative display of the absolute oxygen saturation can be linear, geometric, logarithmic, or other scale.

Further, in other implementations, the tissue oximetry device displays an estimated oxygen saturation of tissue. This estimated value can be the absolute oxygen saturation discussed above, or other estimate of the oxygen saturation. This estimated oxygen saturation can be an intermediate value, that is determined using the circuitry and techniques described in this application, and the absolute oxygen saturation is calculated or generated from this estimated oxygen saturation value. Then the device calculates the estimated oxygen saturation value (not displayed) and the absolute oxygen saturation (displayed). And alternatively, an estimated oxygen saturation value can be determined from the absolute oxygen saturation.

According to the embodiment shown in FIG. 1, tissue oximetry device 100 includes a handheld device housing 105 (bold surrounding line in FIG. 1), a sensor subsystem 110, and acquisition module 115, a measurement module 120 (sometimes also referred to as a computation module), a display 125 (e.g., an optionally backlit liquid crystal display screen), one or more input controls 130, and a power source 135. Handheld device housing 105 ("housing") is configured to house one or more of the above listed elements. Specific example embodiments of housing 105 are described below.

Sensor subsystem 110 and acquisition module 115 can be communicatively coupled via a bus system, and acquisition module 115 and measurement module 120 may also be communicatively coupled via a bus system. Power source 135 can be configured to provide DC power, modulated power, or both to sensor subsystem 110, acquisition module 115, and measurement module 120.

Sensor subsystem 110 includes various optical elements for generating and emitting light or radiation (visible, infrared, or both) into tissue 140, and collecting light scattered or reflected back from the tissue into the sensor subsystem. Sensor subsystem 110 may generate reflectance data from the scattered light detected by the sensor subsystem and transmit the reflectance data to acquisition module 115 for preprocessing. Measurement module 120 can be configured to receive the preprocessed reflectance data from acquisition module 115 to determine the oxygen saturation for the tissue. Measurement module 120 can be communicatively coupled to one or more of input controllers 130 and to display 125. Based on user input received from one of the input controllers 130, tissue oximetry module 100 may determine the oxygen saturation for the tissue, and display a result for the oxygen saturation on display 125.

Figure 2:
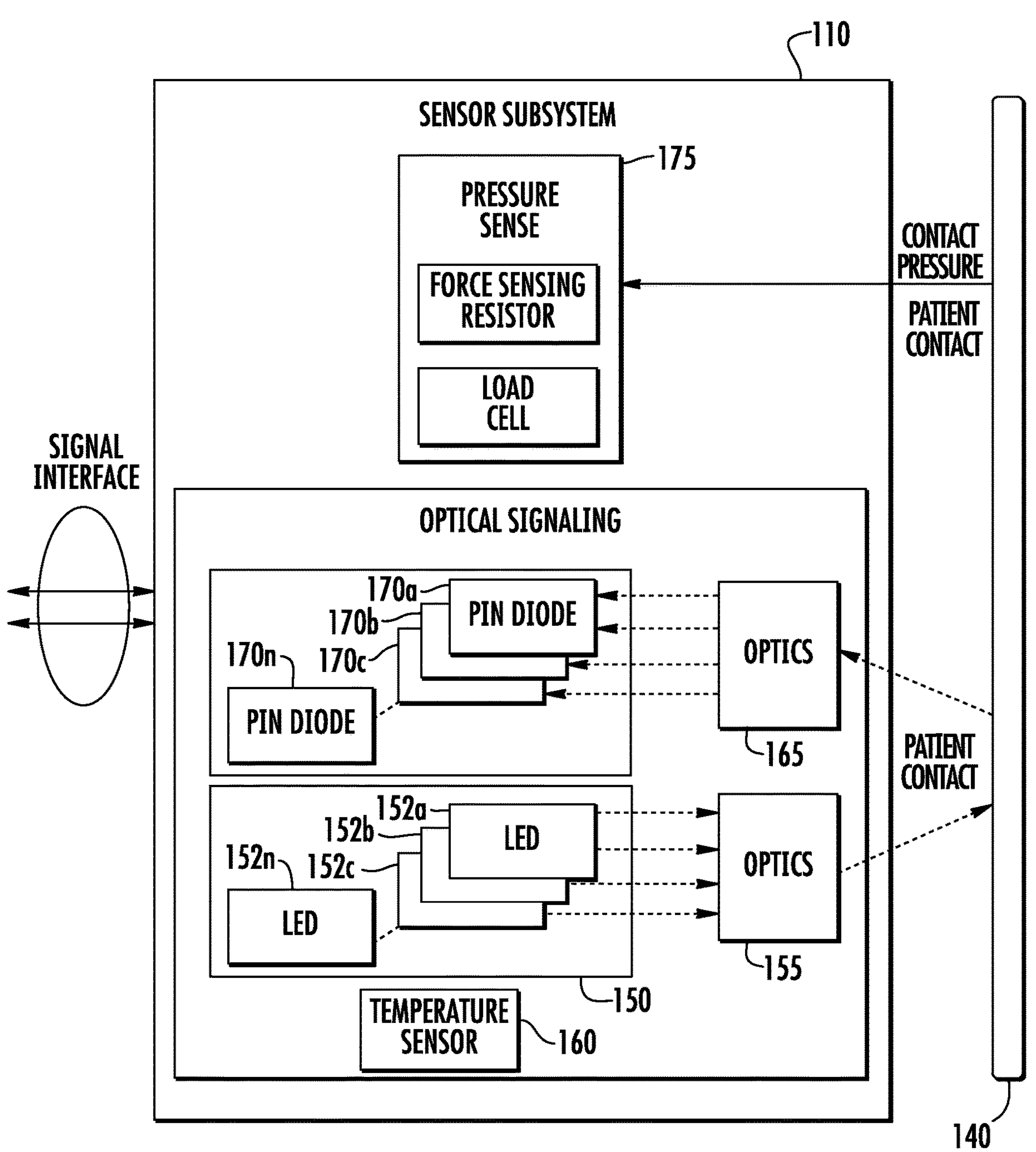
FIG. 2 is a simplified block diagram of a sensor subsystem of the tissue oximetry device according to one embodiment.

Sensor subsystem 110 is currently further described. FIG. 2 is a simplified block diagram of sensor subsystem 110 according to one embodiment. Sensor subsystem 110 may include one or more of light sources 150 (e.g., two light sources) where each light sources includes one or more of lighting elements 152*a*-152*n* (referred to collectively as lighting elements 152), such as one or more light emitting diodes (LEDs), one or more laser diodes, or the like. Sensor subsystem 110 may additionally include a first set of optical devices 155 (e.g., classical optical devices, such as lenses, fiber optic cables, or the like) that collects emitted light from each light source 150 and directs the emitted light onto tissue 140.

Sensor system 110 may also include one or more temperature sensors 160, such as one or more thermistors, configured to detected the temperature of light sources 150. In one embodiment, temperature sensors 160 are respectively associated with light sources 150 and are configured to measure the temperature of the light sources.

Temperature sensors 160 may transmit temperature information for light sources 150 to one or more of sensor subsystem 110, acquisition module 115, measurement module 120, which may use the temperature information regulate a control signal (e.g., a time varying control signal) supplied to the light sources where the control signal controls the luminosity of the light sources. For example, as the LEDs of one of the light sources heat up and cool down, the efficiency of the LEDs changes and hence the luminosity of the LEDs may change.

Sensor subsystem 110, acquisition module 115, or measurement module 120, or a combination of these elements, may change the control signal supplied to the LEDs so that the LEDs provide a substantially constant luminosity. For example, if a control signal, such as a sine wave shaped control signal, is supplied to the LEDs, sensor subsystem 110, acquisition module 115, or measurement module 120, or a combination of these elements, may alter a duty signal of the control signal so that the LEDs provide a substantially constant luminosity as the LEDs heat up or cool down.

In an alternative embodiment, a photodetector can be positioned in sensor subsystem 110, such as in a probe tip (described below), for detecting increases, decreases, and no change in the luminosity of the light sources. One or more of sensor subsystem 110, acquisition module 115, and measurement module 120 can be communicatively connected to the photo detector for receiving photodetector information, where the photodetector information includes information for the increase, decrease, or lack of change (e.g., no change). One or more of sensor subsystem 110, acquisition module 115, and measurement module 120 may use the received photodetector information for controlling the light sources so that the light sources generate substantially constant or uniform luminosity.

In a specific implementation, the luminosity emitted by lighting elements 152 can be changed by sensor subsystem 110, acquisition module 115, measurement module 120, or a combination of these if the temperature of lighting elements 152 changes by a threshold amount between two successive measurements of the temperature made by temperatures sensors 160. Specifically, if the temperature change is at the threshold or within the threshold, the luminosity of the lighting elements might not be changed (e.g., the duty signal of the time varying control signal is held constant). Alternatively, if the temperature change is greater than the threshold, then the luminosity of the lighting elements can be changed (e.g., the duty cycle of the time varying control signal can be raised or lowered or otherwise altered, accordingly) to maintain a substantially constant luminosity.

Sensor subsystem 110 may further include a second set of optical device 165 that collects the light reflected from tissue 140 and directs this light to one or more light detectors 170*a*-170*n* (referred to collectively as light detectors 170), such one or more of PIN diodes, one or more photoresistors, or the like. Each light detector 170 may generate reflection data based on detected light, which can be used by acquisition module 115, measurement module 115, or both for generating an oxygen saturation measurement for tissue 140. Further details of the spatial distribution of lighting sources 150 and light detectors 170 are described below where the spatial distribution allows for SRS to be performed by tissue oximetry device 100.

Sensor subsystem 110 may also include a pressure sensor 175 that is configured to detect a pressure of a sensor head of the sensor subsystem against tissue 140. Pressure sensor 175 may include one or more of a force sensing resistor, a load cell, or the like. Pressure sensor 175 is mentioned briefly here, and is described further below. It is noted that select embodiments of tissue oximetry device 100 include pressure sensor 175, while other embodiments of the tissue oximetry device might not include the pressure sensor.

Figure 3:
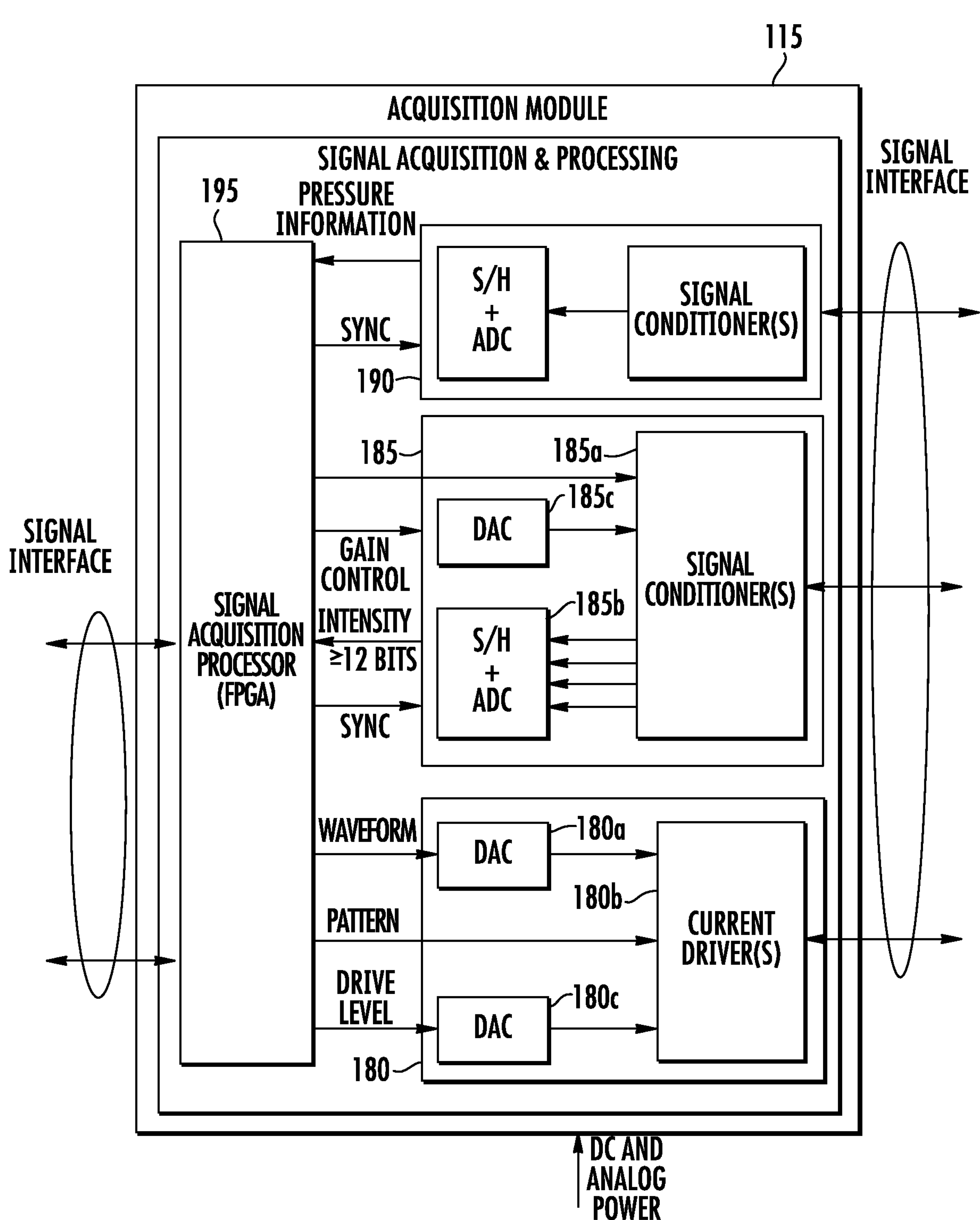
FIG. 3 is a simplified block diagram of the acquisition module of the tissue oximetry device according to one embodiment.

Acquisition module 115 is currently further described. FIG. 3 is a simplified block diagram of the acquisition module according to one embodiment. Acquisition module 115 may include a drive circuit 180, a reflectance data collector 185, a pressure data collector 190, and a signal acquisition processor 195. Various embodiments of acquisition subsystem 115 may include some or all of these elements in any combination. Via signal acquisition processor 195, drive circuit 180, or both, acquisition module 115 may provide the varying control signal to light sources 150 for controlling the light emitted therefrom. For example, signal acquisition processor 195 may supply a waveform, such as a digital waveform to drive circuit 180. The digital waveform can be a digital form of the time varying control signal (e.g., sine wave shaped control signal) described above.

A digital-to-analog converter (DAC) 180*a* of drive circuit 180 receives the digital waveform and convert the digital waveform to an analog form of the control signal (i.e., analog sine wave control signal) and supplies or outputs the analog form of the control signal to a current driver 180*b*. Signal acquisition processor 195 also supplies or outputs a predefined current pattern and a digital drive level to the drive circuit 180. Current driver 180*b* receives the current pattern substantially directly from signal acquisition process 195 and receives an analog form of the drive level from a second DAC 180*c* of drive circuit 180. Current driver 180 can use the analog form of the control signal, the pattern, and the drive level to supply the control signal to light source 150 where the current drive may use the pattern and the drive level to condition the control signal prior to transfer to sensor subsystem 105.

Signal acquisition processor 195, measurement module 120, or both can be configured to receive temperature information from temperature sensor 160 and adjust one or more of the control signal, the pattern, and the drive level to increase or decrease the duty cycle of the control signal, based on the temperature as described above. More specifically, signal acquisition processor 195 can be configured to receive the temperature information from a thermistor or the like (included in temperature sensor 160) for controlling the above described adjustments. Sensor subsystem 110 may include a temperature-information conditioning module (not shown) that can be configured to receive the temperature information (e.g., an analog signal) and condition the temperature information for use by signal acquisition processor 195, measurement module 120, or both. The temperature-information conditioning module can filter the analog signal for the temperature information, convert the temperature information to digital, or perform other operations thereon to make the temperature information useable by one or both of signal acquisition processor 195 and measurement module 120.

Turning now to reflectance data collector 185, the reflectance data collector can be configured to receive raw reflectance data generated by light detectors 170 and process the raw reflectance data. More specifically, reflectance data collector 185 can be configured to receive, accumulate, filter, digitize, and average raw reflectance data, which may thereafter be converted into corresponding physical quantities, such as light intensity. Reflectance data collector 185 may include a signal conditioner 185*a* that receives the raw reflectance data and may filter the raw reflectance data as necessary. An analog to digital converter (ADC) 185*b*, with a sample and hold circuit, may convert the raw reflectance data to a digital signal, which can be averaged and correlated with the light emitted from the sources by signal acquisition processor 195 for further processing may measurement module 120.

Correlation may include correlating calibration information for each light detector 170 with each lighting elements 152. That is, calibration information used by tissue oximetry device 100 may include calibration information for each light detector calibrated to each light source. The luminosity of each light source, the gain of each light detector, or both can be adjusted based on the calibration information. Alternatively, reflectance data generated by each light detector can be adjusted based on the calibration information by acquisition module 115 (e.g., signal acquisition processor 195), measurement module 120, or both. Generation of the calibration information is described further below.

Signal acquisition processor 195 can also be configured to control the gain of light detectors 170 (e.g., pin diodes) via issuance of a gain control signal to acquisition module 115, which may convert the gain control signal from a digital signal to an analog signal via a DAC 85*c*, which in-turn provides the gain control signal to signal conditioner 185*a* for further transmission to one or more light detectors 170. Signal acquisition processor 195 may include one or more logic control circuits, such as a field programmable gate array (FPGA), a programmable logic device (PLD), gate array, application specific integrated circuit (ASIC), a processor, or the like for performing the above-described processes.

Figure 4:
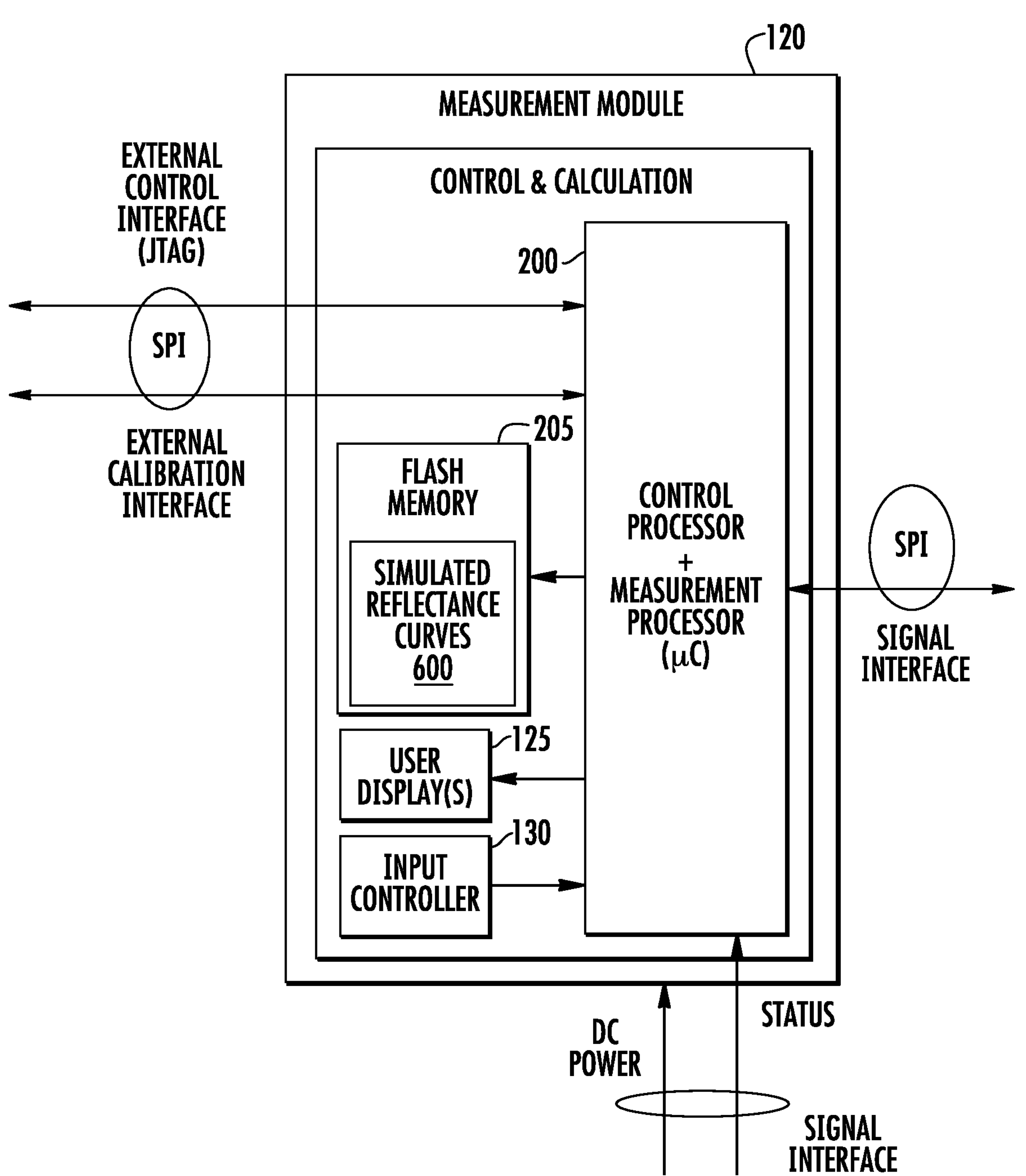
FIG. 4 is a simplified block diagram of the measurement module of the tissue oximetry device according to one embodiment.

Measurement module 120 is currently further described. FIG. 4 is a simplified block diagram of measurement module 120 according to one embodiment. Measurement module 120 may include a control processor 200, such as a microcontroller, a microprocessor, control logic, or the like, or any combination of these circuit elements. Measurement module 120 may also include a memory device 205. Memory device 205 may include one or more of a variety of memory types, such as a disk (e.g., a micro disk drive), Flash, or the like, where the memory device can be configured to store computer code instructions, data (e.g., calibration information), or both. The stored computer code instructions, data, or both can be used by control processor 200, signal acquisition processor 195, or both for performing one or more of the methods and calculations described herein, such the various methods for determining the oxygen saturation for tissue 140 from collected light. Determination of the oxygen saturation is described in further detail below in the section of the application titled Monte Carlo Simulation.

After an oxygen saturation value for the oxygen saturation is calculated, for example, as an indexed value of a percentage of total possible oxygen saturation of tissue 140 or as normalized value, the oxygen saturation value can be displayed on display 125. Determination and display of the oxygen saturation value can be a repeating process. For example, oxygen saturation of tissue 140 can be determined a number of times per second, such as three times per second. Two or more measurements, such as three measurements, of the oxygen saturation value can be averaged by control processor 200 for display on display 125. For example, three measurements of the oxygen saturation can be made in one second and can be averaged.

This average oxygen saturation value may then displayed on display 125 and the displayed oxygen saturation value can be updated on the display once per second (e.g., at one hertz). Generally, averaging oxygen saturation measurements over relatively long periods is not performed so that oxygen saturation measurements are not averaged for different locations on tissue 140. For example, if a user moves tissue oximetry device 100 from one location on the tissue to another location on the tissue, which often takes a second or longer, an average of the oxygen saturation values for these different locations should generally not be displayed on the display. Generally limiting the averaging to oxygen saturation values to a one second time frame limits the averaging of oxygen saturation values for more than one tissue location.

Figure 5:
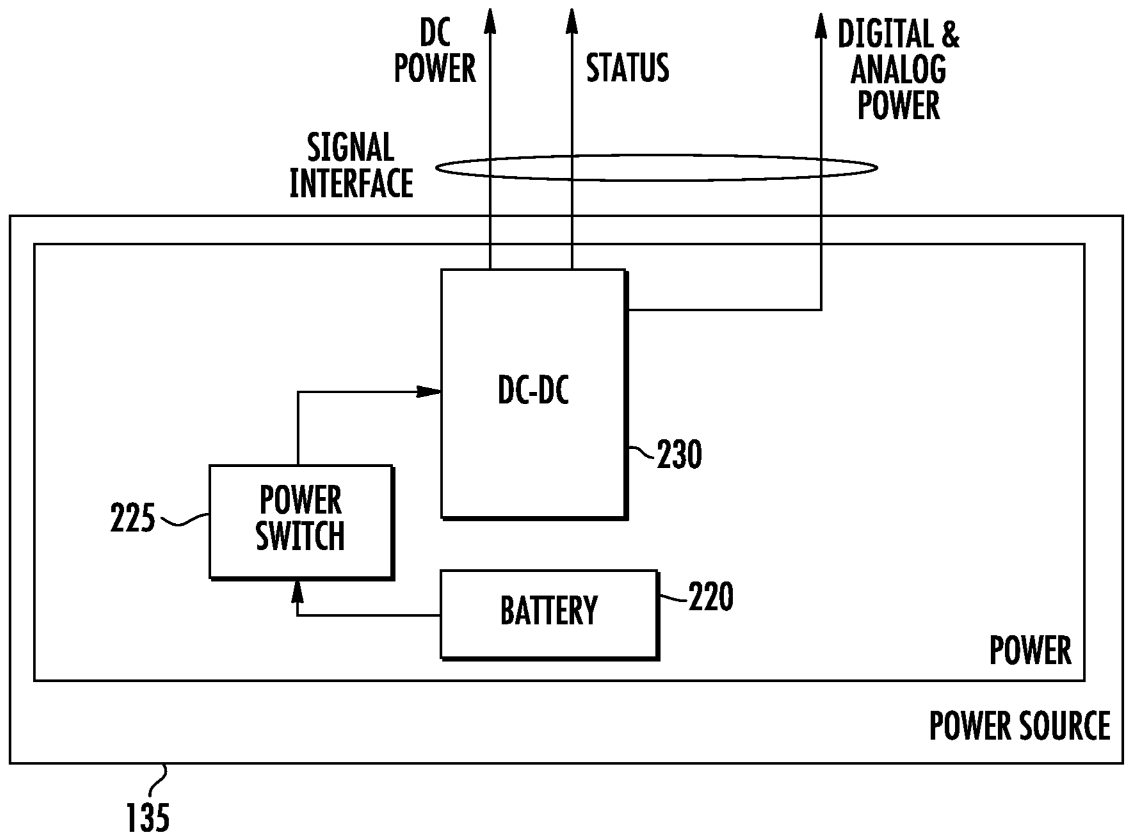
FIG. 5 is a simplified block diagram of the power source of the tissue oximetry device according to one embodiment.

Power source 135 is currently further described. FIG. 5 is a simplified block diagram of power source 135 according to one embodiment. Power source 135 may include one or more batteries 220, a power switch 225, a power convertor 230, or the like. Power source 135 may supply DC power, modulated power, or both to one or more of sensor subsystem 110, acquisition module 115, measurement module 120, display 125, and input controllers 130. Power source 135 may also be communicative coupled to measurement module 120 where the measurement module may control the power module to supply power for various power operation modes of tissue oximetry device 100, such as power up operations, standby mode, and the like.

Battery 220 can be a disposable battery or a rechargeable battery. As is known in the art, disposable batteries are discarded after their stored charge is expended. Some disposable battery chemistry technologies that can be used in power source 135 include alkaline, zinc carbon, lithium air, zinc air, or silver oxide. The batteries may include four 1.5-volt batteries (e.g., AAA, AA, or N size batteries) or two 3-volt batteries (e.g., CR2032, CR2016, CR123A, and others) that are electrically in series so that power source 135 may provide up to 6 volts to the various components of tissue oximetry device 100.

The batteries have sufficient stored charge to provide for use of tissue oximetry device 100 for several hours. For example, the batteries can be configured to provide two or more hours of use of tissue oximetry device 100. After use, the tissue oximetry device 100 or a disposable portion thereof can be discarded. In other implementations, the batteries are rechargeable and can be recharged multiple times after the stored charge is expended. Some rechargeable battery chemistry technologies that can be used in power source 135 include nickel cadmium (NiCd), nickel metal hydride (NiMH), lithium ion (Li-ion), and zinc air. The batteries can be recharged, for example, via an AC adapter with a cord that connects to the tissue oximetry device. The circuitry in the tissue oximetry device can include a recharge circuit (not shown) for battery recharge. Batteries with rechargeable battery chemistry may sometimes be used as disposable batteries, where the batteries are not recharged but are disposed of after use. Tissue oximetry device 100 can use rechargeable batteries if the tissue oximetry device or a portion thereof is configured for reuse.

Power switch 225 of power source 135 can be a user operable switch that can be configured to operate with measurement module 120 for power up, power down, entering a standby power mode of operation, coming out of the standby power mode of operation, and other functions. For example, if tissue oximetry device 100 is powered down, an activation of power switch 225 may cause tissue oximetry device 100 to execute a power up sequence under control of measurement module 120. If tissue oximetry device 100 is powered on, a relatively short activation (e.g., less than two seconds) of power switch 225 may the place tissue oximetry device into the standby power mode for saving battery power. If tissue oximetry device 100 is in the standby power mode, a subsequent relatively short activation (e.g., less that two seconds) of power switch 225 may place tissue oximetry device in full power mode relatively quickly. If tissue oximetry device 100 is in full power mode or in standby power mode, a relatively long activation (e.g., two second or longer) of power switch 225 may cause tissue oximetry device to power down.

Measurement module 120 may also cause tissue oximetry device 100 to enter the standby power mode or power down if one or more criteria are met, such as the tissue oximetry device not having been active for one or more given periods of time. For example, measurement module 120 may put tissue oximetry device 100 into the standby power mode if the tissue oximetry device is not active for 20 seconds and may put the tissue oximetry device in power down mode if the tissue oximetry device is not active for 5 minutes.

After power up, tissue oximetry device may perform a variety of self checks, such as calibrating the pressure of the pressure sensor, clearing error messages that can reside in one or more of sensor subsystem 110, acquisition module 115, measurement module 120, and power source 135.

Power converter 230 of power source 135 can be a DC-to-DC converter configured to convert the voltage output from battery 220 to a variety of DC voltages that are used by sensor subsystem 110, acquisition module 115, measurement module 120, display 125, and input controls 130. For example, power converter 230 can be configured to output 1.2 volts, 2.5 volts, 3.3 volts, 5 volts, 6 volts, or the like. Power converter 230 can be configured to output one or more of these voltages at a given time.

For some embodiments, sensor subsystem 110, acquisition module 115, measurement module 120, display 125, input controls 130, and power source 135 are sometimes referred to as self-contained electronic components in that these electronic components may make a tissue oximetry measurement and provide information for oxygen saturation of tissue without the need to communicate (wired or wirelessly) with other devices (e.g., devices external to the tissue oximetry device's housing). As such, some of the embodiments of tissue oximetry device 100 are referred to as being self-contained.

Figure 6:
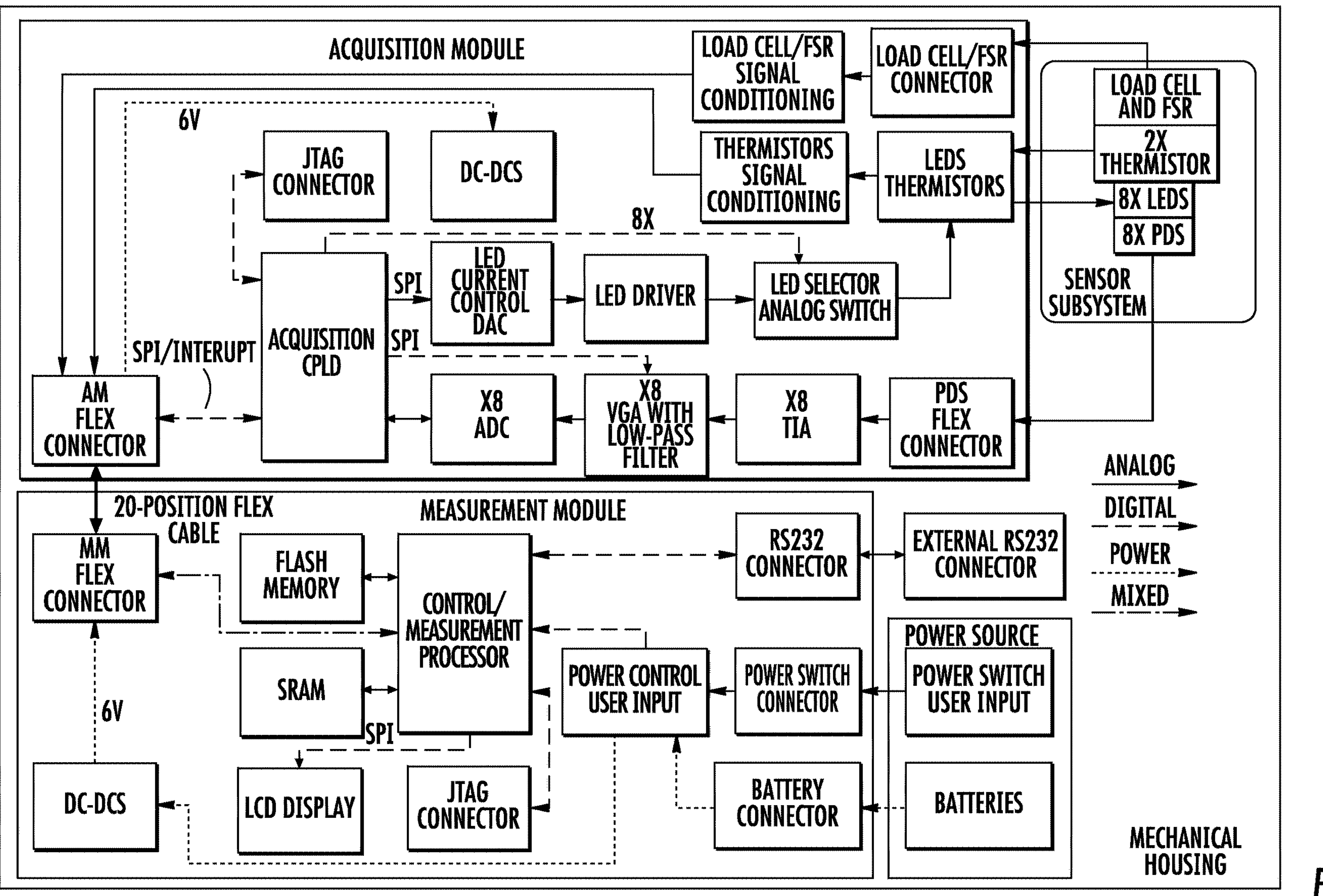
FIG. 6 is a simplified block diagram of the sensor subsystem, the acquisition module, the measurement module, and the power source and shows flows of information and power through and between these elements.

FIG. 6 is a simplified block diagram of sensor subsystem 110, acquisition module 115, measurement module 120, and power source 135 and shows flows of information and power through and between these elements. The solid lines between the functional and circuit blocks indicate the flow of analog signals. The dashed lines with the relatively long dash indicate the flow of digital signals. The dashed lines with the relatively short dash indicate the flow of power. The mixed dashed-dotted line indicates the flow of mixed signals.

Figure 7A:
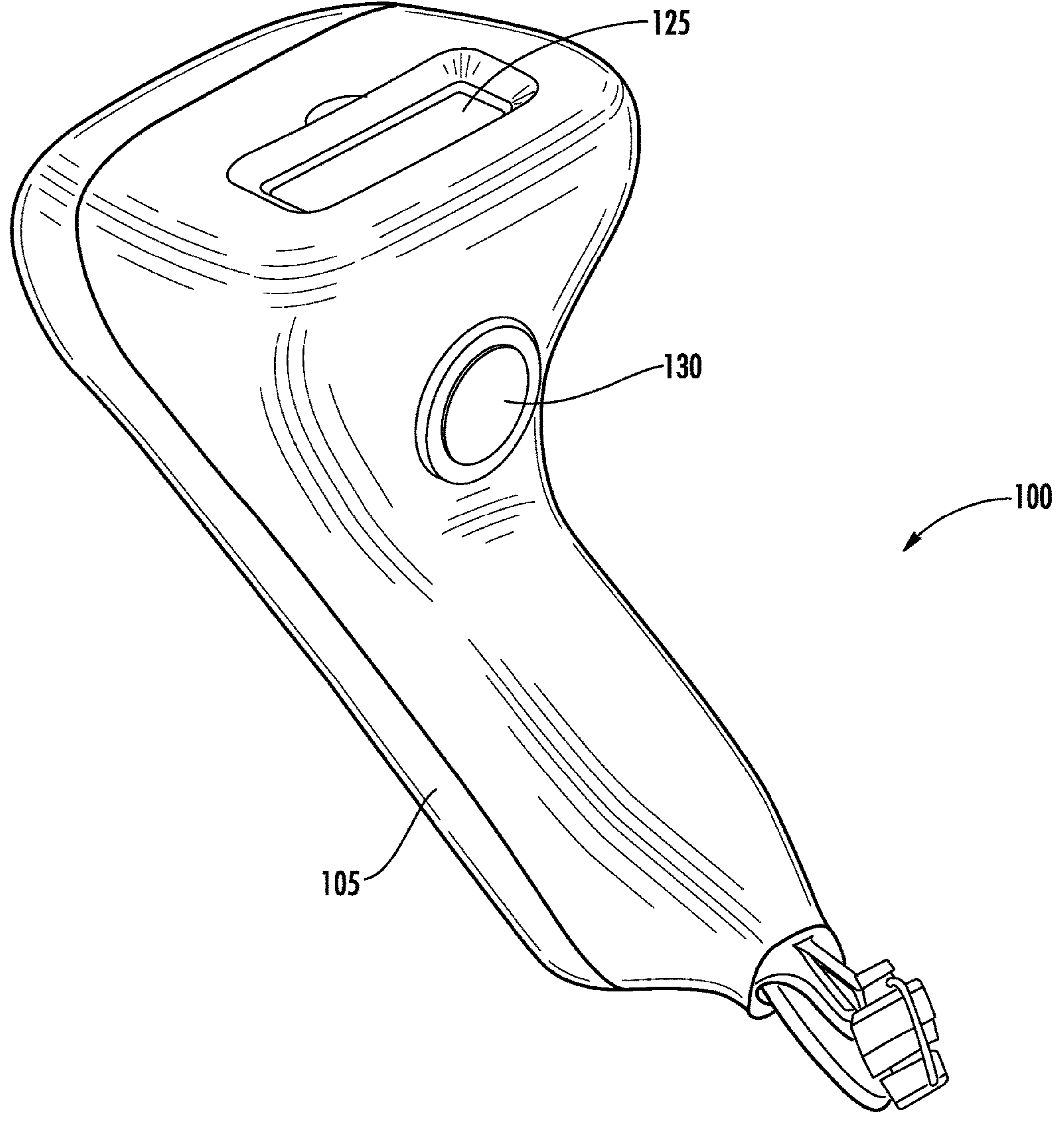
FIGS. 7A and 7B are two overall perspective views of the tissue oximetry device according to one embodiment.
Figure 7B:
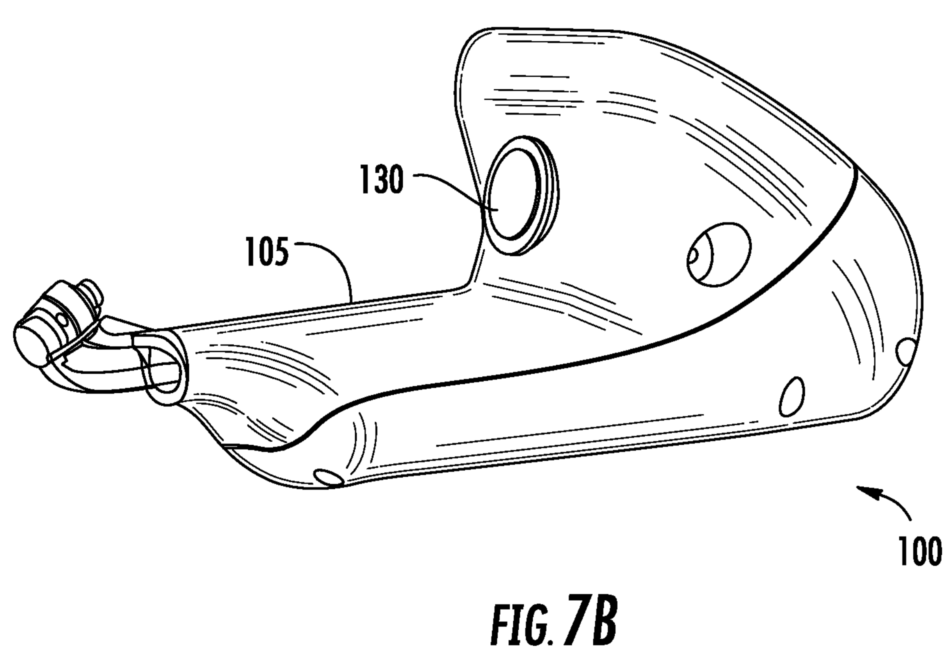
Figure 7C:
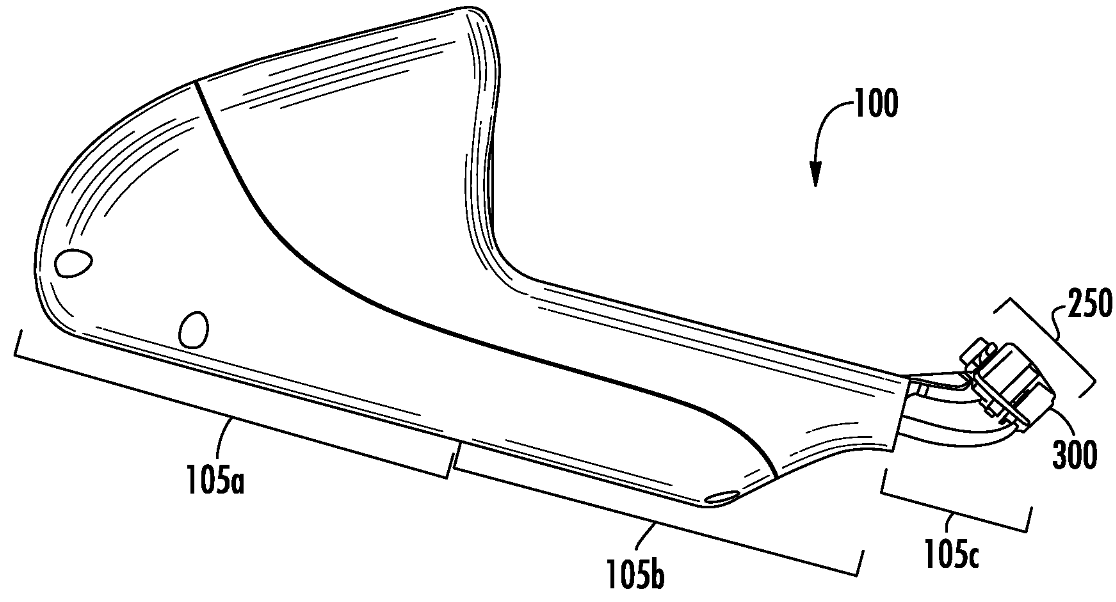
FIG. 7C is a side view of the tissue oximetry device.
Figure 7D:
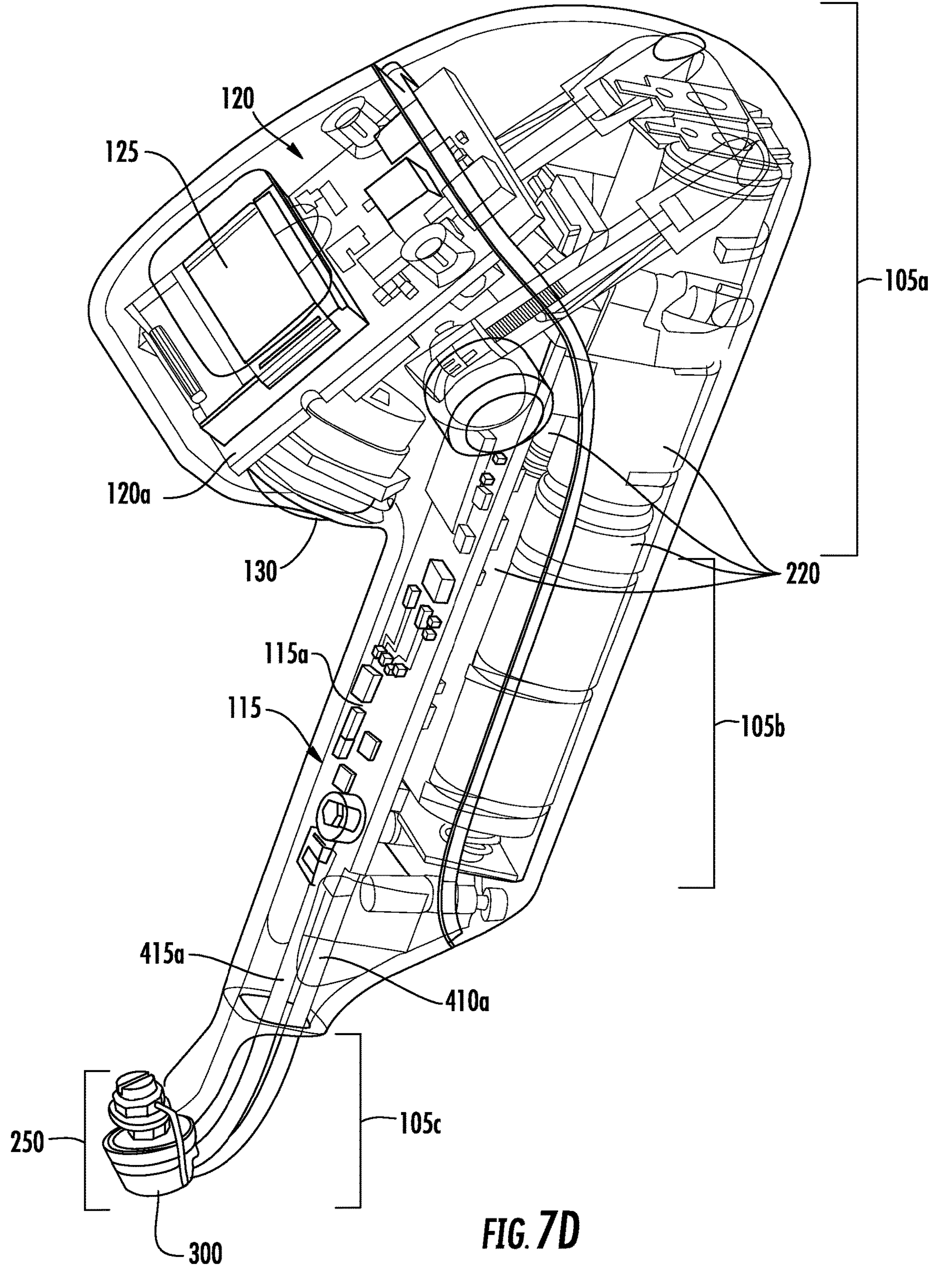
FIG. 7D is a view of the tissue oximetry device where the housing is shown as substantially transparent and where various elements positioned in the housing are shown.

FIGS. 7A and 7B are two overall perspective views of tissue oximetry device 100 according to one embodiment. FIG. 7C is a side view of tissue oximetry device 100, and FIG. 7D is a view of tissue oximetry device 100 where housing 105 is shown as substantially transparent. In the transparent view of housing 105 in FIG. 7D, the positions of elements in the housing are shown according to one embodiment.

In the particular embodiment of tissue oximetry device 100 shown in FIGS. 7A-7D, housing 105 includes a top portion 105*a* that includes display 125. Housing 105 also includes a body portion 105*b* and a tip portion 105*c*, which forms a portion of a sensor head 250. Top portion 105*a* of housing 105 is configured to be positioned upward with a user holding body portion 105*b* in their hand and with sensor head 250 pressed against the tissue of a patient. Top portion 105*a* may orient display 125 to face toward a user's face while the user holds body portion 105*b* with sensor head 250 held against the tissue.

Housing 105 can be relatively compact, for example housing may about 25 centimeters or less in length from top portion 105*a* to sensor head 250, can be less than 13 centimeters wide across any lateral axis. Housing 105 can be formed from a variety of materials, such as plastic, nylon, metal, or a combination of these. Housing 105 may conform to the requirements of UL/IEC/CAN 60601-1 and related documents for fluid spill resistance. Tip portion 105*c* can be submersible to a level sufficient for liquid phantom calibration.

At least one of the input controls 130 can be positioned on housing 105 on an underside of top portion 105*a*, and can be a button. The at least one input control on the underside of top portion 105*a* can be a power button configured for powering on, powering off, standby power mode entry, and standby power mode exit (describe above).

In the specific embodiment of tissue oximetry device 100 shown in FIG. 7D, acquisition module 115 includes a printed circuit board 115*a* with a number of circuits disposed thereon, such as the circuits of the acquisition module described above. Acquisition module 115 can be positioned substantially in body portion 105*b* of housing 105, such as along a front side of body portion 105*b*. As further shown in the embodiment of tissue oximetry device 100 in FIG. 7D, measurement module 120 includes a printed circuit board 120*a* with a number of circuits disposed thereon, such as the circuits of the measurement module described above. Measurement module 120 can be positioned substantially in top portion 105*a* of housing 105, such as along an underside of display 125. Acquisition module 115 and measurement module 120 can be fastened to housing 105 via a variety of fasteners, such as screws, nuts, and bolts, or the like, or via a variety of adhesives, such as epoxy, super glue, plastic weld, or the like. It is noted that while acquisition module 115 and measurement module 120 are shown as being in body portion 105*b* and top portion 105*a*, respectively, the locations of the acquisition module and the measurement module can be switched in housing 105, may both be in the body section or may both be in the top portion. Batteries 220 can be positioned in housing 105 along a backside of the housing and may extend from top portion 105*a* to body portion 105*b*.

According to a specific embodiment, tip portion 105*c* of housing 105 can be configured as an arm that rigidly extends from body portion 105*b* to rigidly hold sensor head 250 and a probe tip 300 relatively fixed with respect to housing 105 during use. In other embodiment, probe tip 300 may be flex coupled to housing 105 or housing 105 may include a flexible member that provide flex for probe tip 300 when the probe tip is place in contact with tissue. For example, body portion 105*b* may be configured as a flexile arm or may include one or more spring type devices that allows probe tip 300 and sensor head 250 to provide flex for the probe tip. Sensor head 250 or probe tip 300 can also include various spring type devices to provide for such flex or spring type quality.

In an implementation, a sensor head can be flexibly coupled via a spring having a spring constant (e.g., operating according to Hooke's Law). The flexible member coupling the sensor head to the enclosure can be deformed elastically, so that it returns to its original form after being deformed. This flexible sensor head can help prevent a user from exerting too much pressure against tissue which the user is attempting to measure.

In some embodiments tip portion 105*c*, portions of body portion 105*b*, sensor head 250, probe tip 300, or a combination of these can be detachable from tissue oximetry device 100 and can be replaceable. For example, tip portion 105*c* and sensor head 250 can be configured for use with a single patient and can be detached from tissue oximetry device 100 after use with the patient. Thereafter, the tip portion and the sensor head can be replaced with a new sterile tip portion 105*c* and a new sterile sensor head 250 for use with a different patient. The remaining body portion 105*b*, top portion 105*a*, and the electronic devices contained therein can be configured to be reused with different patients after tip portion 105*c* and sensor head 250, for example, are replaced.

Figure 7E:
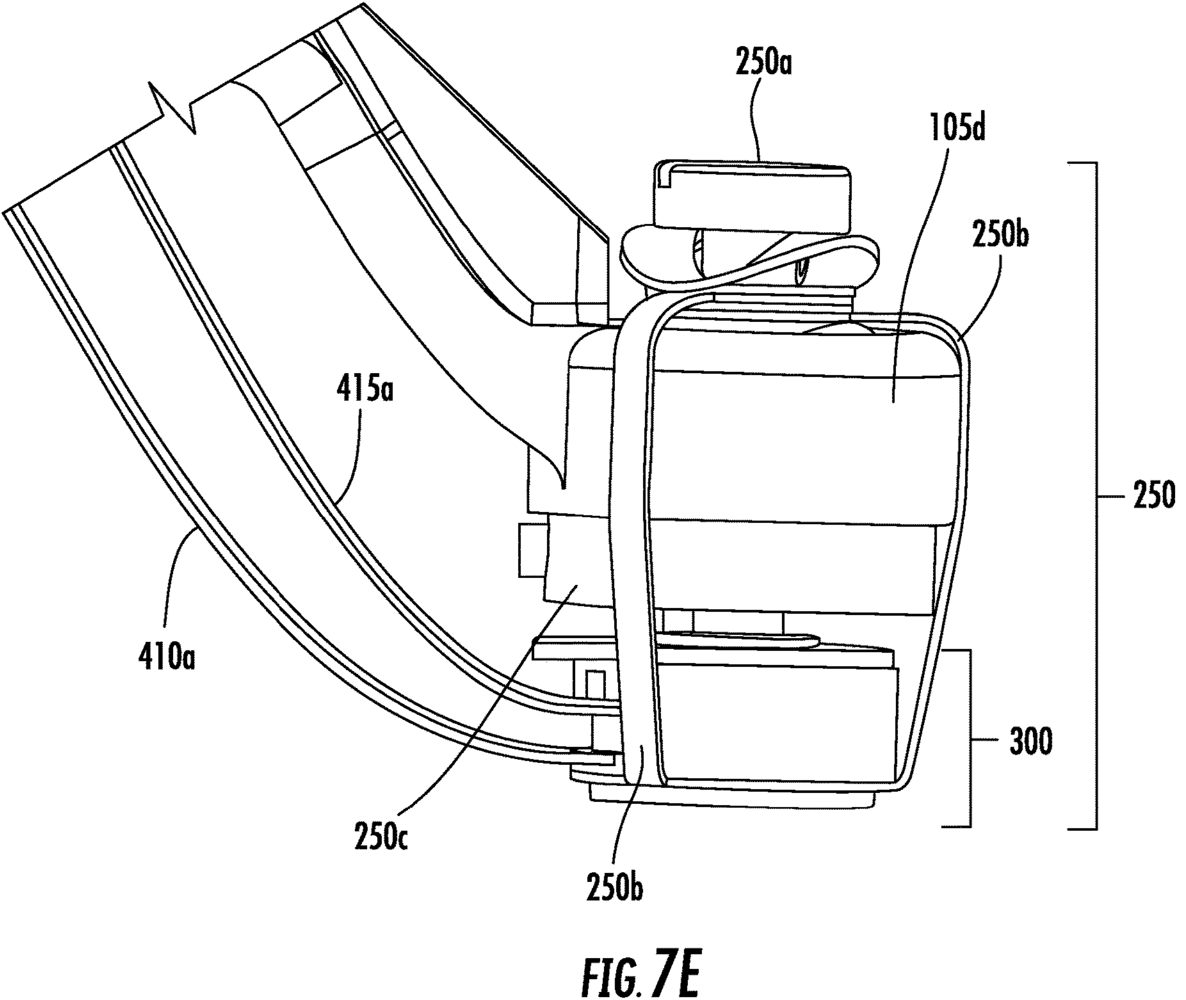
FIGS. 7E, 7F, and 7G are further enlarged views of the tip portion of the housing and the sensor head.
Figure 7F:
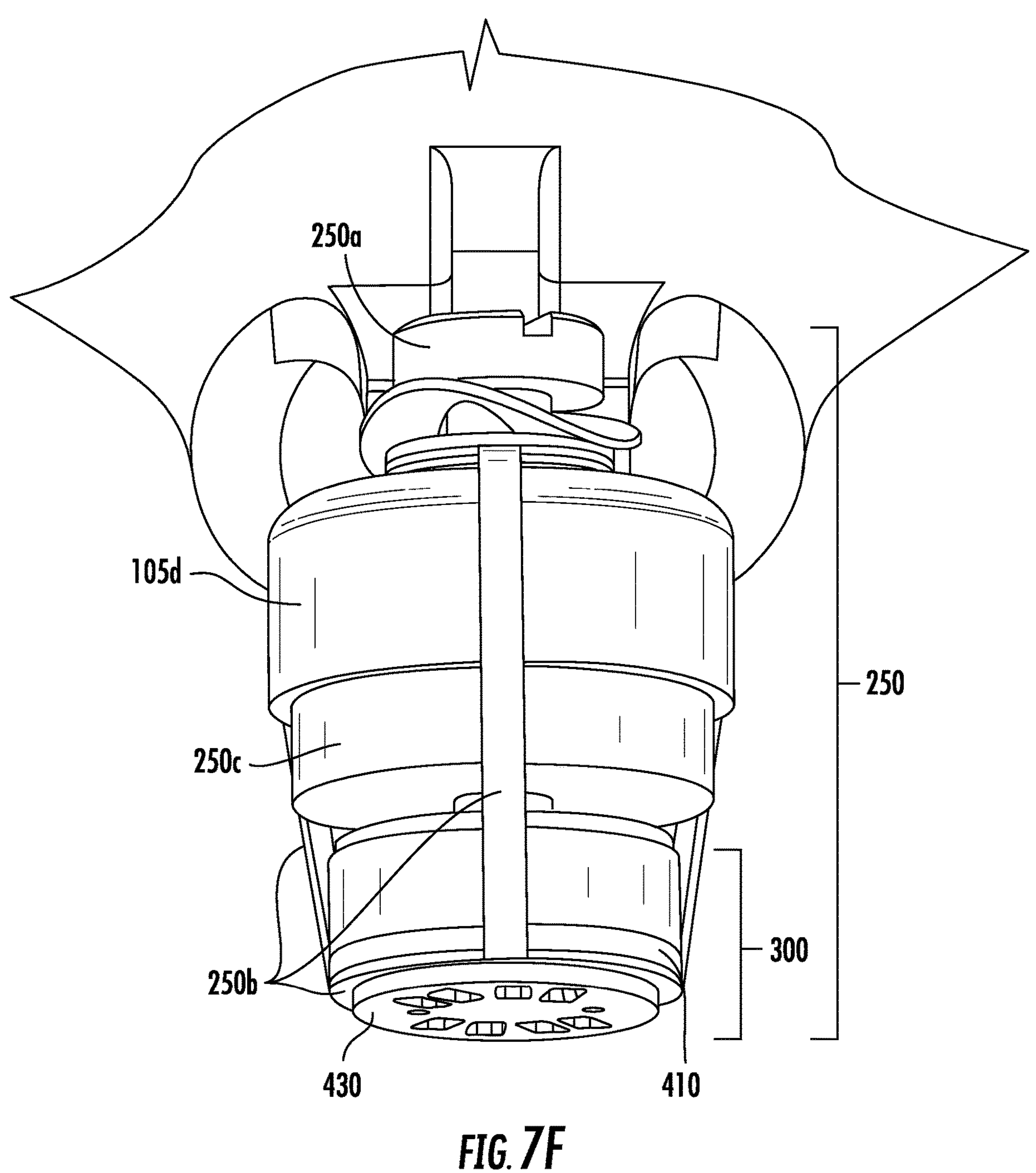
Figure 7G:
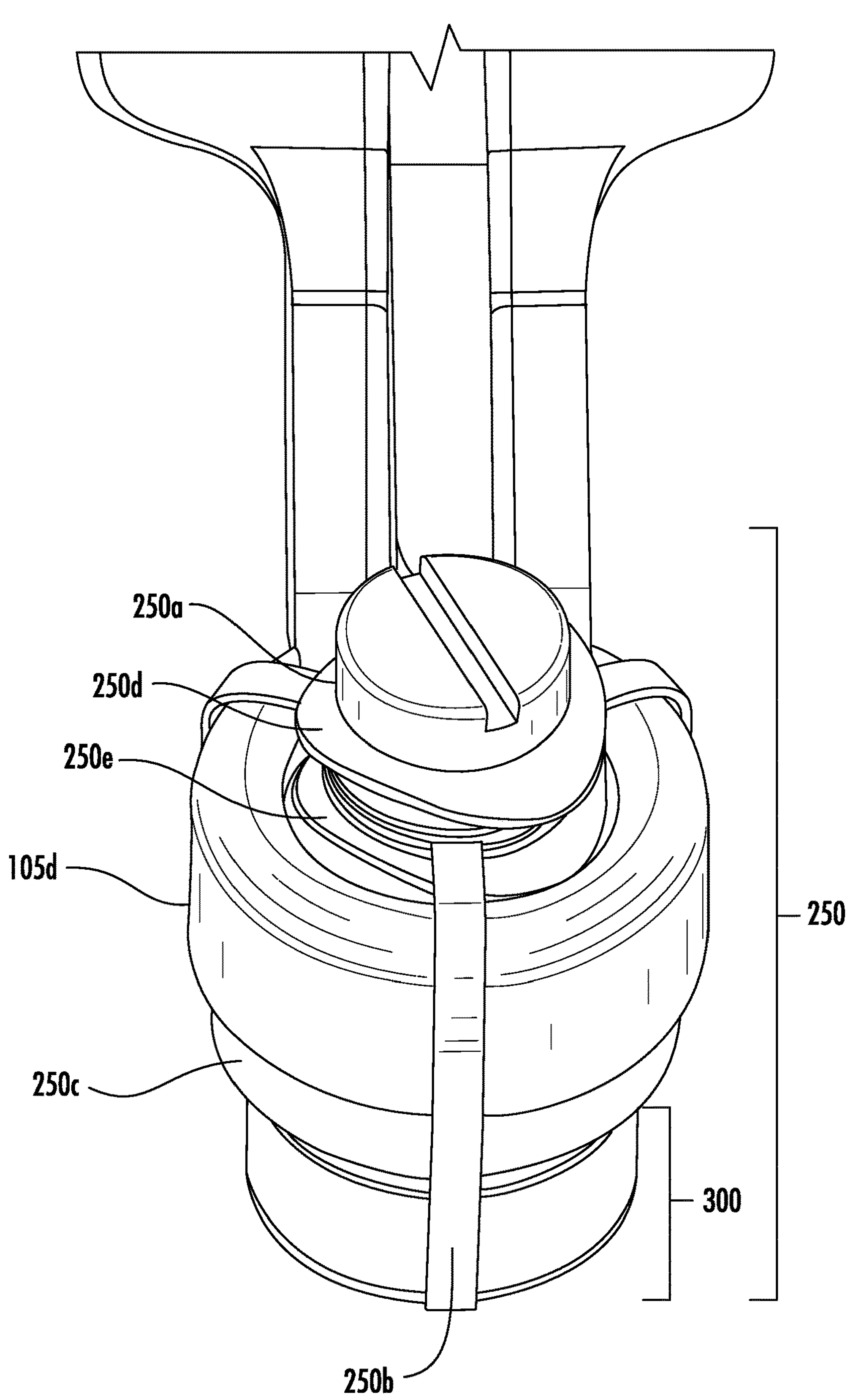
Figure 7H:
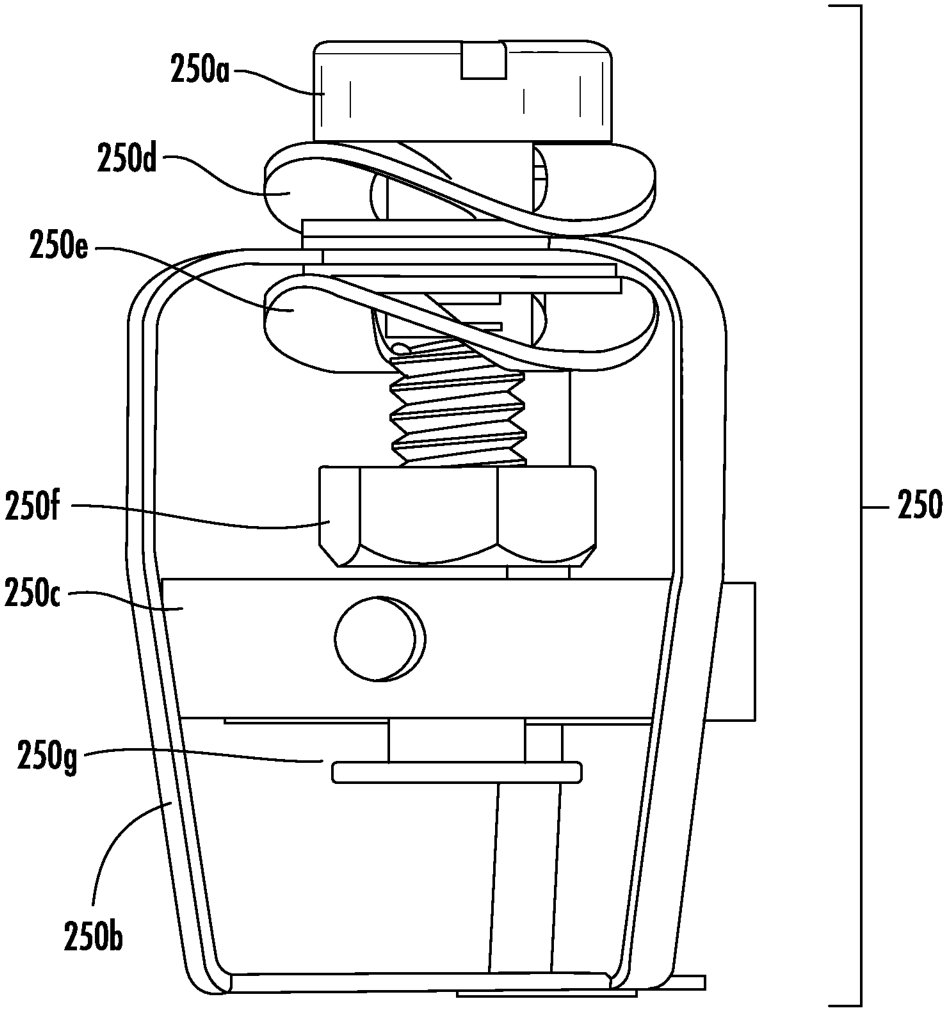
FIG. 7H is an alternative view of the sensor head.

FIGS. 7E, 7F, and 7G are further enlarged views of tip portion 105*c* and sensor head 250 according to one embodiment. Specifically, FIGS. 7E, 7F, and 7G are an enlarged side view, an enlarged front view, and an enlarged perspective view, respectively, of the sensor head and the tip portion of the housing. Tip portion 105*c* of housing 105 may have a disk shaped end 105*d* with an aperture formed therein for receiving a fastener 250*a* to attach the disk shaped end to a cage 250*b* of the sensor head. Cage 250*b* can be configured to hold together various components of the sensor head. For example, the disk shaped end 105*d* of tip portion 105*c* can have a recess formed therein where the recess can be shaped to receive a nut 250*f* (see FIG. 7H) that attaches to fastener 250*a* for attaching top portion 105*c* to cage 250*b*. Specifically, FIG. 7H is a simplified side view of sensor head 250, which is shown without tip portion 105*c* of housing 105 and without probe tip 300 so that nut 250*f* can be shown coupled to fastener 250*a* for a further understanding of the coupling of tip portion 105*c* to cage 250*b*. Further explanation of the view of sensor head 250 that is shown in FIG. 7H is provided below.

Figure 7I:
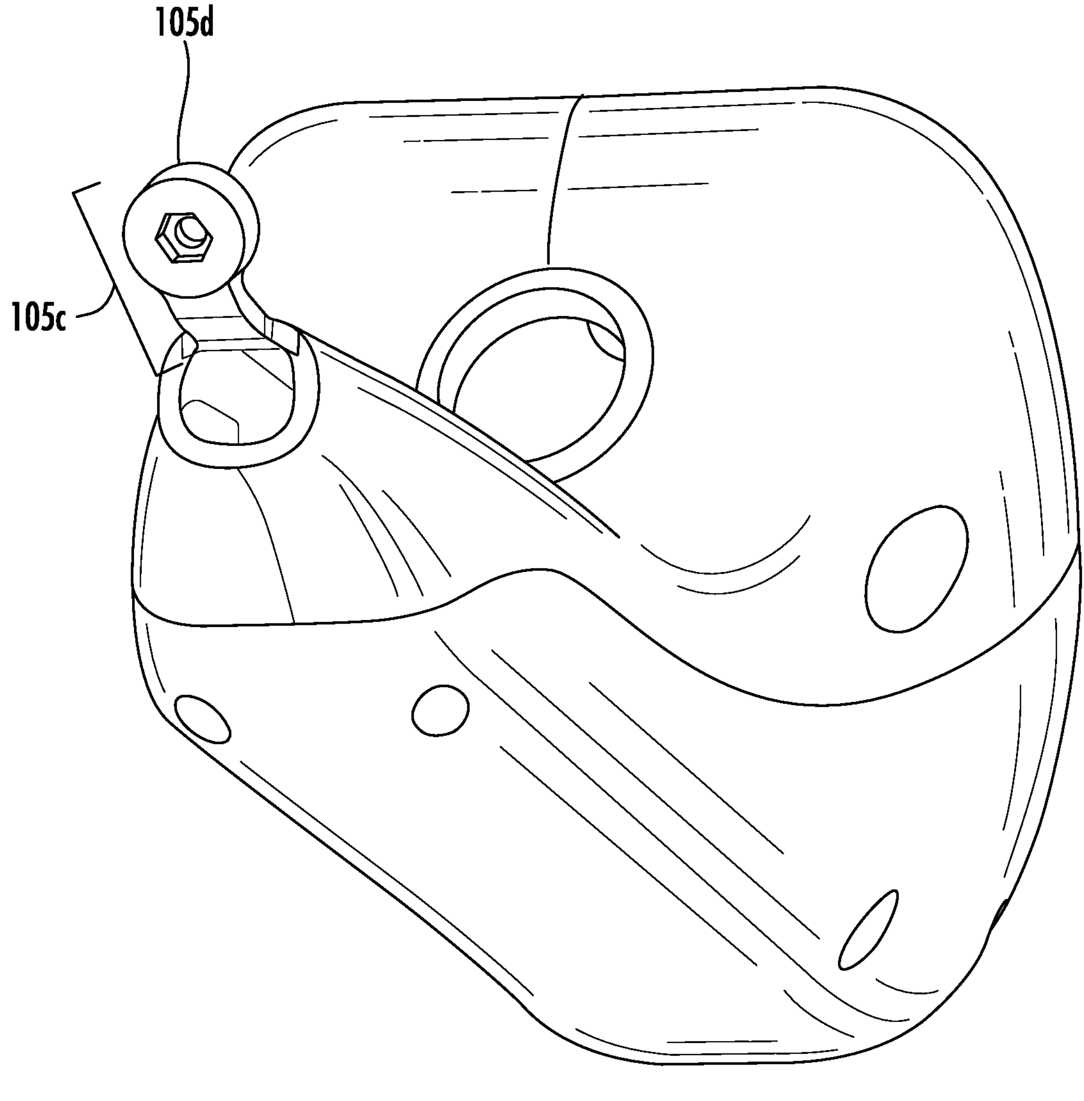
FIG. 7I is an end view of the tip portion of the housing.

FIG. 7I is an end view of the disk shaped end 105*d* of tip portion 105*c* and shows a recess formed therein where the recess is centered about the central aperture of the disk shaped end. As described briefly above, the recess may have a hexagonal shape as shown or may have other useful shapes for receiving nut 250*f* or other similar fasteners.

Sensor head 250 can be 1.25 centimeters to about 4 centimeters long and about 0.7 centimeters to about 2 centimeters wide (e.g., about 1 centimeter in a specific embodiment). Tip portion 105*c* of housing 105 may have a length of about 9 millimeters to about 20 millimeters (e.g., about 12 millimeters in a one specific embodiment). The disk shaped end 105*d* of tip portion 105*c* may have a diameter of about 8 millimeters to about 12 millimeters (e.g., about 10.6 millimeters in a one specific embodiment).

Figure 7J:
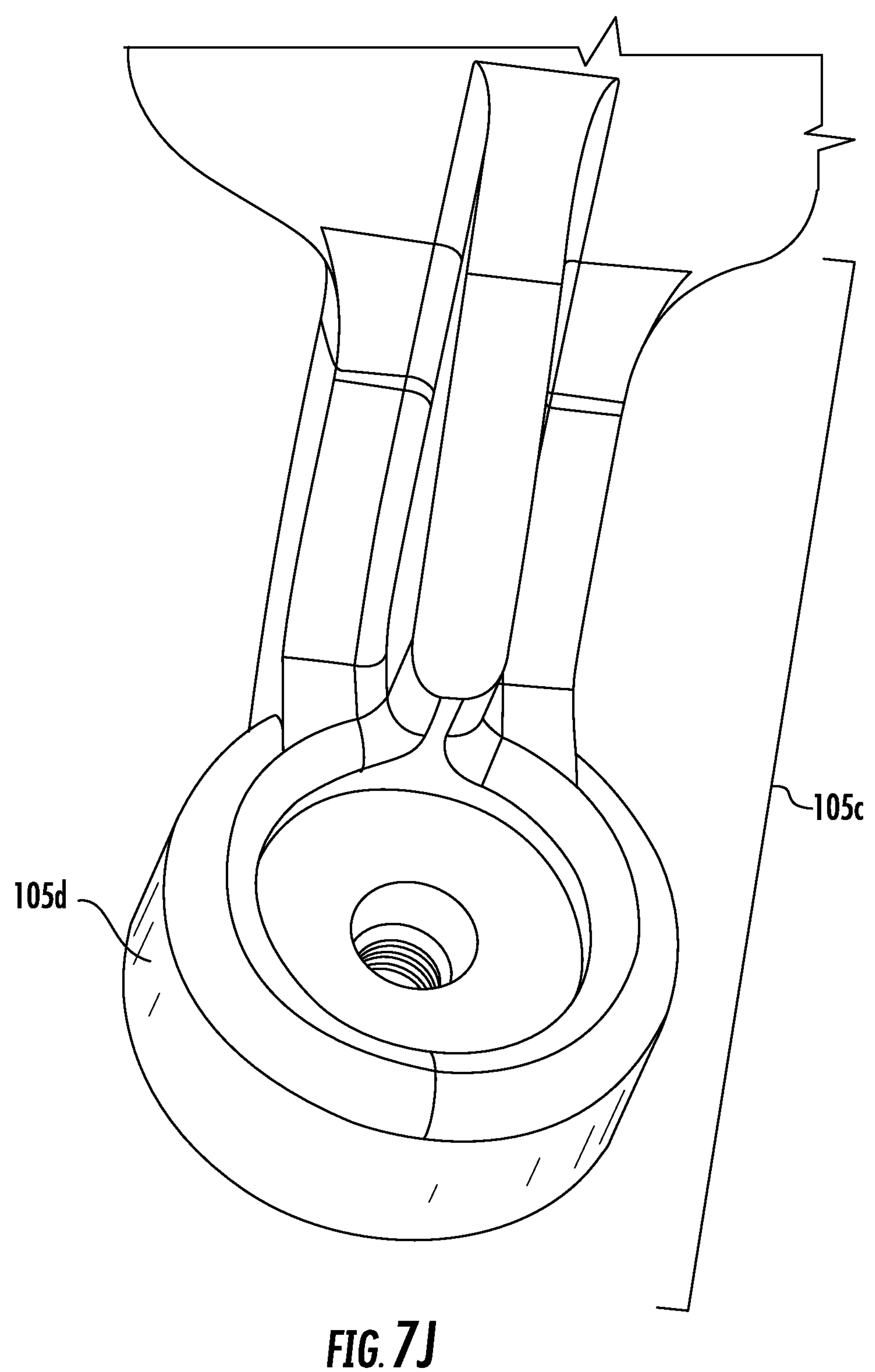
FIG. 7J is a simplified top view of a disk shaped end of the housing.

Sensor head 250 may additionally include one or more spring washers 250*d* and 250*e* where the first spring washer 250*d* can be positioned under the head of fastener 250*a* and the second spring washer 250 can be positioned inside of cage 250*b* and inside a second recess of disk shaped end 105*d* where the second recess is formed in the top of the disk shaped end. FIG. 7J is a simplified top view of disk shaped end 105*d* of housing 105 and shows the second recess formed in the top of the disk shaped end where the recess is centered about the aperture formed therein. Sensor head 250 can include one or more additional washers positioned between the spring washers 250*d* and 250*e* and the top of cage 250*b*.

Sensor head 250 may additionally include a spacer 250*c* positioned between disk shaped end 105*d* and probe tip 300. In some embodiments, spacer 250*c* is pressure sensor 175 (e.g., a force sensing resistor, a load cell, or both) configured to detect the pressure of probe tip 300 against tissue. Pressure on probe tip 300 can be transferred to the pressure sensor where the pressure is detected by the pressure sensor and information for the detected pressure can be transferred from the pressure sensor to acquisition module 115, measurement module 120, or both for reporting this detected pressure to a user, such as on display 125.

Pressure detection and pressure reporting is described further below. It is noted here however that a preload force can be placed on the pressure sensor, for example if the pressure sensor includes a load cell, via the force applied by fastener 250*a*, nut 250*f*, and spring washers 250*d* and 250*e* to the pressure sensor. The preload force can be increased or decreased by tightening or loosening fastener 250*a* and nut 250*f* The preload force can also be used for calibrating the pressure sensor. In embodiment where the pressure sensor is a load cell, the load cell can be about 3 millimeters to about 5 millimeters in height and about 8 millimeters to about 11 millimeters (about 9.6 millimeters in a specific embodiment) in diameter. The load cell can include a button end 250*g* configured to contact probe tip 300 for detecting transferred pressure of the probe tip against the tissue.

Figure 7K:
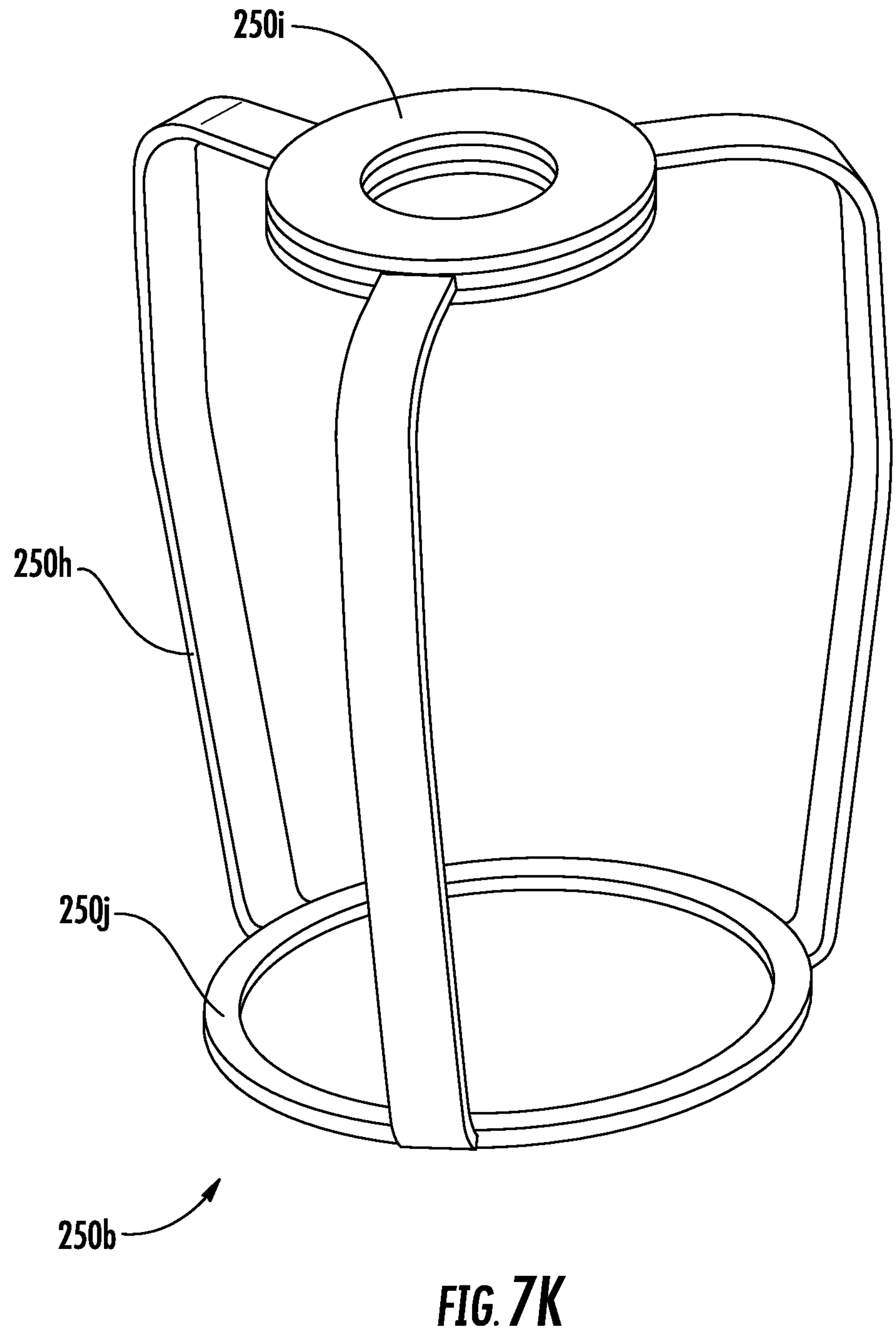
FIG. 7K is a simplified image of the cage.

FIG. 7K is a simplified image of cage 250*b*. Cage 250*b* can be metal, resinated fiber (e.g., carbon fiber, boron fiber, or the like), plastic, or the like. Cage 250*a* may include a body portion 250*h* (e.g., three arms), a top disk 250*i*, and a bottom disk 250*j*, where the body portion links the top disk to the bottom disk. Top disk 250*i* may have a top aperture formed therein where the top aperture is configured to receive fastener 250*a*. Bottom disk 250*j* may have a bottom aperture formed therein where the bottom aperture is configured to accept an aperture plate 430 (see FIGS. 7F, 10A, and 10B) of probe tip 300. Bottom disk 250*j* can form a shoulder for other portions of probe tip 300, such as detector printed circuit board (PCB) 410 of probe tip 300. Probe tip 300, detector PCB 410, and aperture plate 430 are described further below. Cage 250*b* can be about 11 millimeters to about 14 millimeters long (e.g., about 13 millimeters long in a specific embodiment). Cage 205*b* can have a diameter at the bottom of about 7 millimeters to about 9 millimeters (e.g., about 8 millimeters according to one embodiment). Cage 250*b* can have a diameter of about 8 millimeters to about 11 millimeters at the broadest part of the cage.

Figure 8A:
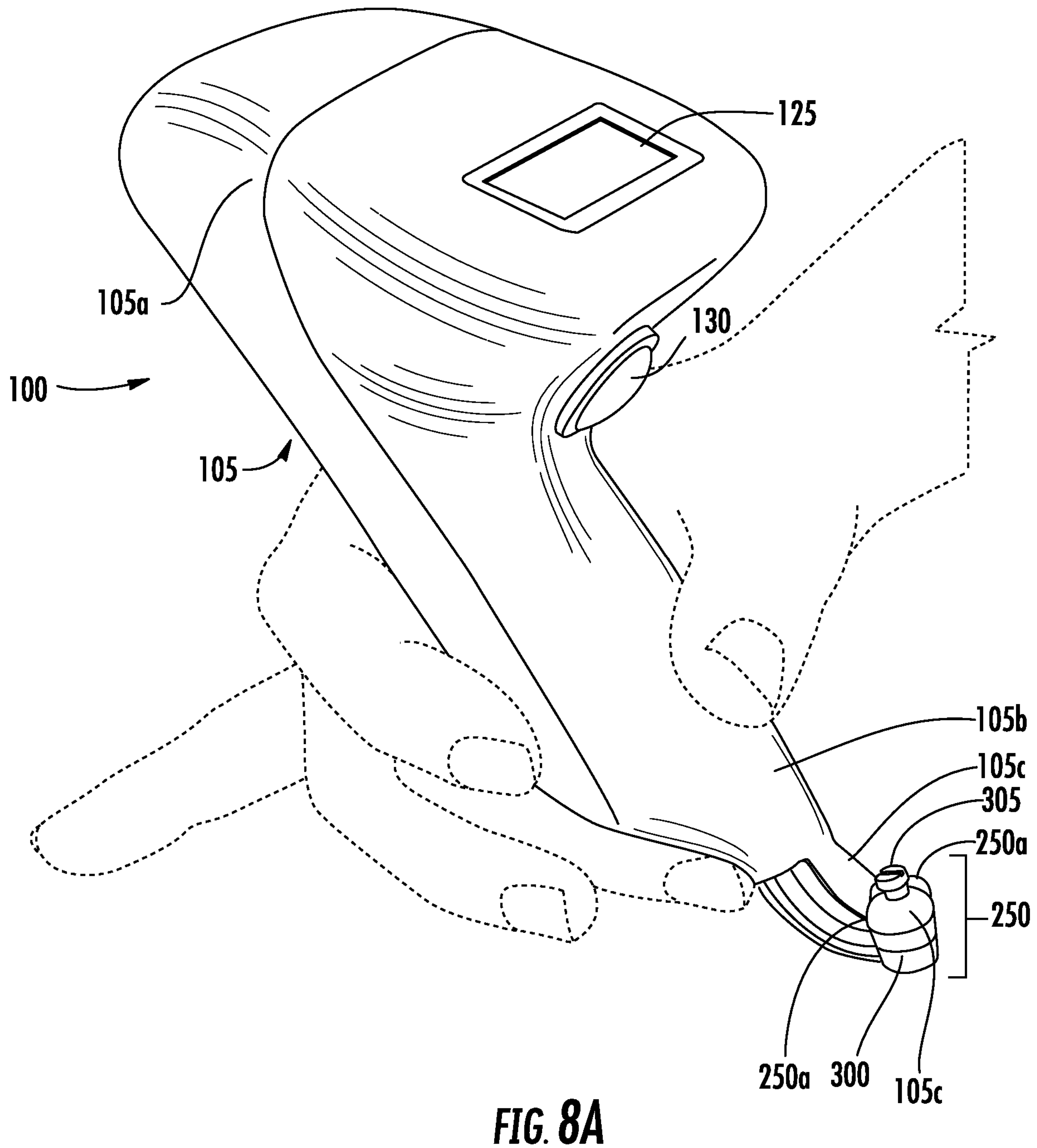
FIGS. 8A and 8B are images of the tissue oximetry device being held by a hand of a user for use.
Figure 8B:
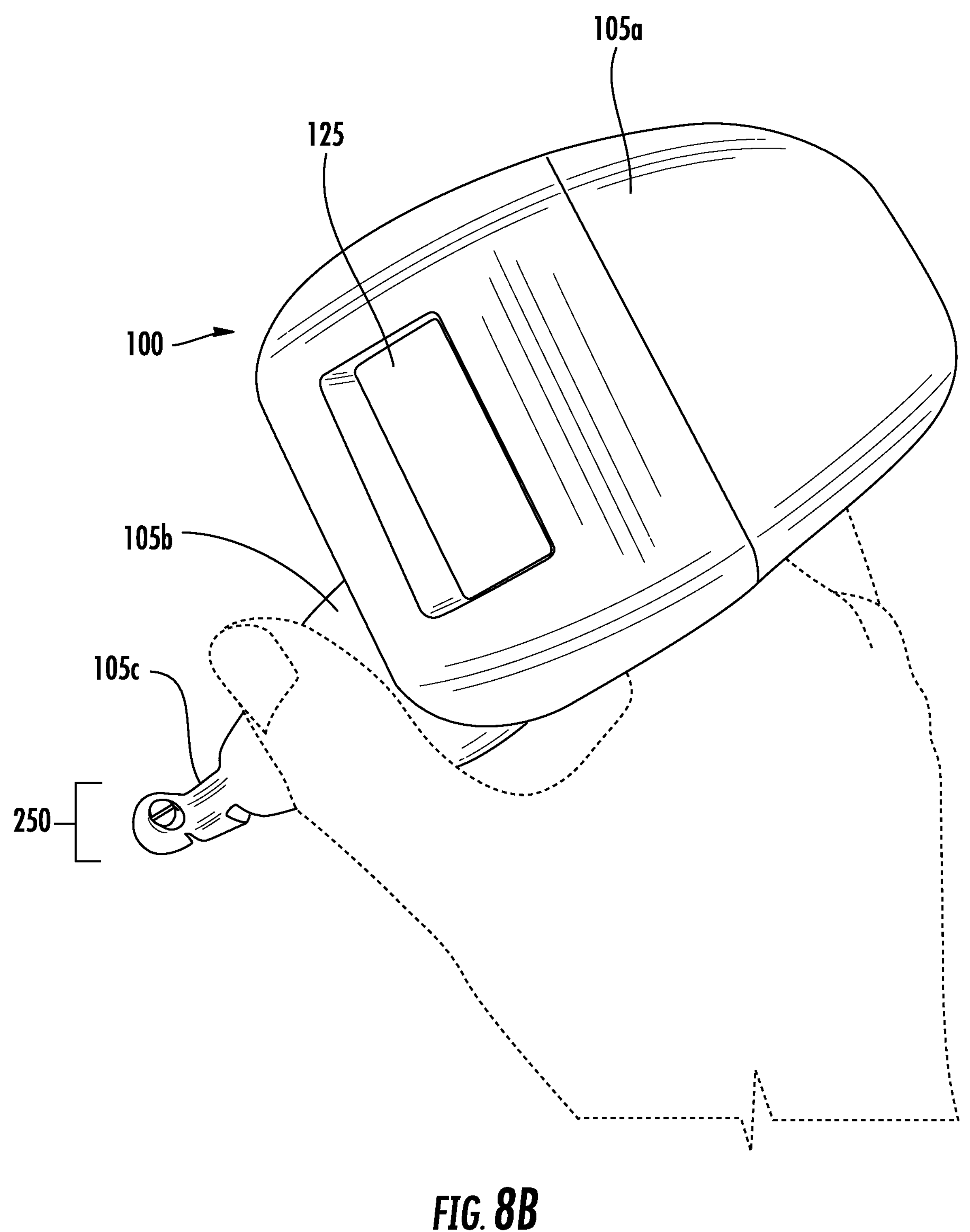

FIGS. 8A and 8B are images of tissue oximetry device 100 being held by a hand of a user for use. Specifically, FIGS. 8A and 8B show the user's hand holding the body portion 105*b* of housing 105 for use. In one method of use, a user may hold body portion 105*b* with a thumb on a front of the body portion and with one or more fingers wrapped around back and sides of the body portion. The mass of tissue oximetry device 100 may thereby be substantially supported by the user's fingers wrapped around body portion 105*b*. While the user's hand is shown as holding body portion 105*b* of housing 105, a user can alternatively hold top portion 105*a* of the housing or a combination of top portion and body portion.

Probe Tip

Figure 9A:
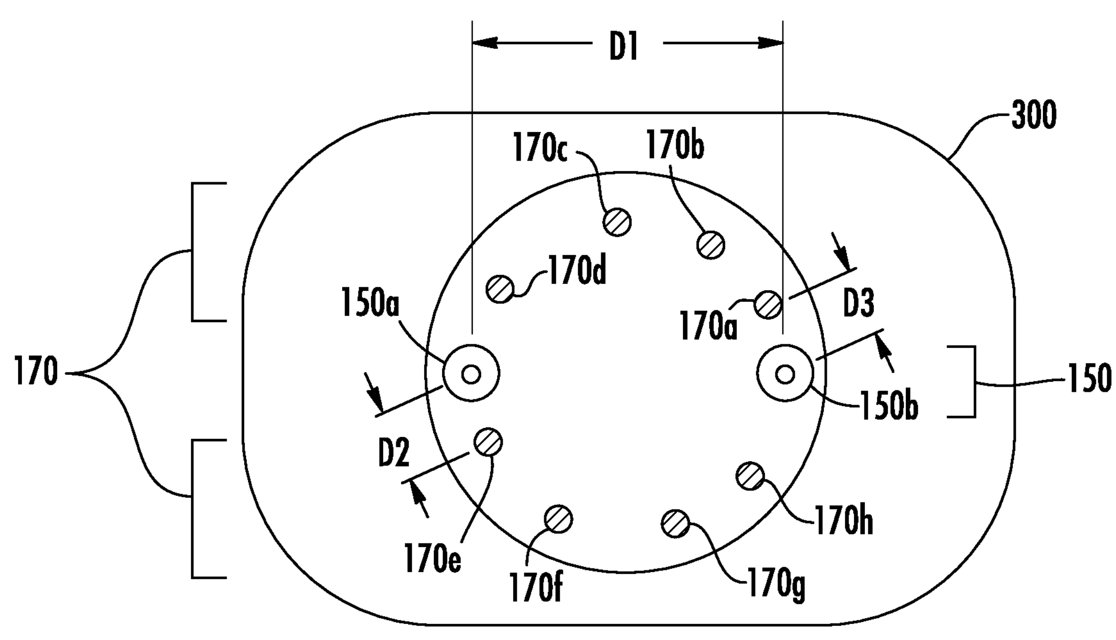
FIG. 9A is a simplified end view of the bottom of the probe tip according to one embodiment.
Figure 9B:
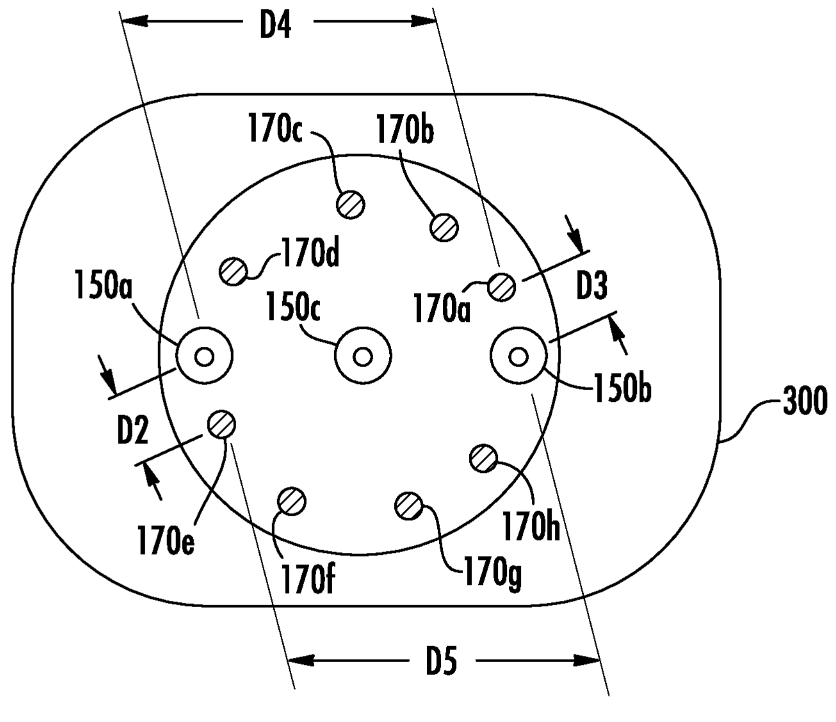
FIG. 9B is a simplified end view of the bottom of the probe tip according to an alternative embodiment.

FIG. 9A is a simplified end view of the bottom of probe tip 300 according to one embodiment. In the embodiment shown in FIG. 9A, probe tip 300 includes two light sources 150*a* and 150*b* and eight light detectors 170*a* to 170*h*. While the specific embodiment in FIG. 9 shows that probe tip 300 includes two light sources and eight light detectors, various alternative embodiments of probe tip 300 may include more or few light sources and may include more or fewer light detectors. For example, in one alternative embodiment, probe tip 300 may include three light sources as shown in FIG. 9B.

As described above, light sources 150 are configured to generate and emit light (e.g., red and near-infrared light) into tissue that tissue oximetry probe 100 is in contact with. The tissue reflects a portion of the light and each light detector 170 detects a portion of the light that is reflected. Each light detector 170 generates reflectance data (i.e., a response) for the portion of light received, and sensor subsystem 110 in combination with measurement module 115 determines an oxygen saturation of the tissue based on the reflectance data.

Light sources 150 can be linearly positioned across probe tip 300 and light detectors 170 can be arranged in an arc or a circle (i.e., circular arrangement) on probe tip 300. More specifically, light sources 150 can be arranged on a line (e.g., a diameter) that bisects a circle on which light detectors 170 can be arranged. Light sources 150*a* and 150*b* can be spaced a distance D1 apart where D1 may range from about 3 millimeters to about 10 millimeters.

In an embodiment where probe tip 300 includes a central light source 150*c* (see FIG. 9B), the central light source 150*c* can be positioned at an approximate midpoint between light sources 150*a* and 150*b*. The central light source 150*c* can be substantially equidistantly (e.g., +/− 10 microns) from each light detector 170 where the distance between the central light source and each light detector is about 1.5 millimeters to 5 millimeters. That is, the circle on which light detectors 170 are arranged may have a diameter of about 3 millimeters to about 10 millimeters (e.g., 4 millimeters according to one specific embodiment).

This maximum distance between the light sources and the detectors substantially limits reflectance data to light that propagated within the top layer of tissue wherein little or no underlying subcutaneous fat or muscular layers contributes to the reflectance data generated by light detectors 170 from light reflected from tissue. Propagation depth increases with increasing source-to-detector distance, with about 4-5 millimeters generally being a sufficient upper limit to ensure few detected photons propagated in lower tissue layers.

While light detectors 170 are described as being arranged in an arc or circle, probe tip 300 may have other configurations of light detectors, such as linear, square, rectangular, pseudo-random, or other arbitrary pattern.

As descried briefly above, the specific embodiment of probe tip 300 shown in FIGS. 9A and 9B includes eight light detectors 170*a*, 170*b*, 170*c*, 170*d*, 170*e*, 170*f*, 170*g*, and 170*h*. In other specific embodiments, however, probe tip 300 may include two or more light detectors 170.

Light detectors 170 can be solid state detectors and can be mounted to detector printed circuit board 410. Further, light detectors 170 can be combined devices or discrete devices.

Acquisition module 115, measurement module 120, or both can be configured to control light sources 150 and light detectors 170 via a set of electrical traces that run through the one or more printed circuit boards on which the light sources and the light detectors are mounted. The circular configuration of light detectors 170 and the linear arrangement of light sources 155 allows for a relatively simple arrangement of the electrical traces in these printed circuit boards. For example, the electrical traces may radially extend outward from lights sources 150 and light detectors 170 so that the electrical traces do not overlap in the one or more PCBs on which these devices are mounted, which allows for relatively even spacing between the electrical traces and thereby provides for relatively low electrical crosstalk between the electrical traces. In some situations, relatively low crosstalk between the electrical traces lowers the signal-to-noise ratio of both the light sources 150 and the light detectors 170 as compared to electrical traces that are alternatively arranged.

In a specific implementation, light detectors 170 are positioned with respect to light sources 150*a* and 150*b* such that two or more (e.g., fourteen) unique source-to-detector distances are created. With greater numbers of source-to-detector distances, this can be used to obtain greater accuracy, faster calibration, and redundancy (when duplicate source-to-detector distances are provided). At least one source-to-detectors distances is about 1.5 millimeters or less (e.g., 0.5 millimeters up to about 1.7 millimeters), and at least one source-to-detectors distances is about 2.5 millimeters or greater (e.g., 1.5 millimeters up to about 3.2 millimeters).

For example, in one embodiment, a first source-to-detector distance is about 1.5 millimeters or less. A second source-to-detector distance is about 1.5 millimeters or less. A third source-to-detector distance is about 2.5 millimeters or greater. A fourth source-to-detector distance is about 2.5 millimeters or greater. There can be various numbers of light sources and light detector arrangements to obtain these four source-to-detector distances, such as one light source and four light detectors, two light sources and two light detectors, one light detector and four light sources, or other arrangements and combinations.

For example, one embodiment includes at least two light sources and at least two light detectors, where a maximum distance between a light source and a light detector is about 4 millimeters (or about 5 millimeters), where at least one source-to-detector distance is about 2.5 millimeters or greater, and where at least one source-to-detector distances is about 1.5 millimeters or less.

When a greater number of light sources and light detectors are included in the probe tip, greater numbers of source-to-detector distances are available. As discussed, these can be used to provide greater accuracy, faster calibration, or redundancy, or a combination or these. The arrangement of the light sources and light detectors can be in a circular pattern, such as at points along the arc of a circle with radius of about 4 millimeters to about 5 millimeters. In an implementation, a tolerance of the positions of the light detector or the light source on the arc is within 10 microns of the arc curve. In other implementations, the tolerance is within about 0.25 millimeters.

The foregoing described source-to-detectors distances allow for the determination of the scattering coefficient and the absorption coefficient via SRS from the reflectance data, which is generated by light detectors 170. Specifically, the reflectance data that is generated by light detectors 170, which have relatively small source-to-detector distances (e.g., 1.5 millimeters or closer), is a function of the scattering coefficient of tissue and not the absorption coefficient. Further, the reflectance data that is generated by light detectors 170, which have relatively large source-to-detector distances (e.g., 2.5 millimeters or farther), is a function of the μeff (the inverse of the penetration depth), where μeff is a function of both the scattering coefficient and the absorption coefficient. With at least two light detectors 170 positioned at 1.5 millimeters or closer to at least one light source 150, and with at least two detectors positioned at 2.5 millimeters or farther from at least one light source 150, the scattering coefficient and the absorption coefficient can be independently determined.

According to one specific embodiment, sixteen unique source-to-detector distances are provided. The sixteen unique source-to-detector distances can be: 150*a*-170*d*=1.000 millimeter; 150*b*-170*h*=1.249 millimeters; 150*a*-170*e*=1.500 millimeters; 150*b*-170*a*=1.744 millimeters; 150*a*-170*c*=2.000 millimeters; 150*b*-170*g*=2.261 millimeters; 150*a*-170*f*=2.500 millimeters; 150*b*-170*b*=2.712 millimeters; 150*a*-170*b*=2.940 millimeters; 150*b*-170*f*=3.122 millimeters; 150*a*-170*g*=3.300 millimeters; 150*b*-170*c*=3.464 millimeters; 150*a*-170*a*=3.600 millimeters; 150*b*-170*e*=3.708 millimeters; 150*a*-170*h*=3.800 millimeters; and 150*b*-170*d*=3.873 millimeters where these distances may vary by about +/−10 microns.

In one alternative embodiment, at least two of the source-to-detector distances are the same, such as the shortest source-to-detector distances. For example, the shortest source-to-detector distance D2 between light source 150*a* and light detector 170*e*, and the shortest source-to-detector distance D3 between light source 150*b* and light detector 170*a* can be the same. It follows that the source-to-detector distance D4 between light source 150*a* and light detector 170*a*, and the source-to-detector distance D5 between light source 150*b* and light detector 170*e* may also be the same. The source-to-detector distances D4 and D5 are the longest source-to-detector distances for light sources 150*a* and 150*b*. The foregoing description is for an example embodiment. For example, other pairs of source-to-detector distances can be the same, such as the next to shortest source-to-detector distances, and the next to longest source-to-detector distances.

With the exception of the shortest source-to-detector distance and the longest source-to-detector distance for light sources 150*a* and 150*b*, the source-to-detector distances for light sources 150*a* and 150*b* can be unique. As described above, probe tip 300 may have fourteen unique source-to-detector distances that allow for fourteen reflectance data points to be collected by light detectors 170*a*-170*h* from light emitted from light sources 150*a* and 150*b*.

Furthermore, the source-to-detector distances for light sources 150*a* and 150*b* may also be selected such that increases in these distances are substantially uniform. Thereby, a plot of source-to-detector distance verses reflectance detected by light detectors 170 can provide a reflectance curve where the data points are substantially evenly spaced along the x-axis. These source-to-detector distances and the uniform increase thereof for light sources 150*a* and 150*b* reduce data redundancy and can lead to the generation of relatively accurate reflectance curves.

Figure 10A:
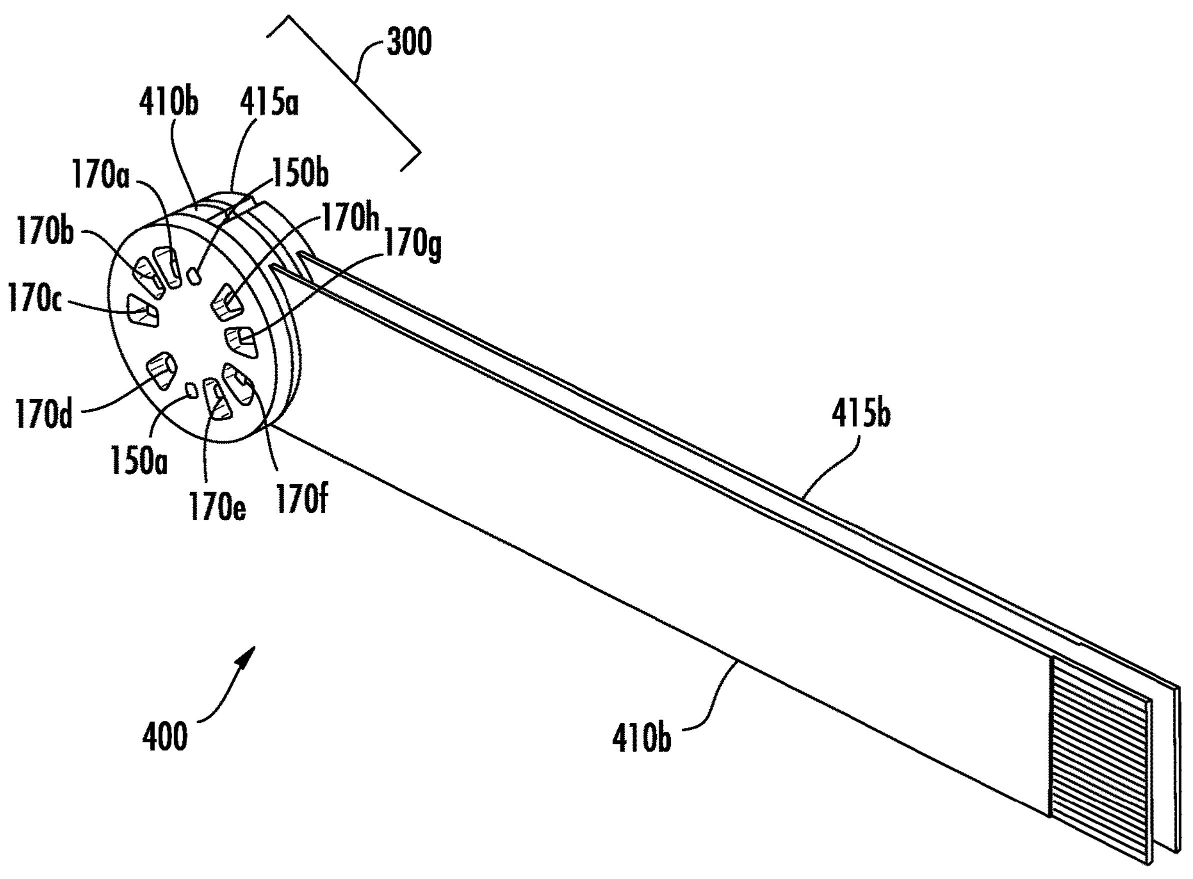
FIGS. 10A and 10B are a simplified perspective view and an exploded view, respectively, of the source-sensor assembly that composes at least a portion of the sensor subsystem.
Figure 10B:
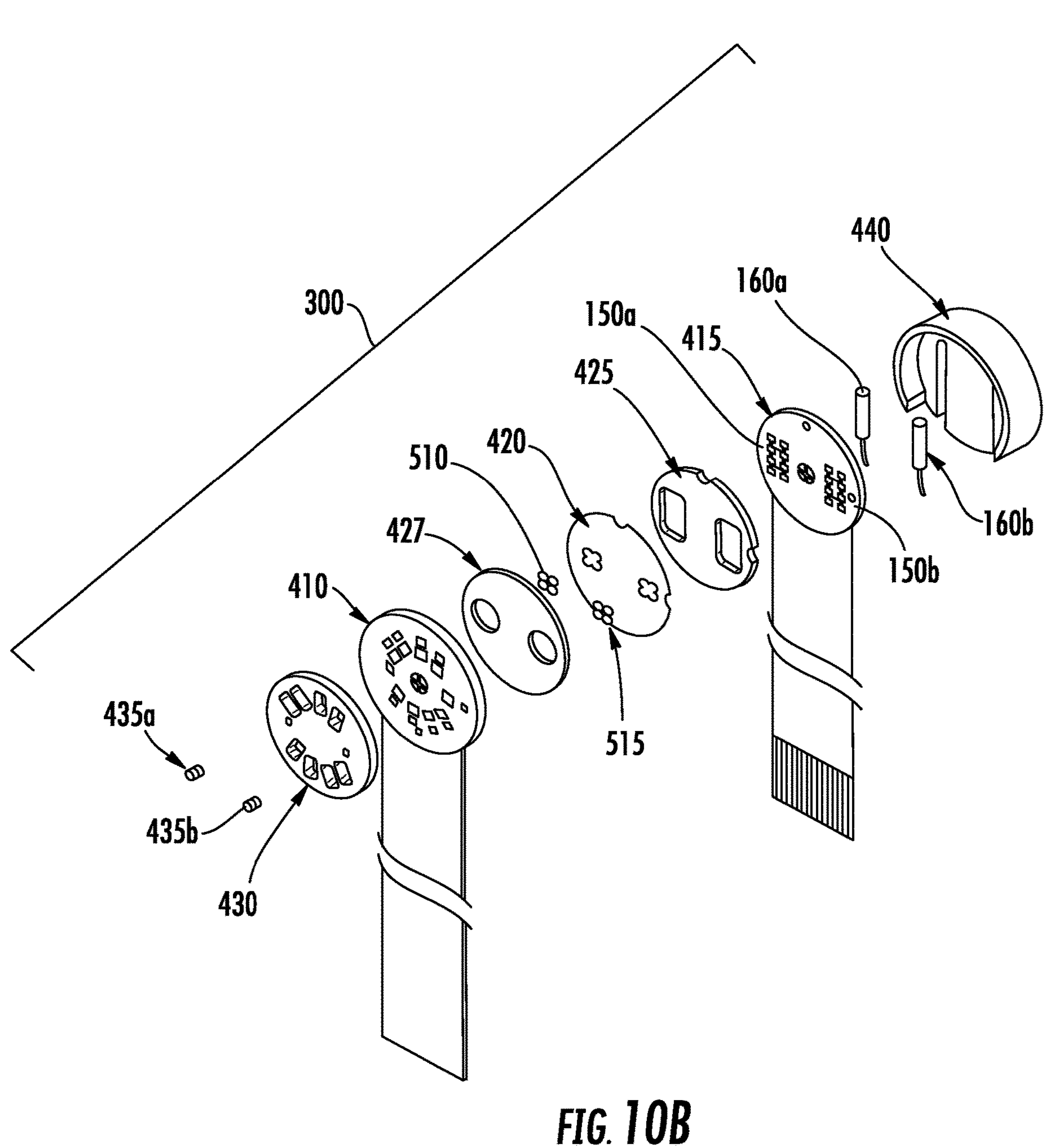

FIGS. 10A and 10B are a simplified perspective view and an exploded view, respectively, of a source-sensor assembly 400 that composes at least a portion of sensor subsystem 110 according to one specific embodiment. Source-sensor assembly 400 includes probe tip 300, which is located and one end of the source-sensor assembly. Probe tip 300 can be composed of portions of one or more components of the source-sensor assembly.

In one embodiment, source-sensor assembly 400 includes detector PCB 410 and source PCB 415 that are configured to electrically couple probe tip 300 to acquisition module 115. Light detectors 170 can be mounted on detector PCB 410, and light sources 150 can be mounted on source PCB 410. Detector PCB 410 may include a rigid portion 410*a* (shown as generally round in FIGS. 10B) to which light detectors 170 are mounted, and may include a flexible portion 410*b* that is configured to route electrical signal between the light detectors and acquisition module 115. Source PCB 415 may similarly include a rigid portion 415*a* (shown as generally round in FIGS. 10B) to which light source 150 are mounted, and may include a flexible portion 415*b* that is configured to route electrical signal between light sources 150 and acquisition module 115.

The flexible portion 410*b* of detector PCB 410 and flexible portion 415*b* of source PCB 415 are shown in FIGS. 7C and 7D in a flexed configuration with rigid portions 410*a* and 415*a* coupled to cage 250*a* and connector ends electrically and physically coupled to PCB 115*a* of acquisition module 115. The connector ends of flexible portions 410*b* and 415*b* can be one of a variety of connectors types that are configured to couple to PCB 115*a*. In one implementation, the connector's ends of flexible portions 410*b* and 415*b* may include zero insertion force (ZIF) connectors that connect to corresponding ZIF connectors on PCB 115*a*. The electrical connectors on flexible portions 410*b* and 415*b* may have a pitch of about 0.5 millimeters and can be 10-pin FH12 series HIROSE connectors. The part number of the HIROSE connectors can be FH12-10S-0.55H. The flexible portions 410*b* of detector PCB 410 and 415*b* of source PCB 115 may each be about 40 millimeters to about 50 millimeters long (e.g., a bout 46 millimeters in one specific embodiment) and can be about 4 millimeters to about 6.5 millimeters wide (e.g., about 5.5 millimeters in one specific embodiment).

In one implementation, light sources 150*a* and 150*b* are mounted (e.g., soldered) on rigid portion 415*a* of source PCB 415. For example, if light source 150*a* includes a number of LEDs, these LEDs can be mounted on rigid portion 415*a*, and if light source 150*b* includes a number of LEDs, these LEDs may also be mounted on rigid portion 415*a*.

Figure 10C:
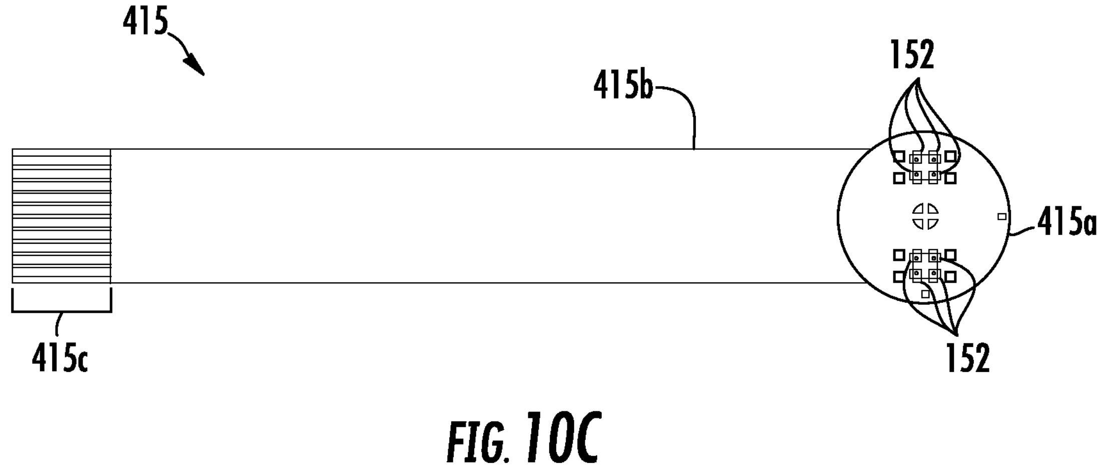
FIG. 10C is a simplified front of the source printed circuit board.
Figure 10D:
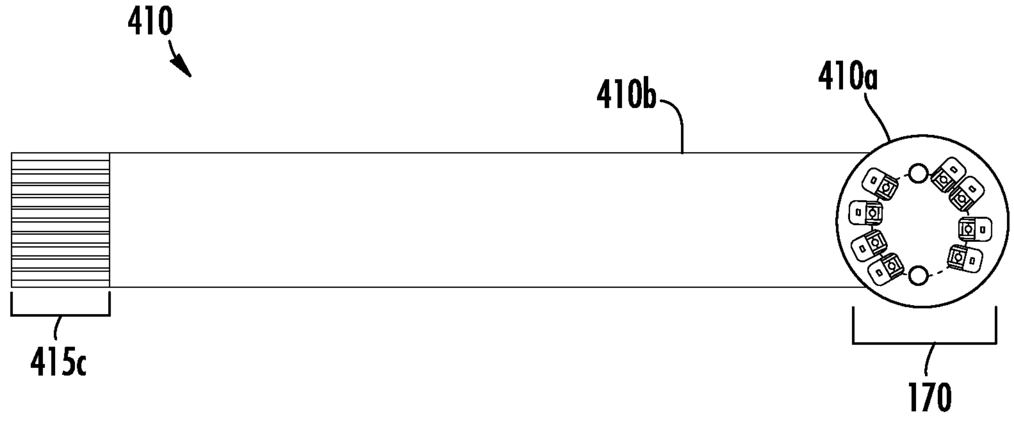
FIG. 10D is simplified front view the detector printed circuit board.

In another implementation, light detectors 170 are mounted (e.g., soldered) on rigid portion 410*a* of detector PCB 410. For example, if light detectors 170 are photodiodes, these photodiodes can be mounted on rigid portion 410*a*. FIG. 10C is a simplified front view of source PCB 415 and FIG. 10D is simplified front view of detector PCB 410. While source-sensor assembly 400 is described as including two PCBs that have the light sources and light detectors mounted on the two different PCBs, the light sources and light detectors can be mounted on a single PCB.

Two sets of lenses 510 and 515 can be positioned adjacent to light sources 150*a* and 150*b*, respectively, to direct light emitted from these light sources forward. More specifically, each set of lenses 510 and 515 may include one or more lenses to direct light emitted from light sources 150*a* and 150*b* forward. According to one specific embodiment, the set of lenses 510 includes a number of lenses that equals the number of lighting elements 152 in light source 150*a*, and the set of lenses 515 includes a number of lenses equal to the number of lighting elements included in light source 150*b*. Further, the lenses in the set of lenses 510 respectively correspond to lighting elements 152 in light source 150*a*, and the lenses in the set of lenses 515 respectively correspond to the lighting elements 152 in light source 515. The lenses can be hemispherical or the like. According to an alternative specific embodiment, a single lens directs the light from light source 150*a* forward and another single lens directs the light emitted from light source 150*b* forward.

Source-sensor assembly 400 may include a lens plate 420 that holds the lenses in alignment for substantially optimal forward direction of emitted light. Lens plate 420 can be coupled between an LED aperture plate 425 and a spacer plate 427 where the LED aperture plate and the spacer plate have apertures formed therein that are adjacent to the apertures in lens plate 420 for permitting light emitted from light sources 150*a* and 150*b* to pass forward from probe tip 300.

Contact plate 430 can be coupled to the front of the rigid portion 410*a* of detector PCB 410. Both the rigid portion 410*a* of detector plate 410 and contact plate 430 have apertures formed therein for further allowing light emitted from light sources 150*a* and 150*b* to pass forward from probe tip 300. Contact plate 430 may also include a number of apertures formed therein for allowing the light scattered back from the tissue to pass to light detectors 170.

In one embodiment, source-sensor assembly 400 includes first and second fiber optic cables 435*a* and 435*b* (generally fiber optic cables 435, sometimes referred to as waveguides) that are optically coupled, respectively, to light sources 150*a* and 150*a* via the sets of lenses 510 and 515. The fiber optic cables can be multimode glass fiber cables. One type of fiber optic cables that can be included in source-sensor assembly 400 has an outside diameter of about 440 micrometers and a core diameter of 400 micrometers.

The first and second fiber optic cables 435*a* and 435*b* can be positioned in one or more of the apertures formed in aperture plate 425, in the rigid portion 410*a* of detector PCB 410, and in contact plate 430. In one embodiment, the sets of lenses 510 and 515 are, respectively, configured to focus the light emitted from light sources 150*a* and 150*b* into the first and second fiber optic cables 435*a* and 435*b*. The first and second fiber optic cables 435*a* and 435*b* are configured to diffuse the light (sometimes referred to as mixing the light) so that the light emerges from the fiber optic cables with substantially homogeneous intensity across the openings of the fiber optic cables to thereby evenly illuminate the tissue. The first and second fiber optic cables 435*a* and 435*b* may each be about 1 millimeter to about 20 millimeters long and in one particular embodiment are about 10 millimeters long. The diameter of the first and second fiber optic cables 435*a* and 435*b* can be a function of the length of the fiber optic cables. For example, the length of each fiber optic cable can be ten times the diameter of the fiber optic cable so that a relatively homogeneous intensity of light is emitted therefrom.

Figure 11A:
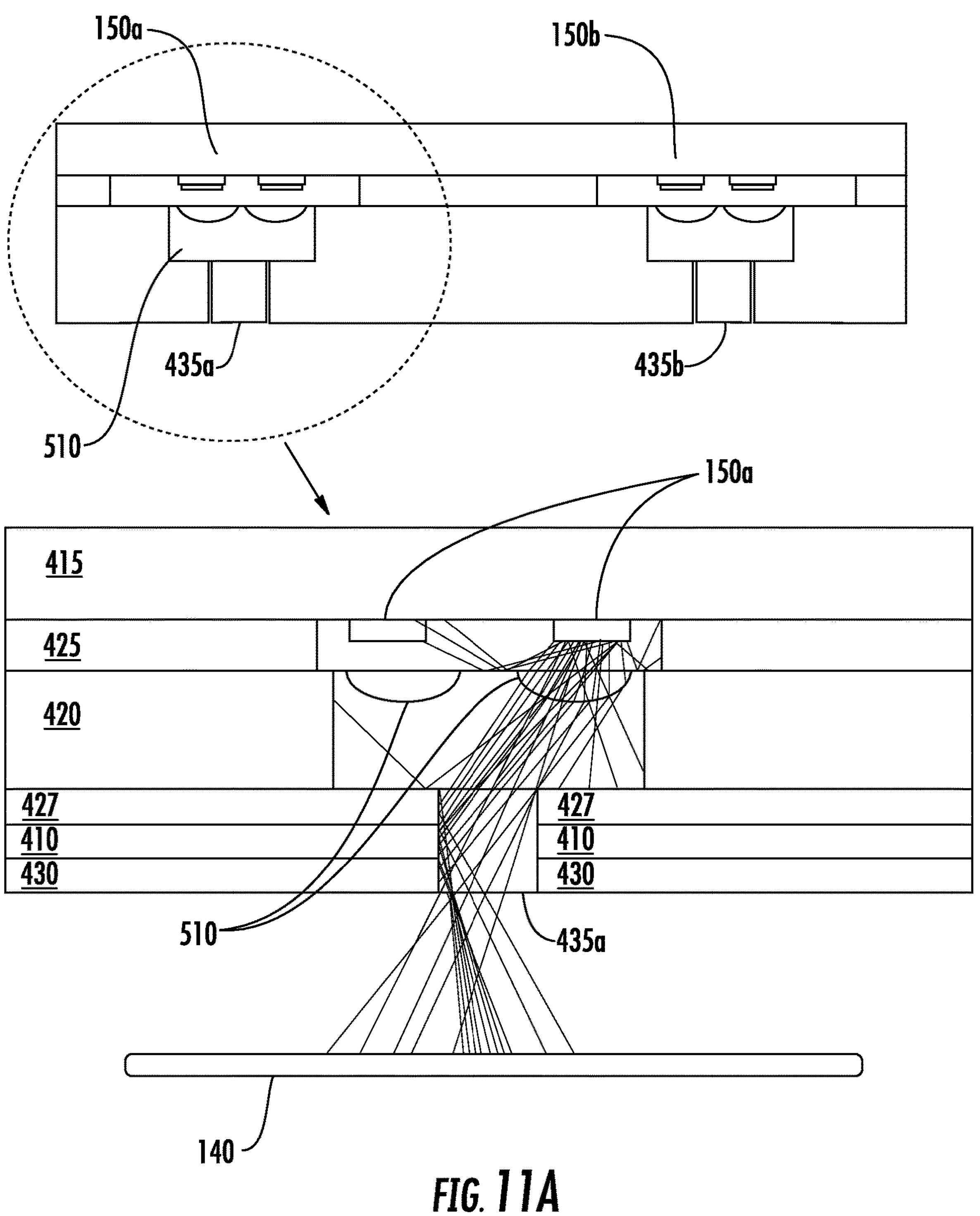
FIG. 11A is a cross-sectional view of the source-sensor assembly and shows light emitted from one of the lighting elements and passing through one of the lenses and one of the fiber optic cables.

FIG. 11A is a cross-sectional view of source-sensor assembly 400 and shows light emitted from one of lighting elements 152 passing through one of the lenses 510 and passing through one of the fiber optic cables 435 for emission into tissue 140. The cross-sectional view shows the mixing of the light in the fiber optic cable. The cross-sectional view also shows the stacked configuration of probe tip 300 according to one embodiment. The thicknesses of the various elements stacked in probe tip 300 may not be drawn to scale in FIG. 11A.

Referring again to FIG. 10B, source-sensor assembly 400 further include temperature sensor 160 (e.g., first and second thermistors 160*a* and 160*b*) and include an end cap 440 according to one embodiment. End cap 400 can be configured to house the temperature sensor. For example, end cap 440 may include one or more recesses (e.g., first and second trenches), one or more apertures, or the like formed therein for holding temperature sensor 160 (e.g., thermistors 160*a* and 160*b*) adjacent to source PCB 415 to monitor the temperature of the light sources. Thermistors 160*a* and 160*b* can be relatively elongated devices where longitudinal axes of the thermistors substantially align with configurations (e.g., square, rectangular, or the like) of lighting elements 152 of light sources 150*a* and 150*b* on source PCB 152.

Figure 11B:
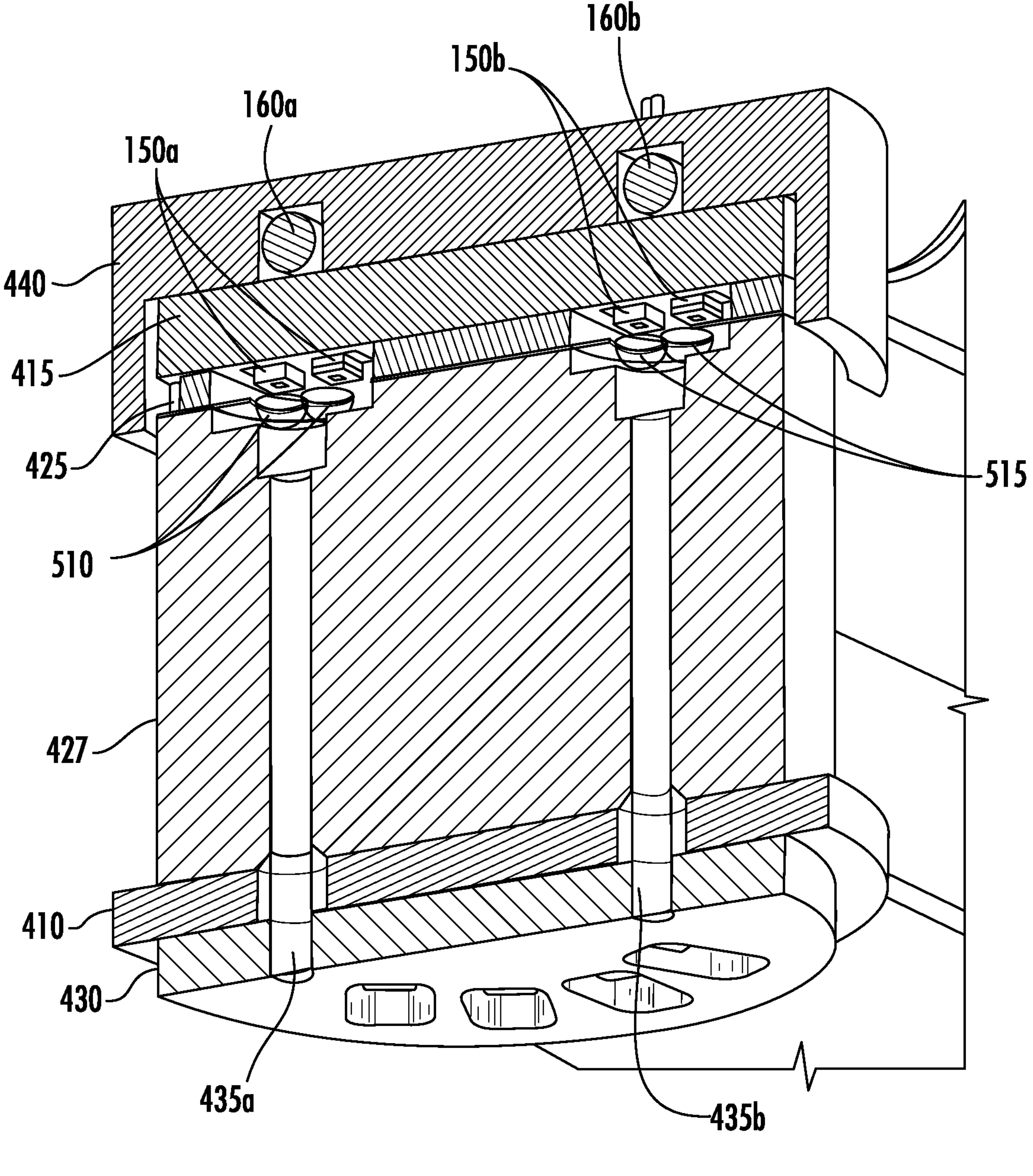
FIG. 11B is a cross-sectional view of the source-sensor assembly according to one alternative embodiment where the spacer plate and the fiber optic cables are elongated.

FIG. 11B is a cross-sectional view of source-sensor assembly 400 according to one alternative embodiment where spacer plate 427 and fiber optic cables 435*a* and 435*b* are relatively elongated compared to the embodiments of spacer plate 427 and fiber optic cables 435*a* and 435*b* shown in FIG. 11A. For example, spacer plate 427 and fiber optic cables 435*a* and 435*b* shown in the embodiment of FIG. 11A can be about 1 millimeters to about 2.5 millimeters in height, and can about 5 millimeters to about 20 millimeters in height in the embodiment shown in FIG. 11B. Each of detector PCB 410, source PCB 415, lens plate 420, aperture plate 425, spacer plate 427, and contact plate 430 can range in thickness from about 0.5 millimeters to about 2 millimeters. The diameters of each of the rigid portion 410*a* of detector PCB 410, the rigid portion 415*a* of source PCB 415, lens plate 420, aperture plate 425, and spacer plate 427 can range from about 4 millimeters to about 10 millimeters, and the diameter of contact plate 430 can range in diameter from about 3 millimeters to about 8 millimeters.

FIG. 10C is a planar view of source PCB 415 and shows lighting elements 152 arranged in square configuration in both light source 150*a* and 150*b*. While lighting elements 152 are shown in FIG. 10C as being in a relatively square configuration, the lighting elements can be arranged in alternative configurations, such as rectangular, circular, ovoid, or the like.

FIG. 10C further shows the connector end of source PCB 415 and shows the electrical contact pads 415*c* of the connector end. The electrical contact pads may form portions of electrical traces that run from the connector end to electrical pads on which the lighting elements are electrically connected. Some of the electrical contact pads 415*c* can be ground pads that connect to ground traces, ground pads, or both. The grounds are configured to provide a controlled electrical environment (e.g., 50-ohm resistance for the electrical traces) for the control signals that are transmitted through the electrical traces to the light sources. Electrical contact pads 410*c*, electrical traces, and grounding elements of detector PCB 410 can be similarly configured as shown in FIG. 10D. In one embodiment, the outer most contact pads and traces in detector PCB 410 and source PCB 415 are the grounds, and the central contact pads and traces are the signal pads and traces.

While light detectors 170 are shown as being configured to receive light substantially directly from the tissue, in one alternative embodiment, the light detectors can be configured to receive the light from one or more fiber optic cables that route the light to the light detectors. Further, while light sources 150 and light detectors 170 are described and shown as being in probe tip 300, the light sources and the light detectors can be located within housing 105, such as within body portion 105*b* of the housing. In this configuration, light sources 150 and light detectors 170 can be optically coupled to probe tip 300 via one or more fiber optic cables.

Calibration of Sources and Detectors

Figure 12:
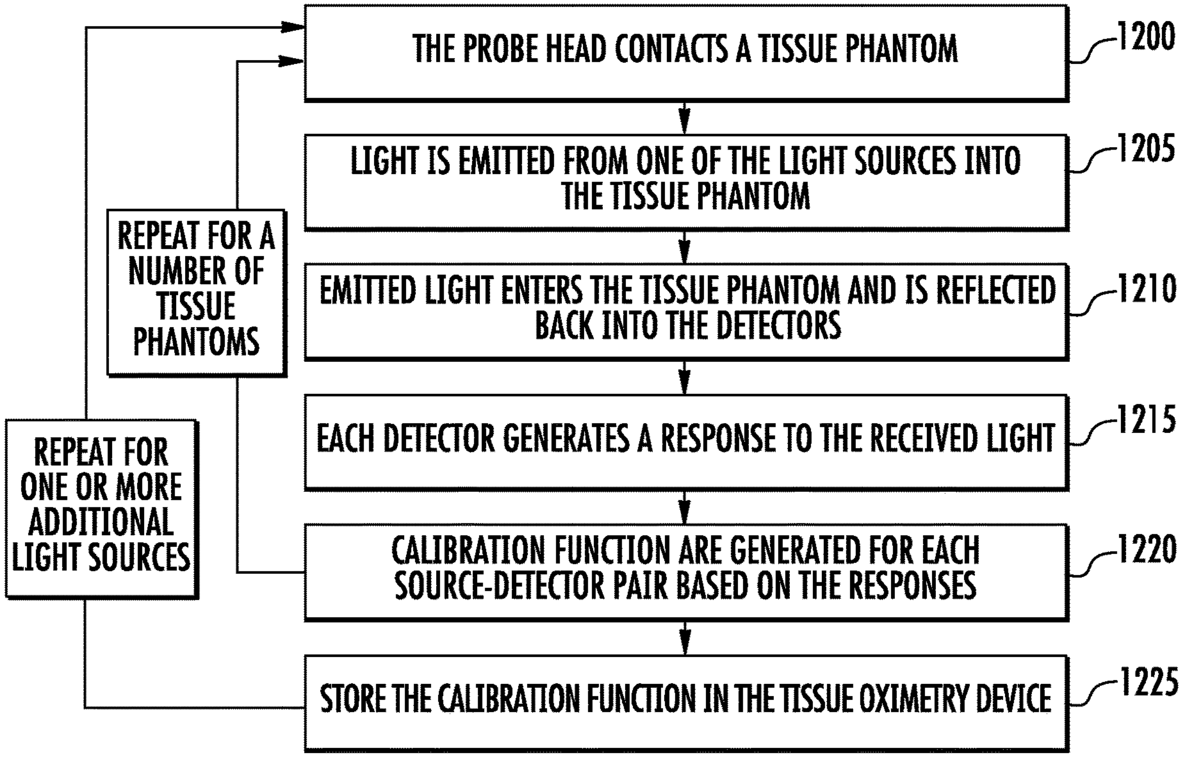
FIG. 12 is a high-level flow diagram of a method for calibrating each source-detector pair according to one embodiment.

FIG. 12 is a high-level flow diagram of a method for calibrating each source-detector pair according to one embodiment. The high-level flow diagram represents one example embodiment. Steps can be added to, removed from, or combined in the high-level flow diagram without deviating from the scope of the embodiment.

At 1200, probe tip 300 contacts a tissue phantom, which has homogeneous optical properties. Light is emitted from one or more of the lighting elements 152, step 1205, into the tissue phantom and at least some of the light is reflected back by the tissue phantom. Each light detector 170 receives a portion of the light reflected from the tissue phantom, step 1210, and each light detector generates reflectance data (i.e., a response) for the portion of reflected light received, step 1215. The reflectance data for light detectors 170 may not match a reflectance curve for the tissue phantom (i.e., can be offset from the reflectance curve). If the reflectance data generated by light detectors 170 does not match the reflectance curve for the tissue phantom, the light detectors may have an intrinsic gain or loss, or the light sources may have more or less power than simulated. The reflectance data generated can be used by one or more of sensor subsystem 110, acquisition module 115, and measurement module 120 to generate a set of calibration functions so that the raw reflectance data matches the reflectance curve for the tissue phantom, step 1220. Raw reflectance data includes the reflectance data generated and output by the light detectors prior to being utilized for determining the optical properties for the tissue and before being utilized for determining oxygen saturation for the tissue.

Steps 1200 to 1220 can be repeated for one or more tissue phantoms. The calibration function for each source-detector pair for each tissue phantom should generally be the same. However, if there is a deviation between the calibration functions for a given source-detector pair for a number of tissue phantoms, then the factors within the calibration function for the given source-detector can be averaged. Each of the calibration functions generated (including averaged functions) is stored in memory device 205, step 1225.

Steps 1200 to 1225 can be repeated for each of the lighting element 152 in each of the light sources 150*a* and 150*b*. If steps 1200 to 1225 are repeated for each of lighting elements 152 in each of the light sources 150*a* and 150*b*, for example, then a number of calibration functions can be stored in memory device 205 for each light detector 170, and each of the stored calibration functions for each light detector is associated with one of the lighting elements 152. That is, each source-detector pair has a calibration function specifically for the source-detector pair.

For example, light detector 170*a* may have a first calibration function stored for light emitted from a first lighting element 152 in light source 150*a*, a second calibration function for a second lighting element 152 in light source 150*a*, a third calibration function for a third lighting element 152 in light source 150*a*, a fourth calibration function for a fourth lighting element 152 in light source 150*a*, and the like if light source 150*a* includes more lighting elements 152. Further, light detector 170*a* may also have a fifth calibration function stored for light emitted from a first lighting element 152 in light source 150*b*, a second calibration function for a second lighting element 152 in light source 150*b*, a third calibration function for a third lighting element 152 in light source 150*b*, a fourth calibration function for a fourth lighting element 152 in light source 150*b*, and the like if light source 150*b* includes more lighting elements 152.

Because a calibration function is stored for each source-detector pair, the calibration functions (e.g., eight calibration functions) for each light detector provide calibration not only for variations in the light detectors but also for variations in the lighting elements 152 of the light sources 150. For example, the intrinsic gain or loss for a light detector should not vary when receiving light from lighting elements 152 in light source 150*a* or 150*b*. If the calibration functions differ for a light detector when receiving reflected light for different lighting elements, the difference in the reflectance data for a given tissue phantom is attributable to differences in the intensity of light emitted by the lighting elements. The calibration functions can be applied to reflectance data that is generated by light detectors 170 when tissue oximetry device 100 is used for oxygen saturation measurement in real tissue, for example, so that any intrinsic gains or losses of the light detectors 170, and any difference in the intensity of light from lighting elements 152, can be compensated for. Specifically, the calibration functions are applied on a source-detector pair basis for the raw reflectance data generated by the detectors.

As described briefly above, a central light source 150*c* can be substantially equidistant (e.g., +/−10 microns) from each of light detectors 170 such that the light detectors can be relatively easily calibrated using homogeneous tissue phantoms. The term "homogeneity" used with respect to a tissue phantom refers to the optical properties of a tissue phantom being substantially constant throughout the volume of the tissue phantom. For example, the absorption coefficient $\mu_a$ and the reduced scattering coefficient $\mu_s'$ of a tissue phantom can be referred to as being homogeneous (i.e., substantially constant) throughout the tissue phantom. This is in contrast to real tissue, which exhibits anisotropic optical properties stemming from the intrinsic alignment of collagen fibers and other biological factors as well as the spatial variances, which may stem from differing degrees of tissue components and oxygen saturation.

Figure 13:
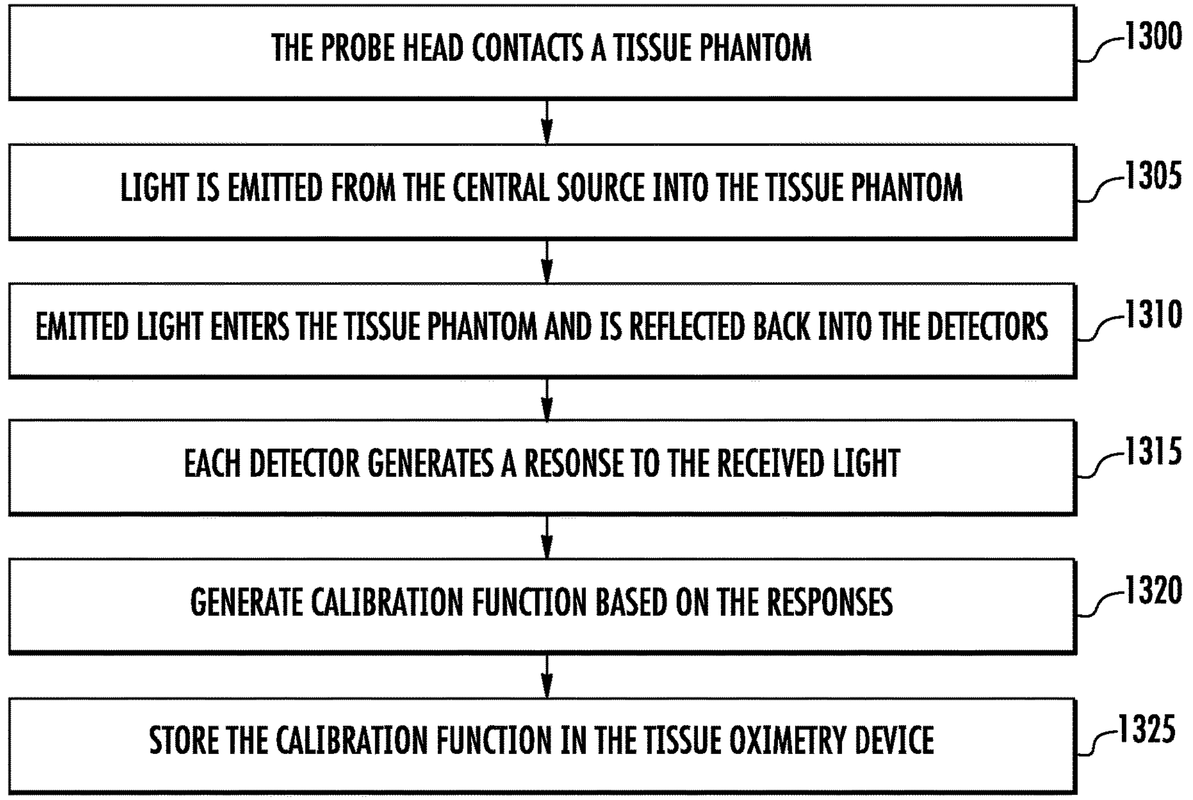
FIG. 13 is a high-level flow diagram of a method for calibrating the light detectors according to one embodiment.

FIG. 13 is a high-level flow diagram of a method for calibrating light detectors 170 according to one embodiment. The high-level flow diagram represents one example embodiment. Steps can be added to, removed from, or combined in the high-level flow diagram without deviating from the scope of the embodiment.

At 1300, probe tip 300 contacts a tissue phantom, which has homogeneous optical properties. Light (e.g., near infrared light) is emitted from central light source 120*c*, step 1305, into the tissue phantom and at least some of the light is reflected back by the tissue phantom. Each light detector 170 receives the light reflected from the tissue phantom, step 1210, and each light detector generates a response to the reflected light, step 1315. Each light detector 170 should receive the same amount of reflected light due to the homogeneity of the tissue phantom. Any differences between light detector responses can therefore be attributed to physical differences between the light detectors. For example, one or more of the light detectors may have an intrinsic gain or an intrinsic loss.

The responses from light detectors 170 are used by one or more of sensor subsystem 110, acquisition module 115, and measurement module 120 to generate calibration functions for the light detectors, where the calibration functions can be used by one or more of sensor subsystem 110, acquisition module 115, and measurement module 120 to flatten the raw reflectance data (i.e., the responses) generated by the light detectors to a single value, step 1320. The calibration functions or the responses, or both, used for generating the calibration functions can be saved, e.g., in memory device 205, step 1325. The calibration functions can be applied to the raw reflectance data that are generated by light detectors 170 when tissue oximetry device 100 is used to measure oxygen saturation levels in real tissue so that any intrinsic gains or losses of the light detectors can be compensated for.

Figure 14:
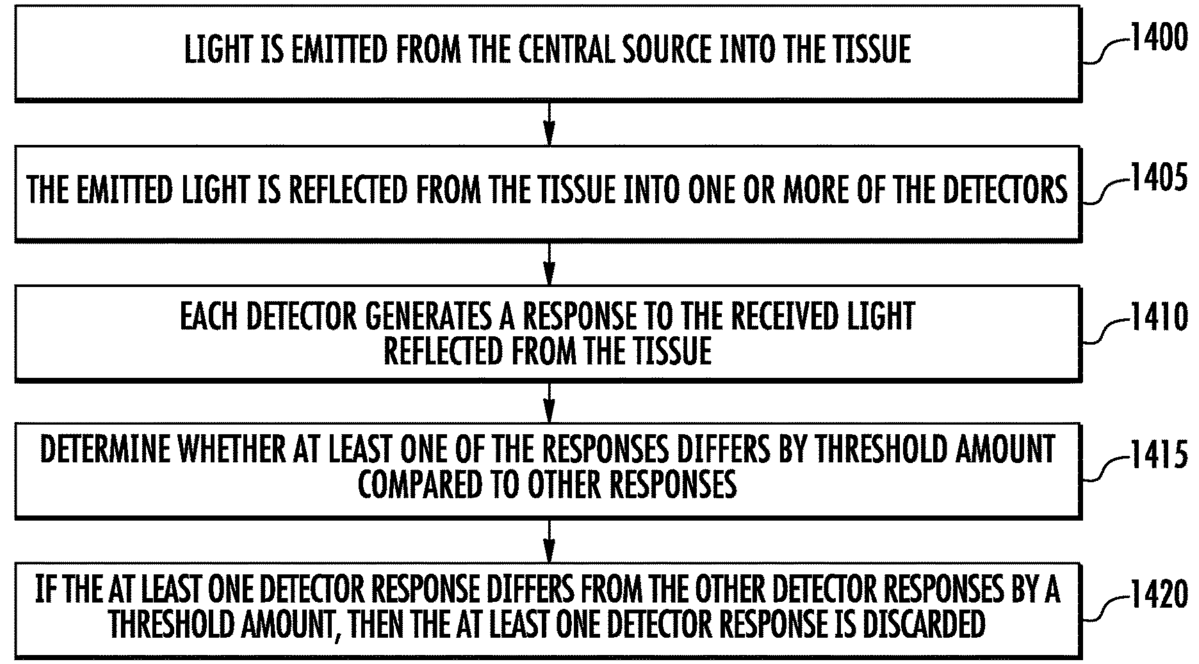
FIG. 14 is a high-level flow diagram of a method for detecting anomalies during use of the tissue oximetry device according to one embodiment.

FIG. 14 is a high-level flow diagram of a method for detecting anomalies during use of tissue oximetry device 100 according to one embodiment. The high-level flow diagram represents one example embodiment. Steps can be added to, removed from, or combined in the high-level flow diagram without deviating from the scope of the embodiment.

Tissue oximetry device 100 may employ the method to detect anomalies such as significant, spatially congruous inhomogeneities in real tissue. Such an inhomogeneity can indicate the presence of a mole or type of tissue that does not contribute relevant information regarding the oxygenated hemoglobin and deoxygenated hemoglobin concentrations in a tissue flap, for example. The inhomogeneity could also indicate that part of the probe has gone beyond the edge of a wound or is covered by blood.

At 1400, light (e.g., near infrared light) is emitted from central light source 120*c* into tissue, and the light is reflected by the tissue into one or more of light detectors 170, step 1405. Each light detector 170 generates a detector response to the received light, step 1410. If one or more detectors lose contact with the tissue, then these detectors may generate a detector response, but the detector response might not be to light emitted from central light source 120*c*. Tissue oximetry device 100 may determine whether the difference in the light detected (i.e., detector response) by at least one of the light detectors differs by a threshold amount compared to light detected by one or more of the other light detectors, step 1415.

If the detector responses to light emitted from central light source 120*c* differ between the light detectors by the threshold amount (i.e., to a greater degree than predicted by ordinary tissue anisotropy), then the detector responses from the at least one light detector in the clear minority of detector responses (i.e., detector response differs by at least the threshold amount) can be discarded, step 1420, and not used to calculate oxygen hemoglobin and deoxygenated hemoglobin concentrations. The at least one light detector in the clear minority can be assumed to have been positioned in contact with a mole, blood, or other or to have lost contact with the tissue.

According to one alternative, if the detector responses generated by a significant number (e.g., four) of light detectors 170 differ significantly (e.g., by the threshold amount) from one another but there is no clear majority of detector responses, then one or both of acquisition module 115 and measurement module 120 may disregard all of the detector responses and may indicate (e.g., on display 125) that accurate oxygen saturation cannot be determined for that currently probed region of tissue. The steps of the method can be repeated substantially continuously as tissue oximetry device 100 measures oxygen saturation in tissue. It is noted that central light source 120*c* might not otherwise be used for obtaining contributive data for a reflectance curve used for determining oxygen saturation.

Self-Correction of Data During Oxygen Saturation Detection

Figure 15:
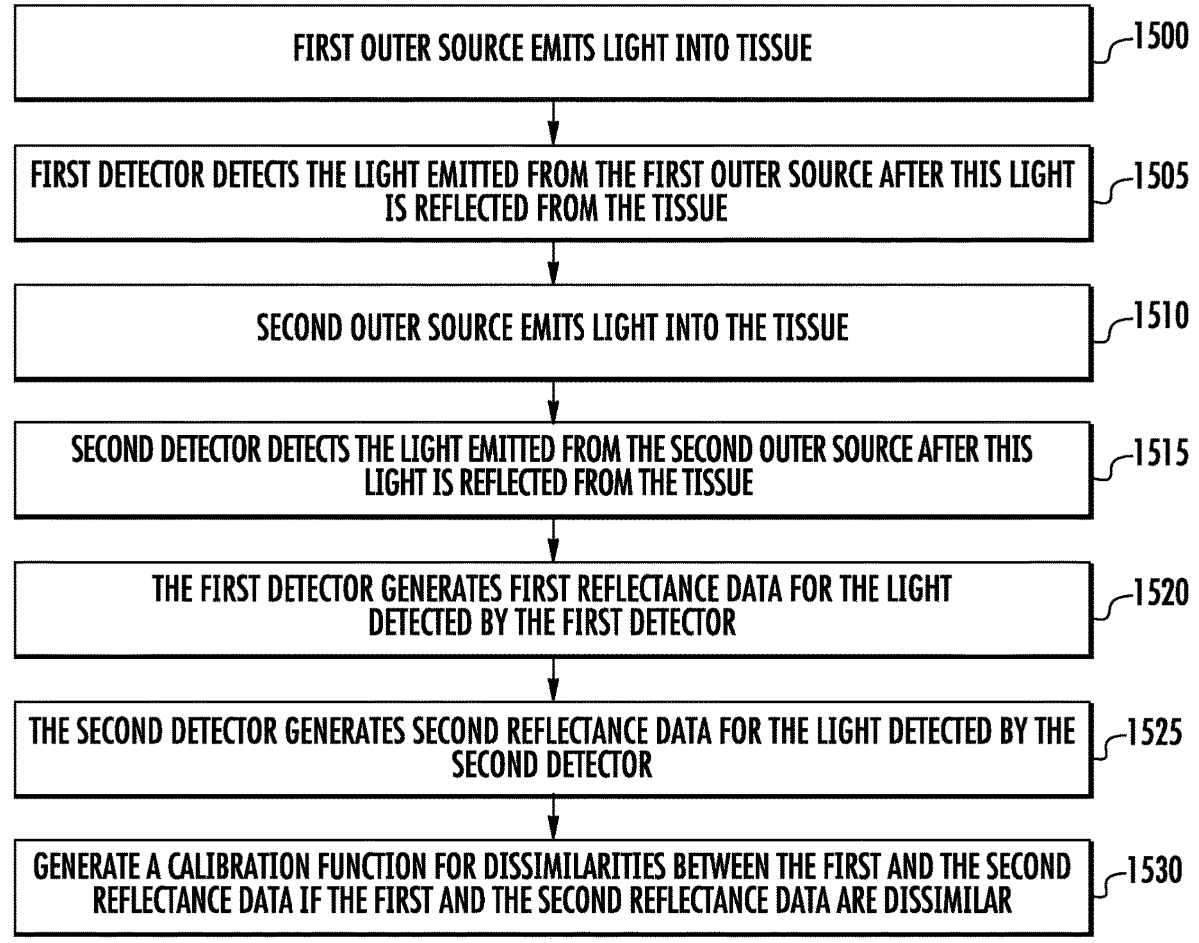
FIG. 15 is a high-level flow diagram of a method for calibrating the amount of light emitted by the light sources.

FIG. 15 is a high-level flow diagram of a method for calibrating the amount of light emitted by light sources 150*a* and 150*b* during oxygen saturation measurements on tissue or with a tissue phantom. The high-level flow diagram represents one example embodiment. Steps can be added to, removed from, or combined in the high-level flow diagram without deviating from the scope of the embodiment.

As described above, the shortest source-to-detector distances D2 and D3 can be intentionally matched for the two outer light sources 150*a* and 150*b* and the longest source-to-detector distances D4 and D5 may also intentionally be matched for these light sources. With the shortest source-to-detector distances matched, when outer source 150*a* emits light, step 1500, of a given wavelength into tissue and light detector 170*e* detects this light reflected from the tissue, step 1505, and when light source 150*b* emits light into the tissue, step 1510, and detector 170*a* detects this light reflected from the tissue, step 1515, the reflectance data generated by light detectors 170*a* and 170*e*, steps 1520 and 1525, respectively, should substantially match. That is, the amount of light detected by light detectors 170*a* and 170*e* should substantially match.

Further, with the longest source-to-detector distances matched, when outer source 150*a* emits light of a given wavelength into tissue and light detector 170*a* detects this light reflected from the tissue, and when light source 150*b* emits light into the tissue and detector 170*e* detects this light reflected from the tissue, the reflectance data generated by light detectors 170*a* and 170*e* should also substantially match. If these pairs of reflectance data do not match, then the source power of light sources 150*a* and 150*b* and the amount of light emitted by these outer sources may also be mismatched.

According to one embodiment, the tissue oximetry device uses these pairs of reflectance data (if mismatched) generated by light detectors 170*a* and 170*e* to correct the reflectance data generated by all of the detectors and to correct the oxygen saturation analysis performed by the device. More specifically, a calibration function, step 1530, for the reflectance data (due to a source power difference between light sources 150*a* and 150*b*) can be determined from the difference between the absolute reflectance detected by light detectors 170*a* and 170*e*. This calibration function can be applied to the raw reflectance data generated by each light detector 170 to compensate for the difference in the amount of light emitted by light sources 150*a* and 150*b*. Specifically, two sets of reflectance data points that are offset from each other can be brought onto a single reflectance curve by applying the generated function to the reflectance data generated by each light detector 170 thereby generating relatively more accurate oxygen saturation data.

Tissue oximetry device 100 may substantially continuously monitor and compare the reflectance data generated by light detectors 170*a* and 170*e* to determine whether differences in the amount of light emitted from the light sources 150*a* and 150*b* occurs. Using the differences (if present), the reflectance data for each of detectors 170 can be substantially continuously corrected by tissue oximetry device 100 during oxygen saturation measurements. According to one alternative embodiment, the calibration of light sources 150*a* and 150*b* is performed once and the generated function is stored for later use while making oxygen saturation measurements.

According to one alternative, additional or alternative source-to-detector distances can be matched for generating a function for the reflectance data due to source power difference between light sources 150*a* and 150*b* (i.e., calibrating light sources 150*a* and 150*b*). That is, the shortest or longest source-to-detector distances (or a combination of these) are not required for calibrating light sources 150*a* and 150*b* and for correcting the reflectance data. Furthermore, while using two or more pairs of matched source-to-detector distances may increase the reliability or accuracy of the source calibration, a single matched pair of source-to-detector distances can be used for calibrating light sources 150*a* and 150*b*.

If a single matched pair of source-to-detector distances (e.g., D2 and D3) is used to calibrate light sources 150*a* and 150*b* and for correcting the reflectance data, then the signal-to-noise ratio of the reflectance data can be relevant for selecting the particular source-to-detector distance to match. If minimal to low noise is present, then matching the longest source-to-detector distances may provide the most robust source calibration. However, noise may increase as the square root of the magnitude of a reflectance data measurement, and therefore can be significantly larger for longer source-to-detector distances. In this case, matching the shortest or relatively short source-to-detector distances may provide a more robust calibration of the outer sources and the reflectance data.

According to another alternative embodiment, all of the source-to-detector distances for light sources 150*a* and 150*b*, and the light detectors 170*a*-170*h* are matched providing four matched source-to-detector distances. Matching four source-to-detector distances for light sources 150*a* and 150*b* allows for the generation of two reflectance data sets for each outer source, which can be compared to verify accuracy of the reflection data. The geometrical incorporation of fast and robust calibration, self-correction, and accurate data collection and processing methods limits fluctuations and inaccuracy seen in saturation measurements made by the intra-operative probes considered to be prior art. The previously discussed calibration, self-correction, and other features can lead to fast, accurate tissue oximetry devices, which should be desirable to plastic surgeons involved in implant-based breast reconstruction and others concerned with detecting tissue regions in danger of necrosis in surgical environments.

Light Waveform

Figure 16:
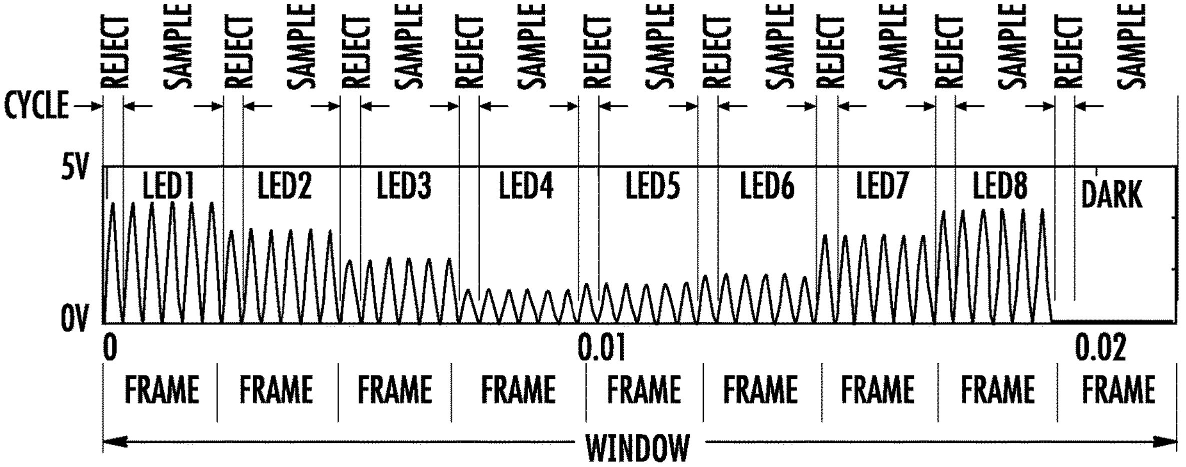
FIG. 16 is a simplified schematic of light generated by the lighting elements (e.g., eight LEDs) in one of the light sources.

FIG. 16 is a simplified schematic of a control signal that can be supplied to lighting elements 152 (e.g., eight LEDs) in light sources 150*a*. Specifically, FIG. 16 represents the control signal and may represent the intensity of the light generated by the lighting elements in one of the light sources at a given time. The pattern of the control signal and of the light generation shown in FIG. 16 can be sequentially repeated by the light sources. In one embodiment, one lighting element 152 at any given time receives the control signal and generates and emits light based on receipt of the control signal. That is, the lighting elements in a light source may sequentially receive the control signal. For example, a first lighting element (e.g., LED1) in one of the light sources can receive the control signal and generate and emit light, then a second lighting element (e.g., LED2) in the light source can generate and emit light, then a third lighting element (e.g., LED3) in the light source can receive the control signal and generate and emit light, and so forth until an eighth lighting element (e.g., LED8) receives the control signal for generating and emitting light.

The control signal can be a time varying control signal, such as a sinusoidal control signal, that sinusoidally modulates the intensity of light generated by each lighting element. In one specific embodiment, the frequency of the control signal 2.5 kilohertz frequency.

The control signal is supplied to each lighting element for a given time (sometimes referred to herein as a frame) which may include a number of cycles (e.g., 6 cycles) of the control signal. The control signal can cycle the lighting elements from zero light generation and emission to a peak light generation and emission. In one embodiment, the sinusoidal control signal that is supplied to each of the lighting elements starts at zero (e.g., zero current and voltage) so that the ramp up of light generated by a lighting elements starts at zero light generation and rises with the sinusoidal waveform.

In one embodiment, each of the light detectors 170 samples the light reflected from tissue 140 at a given frequency, such as at 100 sample per cycles (i.e., sampling can be at 250 kilohertz) of the control signal. In some embodiments, light detectors 170 do not sample light reflected from tissue during the first cycle of a frame where the lighting elements can be warming up to a stable operating temperature, or acquisition module 115, measurement module 120 or both can ignore reflectance data generated for the first cycle. Other methods can also be used for disregarding the first cycle of light generation by the lighting elements.

After all of the lighting elements 152 in a light source 150 generate and emit light for a number of consecutive frames (e.g., eights frames for eight LEDs), then none of the lighting elements in the light source can generate and emit light for the time period of a frame (e.g., e.g., 6 cycles of the control signal). Thereafter, another of the light sources can generate and emit light as described above. To briefly summarize, as referred to herein, a cycle is one cycle of the control signal; a frame comprises multiple cycles (e.g., 6 cycles); a window comprises a sequence of frames (e.g., one frame for each LED and one dark frame); and a measurement uses multiple windows over which the reflectance data is generated and processed by measurement module 120.

According to one particular embodiment, the lighting elements 152 of each light source 150*a* and 150*b* are configured to generate and emit light at wavelengths of 760 nanometers (e.g., +/−10 nanometers), 810 nanometers (e.g., +/−10 nanometers), 845 nanometers (e.g., +/−20 nanometers), and 895 nanometers (e.g., +/−10 nanometers). Lighting elements 152 can sequentially generate and emit light in the above order (e.g., 760 nanometers, 810 nanometers, 845 nanometers, and 895 nanometers) for each of the light sources 150*a* and 150*b*. While the light sources 150*a* and 150*b* are described herein as including four lighting elements 152, alternative embodiments of light sources 150*a* and 150*b* include more or fewer lighting elements.

For example, according to an embodiment where each of the light sources 150*a* and 150*b* include two lighting elements, these lighting elements in each light source can generate and emit the wavelengths of approximately 760 nanometers (e.g., +/−10 nanometers), and 850 nanometers (e.g., +/−20 nanometers). According to an embodiment where each light source 150 includes three lighting elements, the lighting elements can be configured to generate and emit wavelengths of approximately 760 nanometers (e.g., +/−10 nanometers), 810 nanometers (e.g., +/−10 nanometers), and 850 nanometers (e.g., +/−20 nanometers). According to another embodiment, where each light source 150 includes four lighting elements, the lighting elements can be configured to emit wavelengths of approximately 760 nanometers (e.g., +/−10 nanometers), 810 nanometers (e.g., +/−10 nanometers), 850 nanometers (e.g., +/−20 nanometers), and 900 nanometers (e.g., +/−20 nanometers). Additional and/or alternative wavelengths can be utilized by tissue oximetry device 100.

Use of the described wavelengths by tissue oximetry device 100 tends to decrease the fraction of emitted light that can be absorbed by methylene blue, gentian violet, and povidone-iodine (PVPI), and thereby increases the fraction of light that can be scattered or absorbed by intrinsic tissue elements and generates accurate reflectance data. The dyes are often used by in the operating room to mark tissue. Accurate reflectance data is necessary in order to extract the optical properties of tissue from which the concentrations of oxygenated and deoxygenated hemoglobin can be derived.

For the foregoing described wavelengths, tissue scattering is relatively low and light penetrates farther into tissue than shorter wavelengths. Further, the foregoing described wavelengths are on both sides of an oxygenated-deoxygenated hemoglobin spectral crossing point called an isosbestic point, which is 810 nanometers for hemoglobin. As such, when one chromophore (e.g., oxygenated hemoglobin) has high absorption, the other chromophore (e.g., deoxygenated hemoglobin) then has low absorption and vice versa. The tissue oximetry device's utilization of wavelengths surrounding the isosbestic point provides for relatively improved statistics for oxygen saturation determinations.

In at least one of the previous described embodiments, tissue oximetry device 100 utilizes a wavelength at approximately the isosbestic point, at 810 nanometers. At the isosbestic point the absorption of the 810 nanometer wavelength for oxygenated hemoglobin and deoxygenated hemoglobin are equivalent and therefore provides a stable reference point in the reflectance data generated by light detectors 170. Relatively longer wavelengths, such as the 900 nanometer wavelength of at least one embodiment allows for distinguishing between the absorption curves for deoxygenated hemoglobin from the absorption curve for melanin.

Use of Wavelengths for Optical Probing.

Oxygenated and deoxygenated hemoglobin concentrations, from which oxygen saturation can be calculated, can be related to the absorption coefficient μa of a region of tissue for a given wavelength of light. In some cases, a simple relationship is used for calculation where the absorption coefficient is assumed to depend only on the concentrations of oxygenated and deoxygenated hemoglobin. However, melanin and water present in tissue can also absorb incident light so this simple relationship can be insufficient for highly accurate concentration calculations, as absorption from water and melanin can be incorrectly attributed to oxygenated or deoxygenated hemoglobin. A relationship between the absorption coefficient and the concentrations of oxygenated hemoglobin (HbO2), deoxygenated hemoglobin (Hb), water (H2O), and melanin (mel) can be:

$$\mu_a=2.303(\varepsilon_{HbO2}[HbO2]+\varepsilon_{Hb}[Hb]+\varepsilon_{H2O}[H2O]+\varepsilon_{mel}[mel])$$

where $\varepsilon_{species}$ denotes the molar absorptivity of a given species and bracketed quantities indicate concentration values.

The shape of a reflectance curve (generated by plotting the intensity of diffusely reflected or re-emitted light) can be analyzed to obtain the absorption and scattering coefficients for a given region of tissue. There are four unknown concentrations (i.e., [HbO2], [Hb], [H2O], and [mel]) in the above relationship that correspond to the absorption coefficient. Once the absorption coefficient is determined for a given wavelength, the relationship becomes an equation of four unknown variables. However, since the concentrations of oxygenated and deoxygenated hemoglobin, water, and melanin should not vary considerably over the course of a probe measurement, probing the tissue with four different wavelength emitted by the wavelength sources can provide four values for μa, which can be used to determine the four relevant concentrations in the expression for μa. That is, a system of four equations with four unknown variables can be solved, as is well understood. From the determined concentrations of oxygenated hemoglobins [HbO2] and deoxygenated hemoglobins [Hb], the oxygen saturation of tissue can be determined.

According to the embodiment where three wavelengths are emitted by the wavelength sources, the contributions from water, melanin, and other light absorbers can be combined into a single term and expressed as:

$$\mu_a=2.303(\varepsilon_{HbO2}[HbO2]+\varepsilon_{Hb}[Hb]+\varepsilon_{H2O,mel}[H2O, mel])$$

If three absorption coefficients $\mu_a$ are determined for the three wavelengths, then the three relevant concentrations for [HbO2], [Hb], and [H2O, mel]) can be determined, and the oxygen saturation can again be determined from the determined concentrations of oxygenated and deoxygenated hemoglobins. The absorption coefficients can be determined from the reflectance data by a variety of methods, such as fitting the reflectance data to one or more predetermined reflectance curves, where each predetermined reflectance curve represents a unique absorption coefficient. The absorption coefficients may alternatively be determined by vector multiplication with the net analyte signal, which is described in U.S. Pat. No. 6,597,931, titled "System and Method for Absolute Oxygen Saturation," and is incorporated by reference.

Monte Carlo Simulation

According to a specific embodiment, memory device 205 stores a number of Monte Carlo-simulated reflectance curves 600 ("simulated reflectance curves"), which can be generated by a computer for subsequent storage in the memory device. Each of the simulated reflectance curves 600 represents a simulation of light (e.g., visible or near infrared light) emitted from one or more simulated light sources into simulated tissue and reflected from the simulated tissue into one or more simulated detectors. Simulated reflectance curves 600 are for a specific configuration of simulated light sources and simulated detectors, such as the configuration of lighting elements 152 in light sources 150 and detectors 170 in probe tip 300. Therefore, simulated reflectance curves 600 model light emitted from, and collected by, tissue oximetry device 100.

Further, each of the simulated reflectance curves 600 represents a unique real tissue condition, such as specific tissue absorption and tissue scattering values that relate to particular concentrations of tissue chromophores and densities of tissue scatterers. The number of simulated reflectance curves stored in memory device 205 can be relatively large and can represent nearly all, if not all, practical combinations of optical properties and tissue properties that can be present in real tissue that is analyzed for viability by tissue oximetry device 100. While memory device 205 is described herein as storing Monte Carlo-simulated reflectance curves, memory device 205 may store simulated reflectance curves generated by methods other than Monte Carlo methods, such as using the diffusion approximation.

Figure 17:
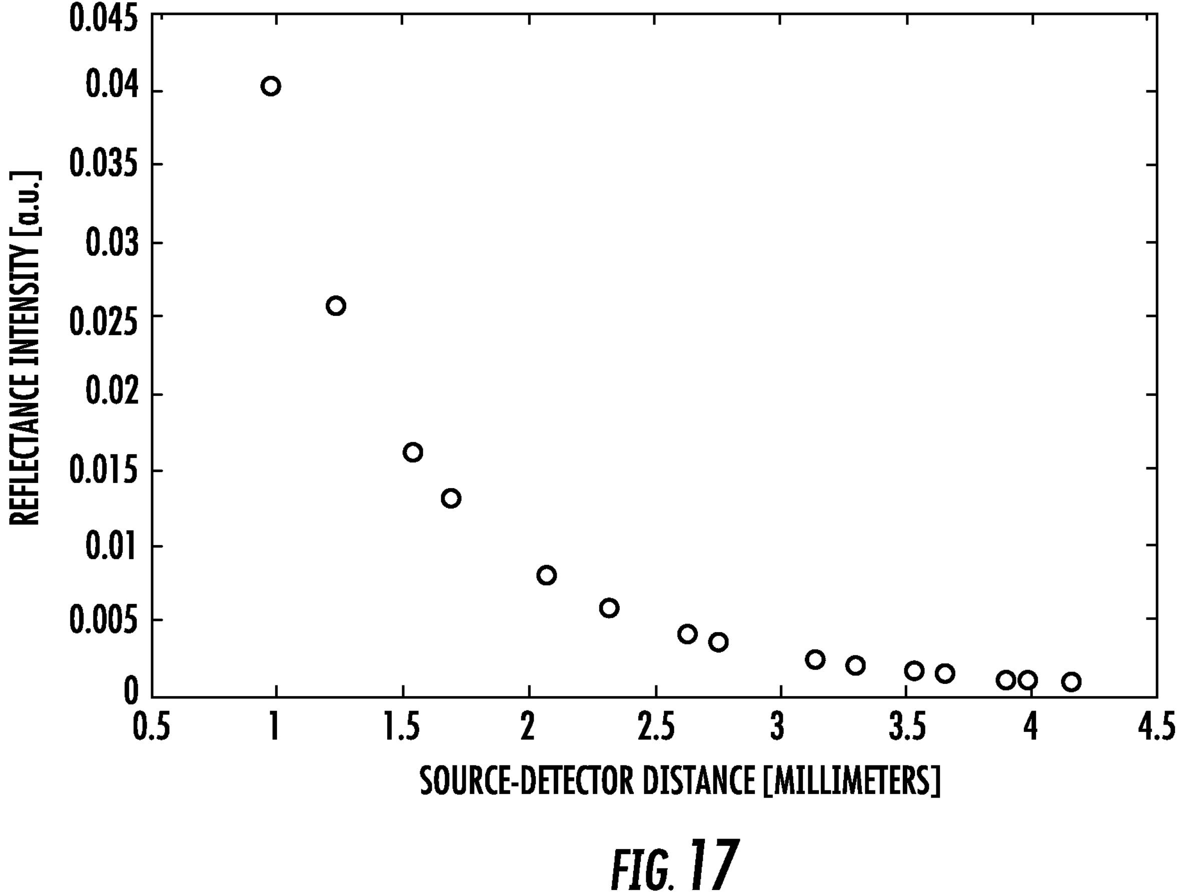
FIG. 17 is an example graph of a reflectance curve, which can be for a specific configuration of the light sources and the light detectors.

FIG. 17 is an example graph of a reflectance curve, which can be for a specific configuration of light sources 150 and light detectors 170, such as one of the configurations light sources and detectors of probe tip 300, or the like. The horizontal axis of the graph represents the distances between light sources 150 and light detectors 170 (i.e., source-detector distances). If the distances between light sources 150 and light detectors 170 are appropriately chosen, and the simulated reflectance curve is a simulation for light sources 150 and light detectors 170, then the lateral spacings between the data points in the simulated reflectance curve will be relatively uniform. Such relatively uniform spacings can be seen in the simulated reflectance curve in FIG. 17. The vertical axis of the graph represents the simulated reflectance of light that reflects from tissue and is detected by light detectors 170. As shown by the simulated reflectance curve, the reflectance that reaches light detectors 170 varies with the distance between light sources 150 and light detectors 170.

According to one implementation, memory device 205 stores a select number of points for each of the simulated reflectance curves 600 and might not store the entirety of the simulated reflectance curves. The number of points stored for each of simulated reflectance curves 600 may match the number of source-detector pairs. For example, if probe tip 300 includes two light sources 150*a* and 150*b* and includes eight light detectors 170*a*-170*h*, then tissue oximetry probe 100 includes sixteen source-detector pairs, and memory device 205 may thus store sixteen select data points for each of the simulated reflectance curves, where stored data points are for the specific source-detectors distances (i.e., distances between the light sources and the light detectors).

Thus, the simulated reflectance curve database stored in memory device 205 can be sized 16 by 3 by 5850 where sixteen points are stored per curve for three different wavelengths that can be generated and emitted by each light source 150 and wherein there are a total of 5850 curves spanning the optical property ranges. Alternatively, the simulated reflectance curve database that is stored in memory device 205 can be sized 16 by 4 by 5850, wherein sixteen points are stored per curve for four different wavelengths that can be generated and emitted by each light source and wherein there are a total of 5850 curves spanning the optical property ranges. The 5850 curves originate, for example, from a matrix of 39 absorption coefficients $\mu'_s$ values and 150 absorption coefficient $\mu_a$ values. The $\mu'_s$ values can range from 5:5:24 centimeter$^{-1}$($\mu'_s$ depends on the value for g). The $\mu_a$ values can range from 0.01:0.01:1.5 centimeter$^{-1}$. It will be understood that the above described ranges are example ranges and the number source-detectors pairs, the number of wavelengths generated by each light source, and the number of simulated reflectance curves can be smaller or larger.

Tissue Analysis

Figure 18A:
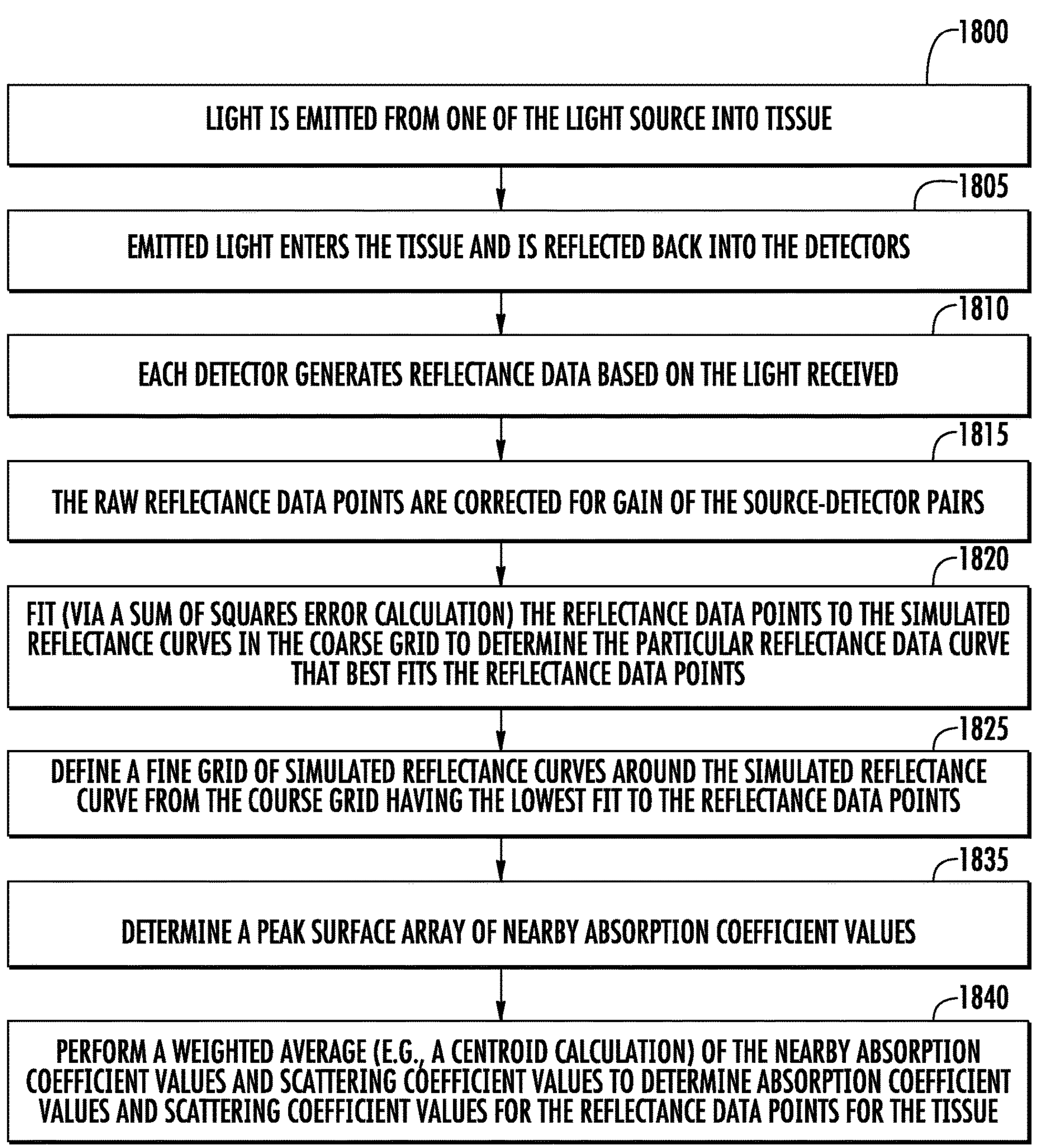
FIG. 18A is a high-level flow diagram of a method for determining the optical properties of tissue.

FIG. 18A is a high-level flow diagram of a method for determining the optical properties of tissue (e.g., real tissue) by tissue oximetry device 100 where the tissue oximetry device uses reflectance data and simulated reflectance curves 600 to determine the optical properties. The optical properties may include the absorption coefficient $\mu_a$ and the scattering coefficients $\mu_s$ of the tissue. A further method for conversion of the absorption coefficient $\mu_a$ and the scattering coefficients of the tissue $\mu_s$ to oxygen saturation values for tissue is described in further detail below. The high-level flow diagram represents one example embodiment. Steps can be added to, removed from, or combined in the high-level flow diagram without deviating from the scope of the embodiment.

At 1800, tissue oximetry device 100 emits light from one of the light sources 150, such as light source 150*a* into tissue. Probe tip 300 is generally in contact with the tissue when the light is emitted from the light source. After the emitted light reflects from the tissue, light detectors 170 detect a portion of this light, step 1805, and generate reflectance data points for the tissue, step 1810. Steps 1800, 1805, and 1810 can be repeated for multiple wavelengths of light and for one or more other light sources, such as light source 150*b*. The reflectance data points for a single wavelength can include sixteen reflectance data points if, for example, probe tip 300 provides sixteen source-detectors distances. The reflectance data points are sometimes referred to as an N-vector of the reflectance data points.

At 1815, the reflectance data points (e.g., raw reflectance data points) are corrected for gain of the source-detector pairs. During calibration of the source-detector pairs (described above), gain corrections are generated for the source-detector pairs and are stored in memory device 205.

At 1820, control processor 200 of measurement module 120 fits (e.g., via a sum of squares error calculation) the reflectance data points to the simulated reflectance curves 600 to determine the particular reflectance data curve that best fits (i.e., has the lowest fit error) the reflectance data points. According to one specific implementation, a relatively small set of simulated reflectance curves that are a “coarse” grid of the database of the simulated reflectance curves is selected and utilized for fitting step 1820. For example, given 39 scattering coefficient $\mu'_s$ values and 150 absorption coefficient $\mu_a$ values, a coarse grid of simulated reflectance curves can be determined by control processor 200 by taking every 5th scattering coefficient $\mu'_s$ value and every 8th absorption coefficients $\mu_a$ for a total of 40 simulated reflectance curves in the coarse grid. It will be understood that the foregoing specific values are for an example embodiment and that coarse grids of other sizes can be utilized by control processor 200. The result from fitting the reflectance data points to the coarse grid is a coordinate in the coarse grid $(\mu_a, \mu'_s)_{coarse}$ of the best fitting simulated reflectance curve.

At 1825, the particular simulated reflectance curve from the coarse grid having the lowest fit error is utilized by control processor 200 to define a “fine” grid of simulated reflectance curves where the simulated reflectance curves in the fine grid are around the simulated reflectance curve from the coarse grid having the lowest fit error.

That is, the fine grid is a defined size, with the lowest error simulated reflectance curve from the coarse grid defining the center of the fine grid. The fine grid may have the same number of simulated reflectance curves as the coarse grid or it may have more or fewer simulated reflectance curves. The fine grid is substantially fine so as to provide a sufficient number of points to determine a peak surface array of nearby absorption coefficient $\mu_a$ values and scattering coefficient $\mu'_s$ values, step 1830, in the fine grid. Specifically, a threshold can be set by control processor 200 utilizing the lowest error value from the coarse grid plus a specified offset. The positions of the scattering coefficient $\mu'_s$ and the absorption coefficient $\mu_a$ on the fine grid that have errors below the threshold may all be identified for use in determining the peak surface array for further determining the scattering coefficient $\mu'_s$ and the absorption coefficient $\mu_a$ for the reflectance data. Specifically, an error fit is made for the peak to determine the absorption coefficient $\mu_a$ and the scattering coefficient $\mu'_s$ values at the peak. A weighted average (e.g., a centroid calculation) of the absorption coefficient $\mu_a$ and the scattering coefficient $\mu'_s$ values at the peak can be utilized by the tissue oximetry device for the determination of the absorption coefficient $\mu_a$ and the scattering coefficient $\mu'_s$ values for the reflectance data points for the tissue, step 1840.

Weights for the absorption coefficient $\mu_a$ and the scattering coefficient $\mu'_s$ values for the weighted average can be determined by control processor 200 as the threshold minus the fine grid error. Because points on the fine grid are selected with errors below the threshold, this gives positive weights. The weighted calculation of the weighted average (e.g., centroid calculation) renders the predicted scattering coefficient $\mu'_s$ and absorption coefficient $\mu_a$ (i.e., $(\mu_a,\mu'_s)$fine) for the reflectance data points for the tissue. Other methods can be utilized by the tissue oximetry device, such as fitting with one or more of a variety of non-linear least squares to determine the true minimum error peak for the scattering coefficient $\mu'_s$.

According to one implementation, control processor 200 calculates the log of the reflectance data points and the simulated reflectance curves, and divides each log by the square root of the source-detector distances (e.g., in centimeters). These log values divided by the square root of the of the source-detector distances can be utilized by control processor 200 for the reflectance data points and the simulated reflectance curves in the foregoing described steps (e.g., steps 1815, 1820, 1825, and 1830) to improve the fit of the reflectance data points to the simulated reflectance curves.

According to another implementation, the offset is set essentially to zero, which effectively gives an offset of the difference between the coarse grid minimum and the fine grid minimum. The method described above with respect to FIG. 18A relies on minimum fit error from the coarse grid, so the true minimum error on the fine grid is typically lower. Ideally, the threshold is determined from the lowest error on the fine grid, which would typically require additional computation by the processor.

Figure 18B:
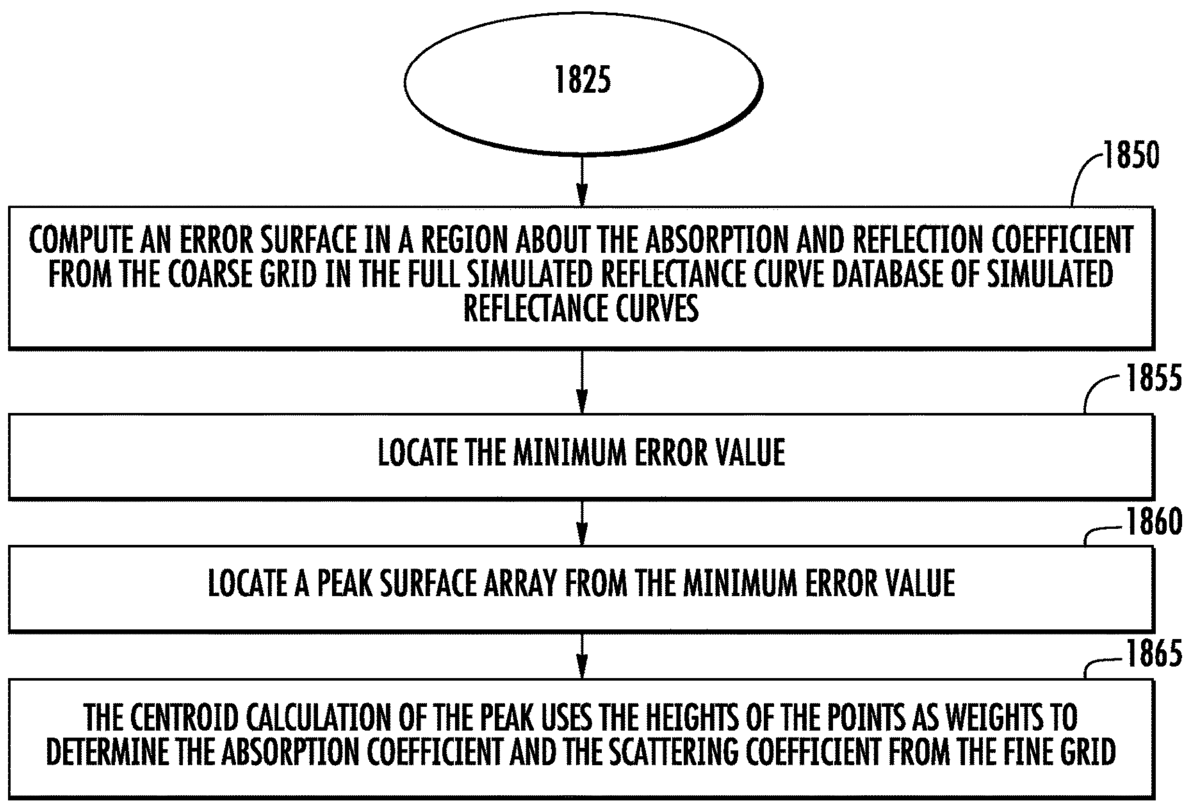
FIG. 18B is a high-level flow diagram of a method for finding the particular simulated reflectance curve that best fits the reflectance data points in the fine grid according to one implementation.

The following is a further detailed description for finding the particular simulated reflectance curve that best fits the reflectance data points in the fine grid according to one implementation. FIG. 18B is a high-level flow diagram of a method for finding the particular simulated reflectance curve that best fits the reflectance data points in the fine grid according to one implementation. The high-level flow diagram represents one example embodiment. Steps can be added to, removed from, or combined in the high-level flow diagram without deviating from the scope of the embodiment.

Subsequent to determining the particular simulated reflectance curve $(\mu_a,\mu'_s)_{coarse}$ from the coarse grid that best fits the reflectance data points at step 1825, control processor 200 computes an error surface in a region about $(\mu_a,\mu'_s)_{coarse}$ in the full simulated reflectance curve database (i.e., 16 by 4 by 5850 $(\mu_a,\mu'_s)$ database) of simulated reflectance curves, step 1850. The error surface is denoted as: $err(\mu_a,\mu'_s)$. Thereafter, control processor 200 locates the minimum error value in $err(\mu_a,\mu'_s)$, which is referred to as $err_{min}$, step 1855. Control processor 200 then generates a peak surface array from $err(\mu_a,\mu'_s)$ that is denoted by $pksurf(\mu_a,\mu'_s)=k+err_{min}-err(\mu_a,\mu'_s)$ if the peak surface is greater than zero, or $pksurf(\mu_a,\mu'_s)=k+err_{min}-err(\mu_a,\mu'_s)=0$ if the peak surface is less than or equal to zero, step 1860. In the expression k is chosen from a peak at the minimum point of $err(\mu_a,\mu'_s)$ with a width above zero of approximately ten elements. The center-of-mass (i.e., the centroid calculation) of the peak in $pksurf(\mu_a,\mu'_s)$ uses the heights of the points as weights, step 1865. The position of the center-of-mass is the interpolated result for the absorption coefficient $\mu_a$ and the scattering coefficient $\mu'_s$ for the reflectance data points for the tissue The method described above with respect to FIGS. 18A and 18B for determining the absorption coefficient $\mu_a$ and the scattering coefficient $\mu'_s$ for reflectance data points for tissue can be repeated for each of the wavelengths (e.g., 3 or 4 wavelengths) generated by each of light sources 150.

Oxygen Saturation Determination

According to a first implementation, control processor 200 determines the oxygen saturation for tissue that is probed by tissue oximetry device 100 by utilizing the absorption coefficients $\mu_a$ (e.g., 3 or 4 absorption coefficients $\mu_a$) that are determined (as described above) for the 3 or 4 wavelengths of light that are generated by each light source 120. According to a first implementation, a look-up table of oxygen saturation values is generated for finding the best fit of the absorption coefficients $\mu_a$ to the oxygen saturation. The look-up table can be generated by assuming a range of likely total hemoglobin, melanin, and oxygen saturation values and calculating $\mu_a$ for each of these scenarios. Then, the absorption coefficient $\mu_a$ points are converted to a unit vector by dividing by a norm of the unit vector to reduce systematic error and only depend on relative shape of curve. Then the unit vector is compared to the look-up table to find the best fit, which gives the oxygen saturation.

According to a second implementation, control processor 200 determines the oxygen saturation for the tissue by calculating the net analyte signal (NAS) of deoxygenated hemoglobin and oxygenated hemoglobin. The NAS is defined as the portion of the spectrum that is orthogonal to the other spectral components in the system. For example, the NAS of deoxygenated hemoglobin is the portion of the spectrum that is orthogonal to oxygenated hemoglobin spectrum and melanin spectrum. The concentrations of deoxygenated and oxygenated hemoglobin can then be calculated by vector multiplying the respective NAS and dividing by a norm of the NAS squared. Oxygen saturation is then readily calculated as the concentration of oxygenated hemoglobin divided by the sum of oxygenated hemoglobin and deoxygenated hemoglobin. Anal. Chem. 58:1167-1172 (1986) by Lorber is incorporated by reference herein and provides a framework for a further detailed understanding of the second implementation for determining the oxygen saturation for the tissue.

According to one embodiment of tissue oximetry device 100, the reflectance data is generated by light detectors 170 at 30 Hertz, and oxygen saturation values are calculated at approximately 3 Hertz. A running average of determined oxygen saturation values (e.g., at least three oxygen saturation values) can be displayed on display 125, which can have an update rate of 1 Hertz.

Optical Properties

As described briefly above, each simulated reflectance curve 600 that is stored in memory device 205 represents unique optical properties of tissue. More specifically, the unique shapes of the simulated reflectance curves, for a given wavelength, represent unique values of the optical properties of tissue, namely the scattering coefficient ($\mu_s$), the absorption coefficient ($\mu_a$), the anisotropy of the tissue (g), and index of refraction of the tissue.

The reflectance detected by light detectors 170 for relatively small source-to-detector distances is primarily dependent on the reduced scattering coefficient, $\mu'_s$. The reduced scattering coefficient is a "lumped" property that incorporates the scattering coefficient $\mu_s$ and the anisotropy g of the tissue where $\mu'_s=\mu_s(1-g)$, and is used to describe the diffusion of photons in a random walk of many steps of size of $1/\mu'_s$ where each step involves isotropic scattering. Such a description is equivalent to a description of photon movement using many small steps $1/\mu_s$ which each involve only a partial deflection angle if there are many scattering events before an absorption event, i.e., $\mu_a \ll \mu'_s$.

In contrast, the reflectance that is detected by light detectors 170 for relatively large source-detector distances is primarily dependent on the effective absorption coefficient $\mu_{eff}$, which is defined as $\sqrt{3\mu_a(\mu_a+\mu'_s)}$, which is a function of both $\mu_a$ and $\mu'_s$.

Thus, by measuring reflectance at relatively small source-detector distances (e.g., the distance between light source 150*a* and light detector 170*e* and the distance between light source 120*b* and light detector 170*a*) and relatively large source-detector distances (e.g., the distance between light source 150*a* and detector 170*a* and the distance between light source 120*b* and detector 170*e*), both $\mu_a$ and $\mu'_s$ can be independently determined from one another. The optical properties of the tissue can in turn provide sufficient information for the calculation of oxygenated hemoglobin and deoxygenated hemoglobin concentrations and hence the oxygen saturation of the tissue.

Iterative Fit for Data Collection Optimization.

Figure 19:
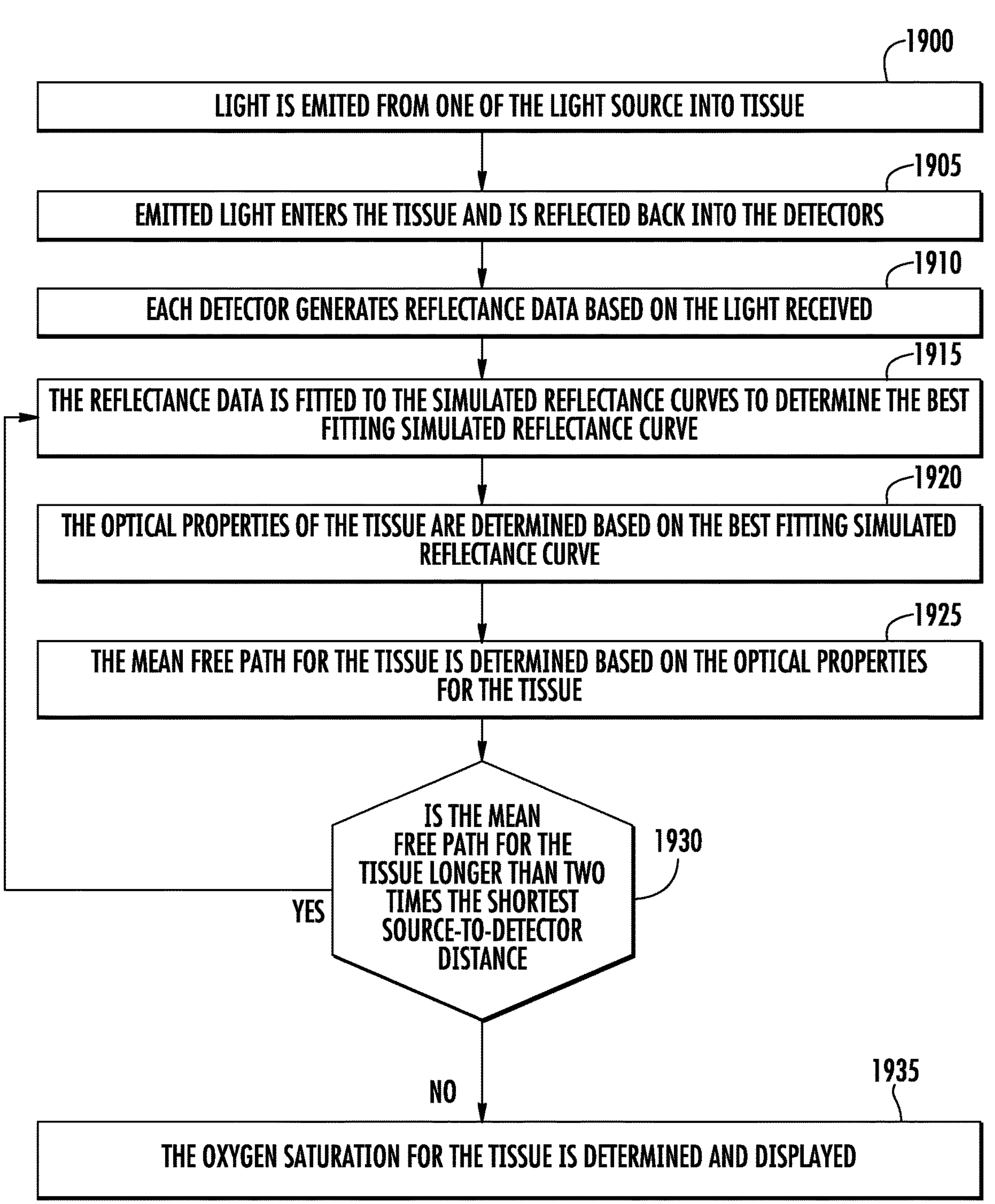
FIG. 19 is a high-level flow diagram of another method for determining the optical properties of tissue by the tissue oximetry device.

FIG. 19 is a high-level flow diagram of another method for determining the optical properties of tissue by tissue oximetry device 100. The high-level flow diagram represents one example embodiment. Steps can be added to, removed from, or combined in the high-level flow diagram without deviating from the scope of the embodiment.

At 1900, tissue oximetry device 100 emits light from one of the light sources, such as light source 150*a* into tissue. After the emitted light reflects from the tissue, light detectors 170 detect the light, step 1905, and generate reflectance data for the tissue, step 1910. Steps 1900, 1905, and 1910 can be repeated for multiple wavelengths of light and for one or more other light sources, such as light source 150*b*. At 1915, control processor 200 fits the reflectance data to simulated reflectance curves 600 and determines the simulated reflectance curve to which the reflectance data has the best fit. Thereafter, control processor 200 determines the optical properties (e.g., $\mu_a$, and $\mu'_s$) for the tissue based on the optical properties of the simulated reflectance curve that best fits the reflectance data, step 1920.

At 1925 control processor 200 determines the mean free path of the light in the tissue from the optical properties (e.g., $mfp=1/(\mu_a+\mu'_s)$ determined at step 1920. Specifically, the mean free path can be determined from the optical properties obtained from a cumulative reflectance curve that includes the reflectance data for all of the source-detector pairs (e.g., pair 1: light source 150*a*—detector 170*e*; pair 2: light source 150*a*—detector 170*f*; pair 3: light source 150*a*—detector 170*g*; pair 4: light source 150*a*—detector 170*h*; pair 5: light source 150*a*—detector 170*a*; pair 6: light source 150*a*—detector 170*b*; pair 7: light source 150*a*—detector 170*c*; pair 8: light source 150*a*—detector 170*d*; . . . pair 9: light source 150*b*—detector 170*e*, pair 10: light source 150*b*—detector 170*f* . . . and others.).

At 1930, control processor 200 determines whether the mean free path calculated for a given region of the tissue is longer than two times the shortest source-to-detector distance (e.g., the distance between light source 150*a* and detector 170*e*, and the distance between light source 150*b* and detector 170*a*). If the mean free path is longer than two times the shortest source-to-detector distance, then the collected reflectance data is re-fitted to the simulated reflectance curves (i.e., reanalyzed) without utilizing the reflectance data collected from the detectors for the source-to-detector pairs (e.g., pair 1: light source 150*a*—detector 170*e* and pair 9 light source 150*b*—detector 170*a*) having the shortest source-to-detector distance. For example, steps 1915-1930 are repeated without use of the reflectance data from detector 170*e* with light source 150*a* acting as the source for detector 170*e*, and without use of the reflectance data from detector 170*a* with light source 150*b* acting as the source for detector 170*a*. The process of calculating the mean free path and discarding the reflectance data for one or more source-detector pairs can be repeated until no source-detector pairs that contribute reflectance data to the fit have a source-to-detector distance shorter than one half of the calculated mean free path. Thereafter, oxygen saturation is determined from the best fitting simulated reflectance curve and reported by tissue oximetry device 110, such as on display 125, step 1935.

Light that is emitted from one of the light sources 150 into tissue and that travels less than half of the mean free path is substantially nondiffusely reflected. The re-emission distance for this light is strongly dependent on the tissue phase function and the local tissue composition. Therefore, using the reflectance data for this light tends to result in a less accurate determination of the optical properties and tissue properties as compared with the reflectance data for light that has undergone multiple scattering events.

Data Weighting

Light detectors 170 that are positioned at increasing distances from light sources 150 receive decreasing amounts of reflectance from tissue. Therefore, the reflectance data generated by light detectors 170 having relatively short source-to-detector distances (e.g., source-to-detector distances less than or equal to the average distance between the light sources and the light detectors) tends to exhibit intrinsically lower noise compared to reflectance data generated by detectors having relatively long source-to-detector distances (e.g., source-to-detector distances greater than the average distance).

Fit algorithms may therefore preferentially fit the simulated reflectance curves to the reflectance data that is generated by light detectors 170 having relatively short source-to-detectors distances (e.g., source-to-detector distances less than or equal to the average distance between the light sources and the light detectors) more tightly than reflectance data that is generated by light detectors having relatively long source-to-detector distances (e.g., source-to-detector distances greater than the average distance). For relatively accurate determination of the optical properties from the reflectance data, this distance-proportional skew can be undesirable and can be corrected by weighting the reflectance data as described immediately below.

Figure 20:
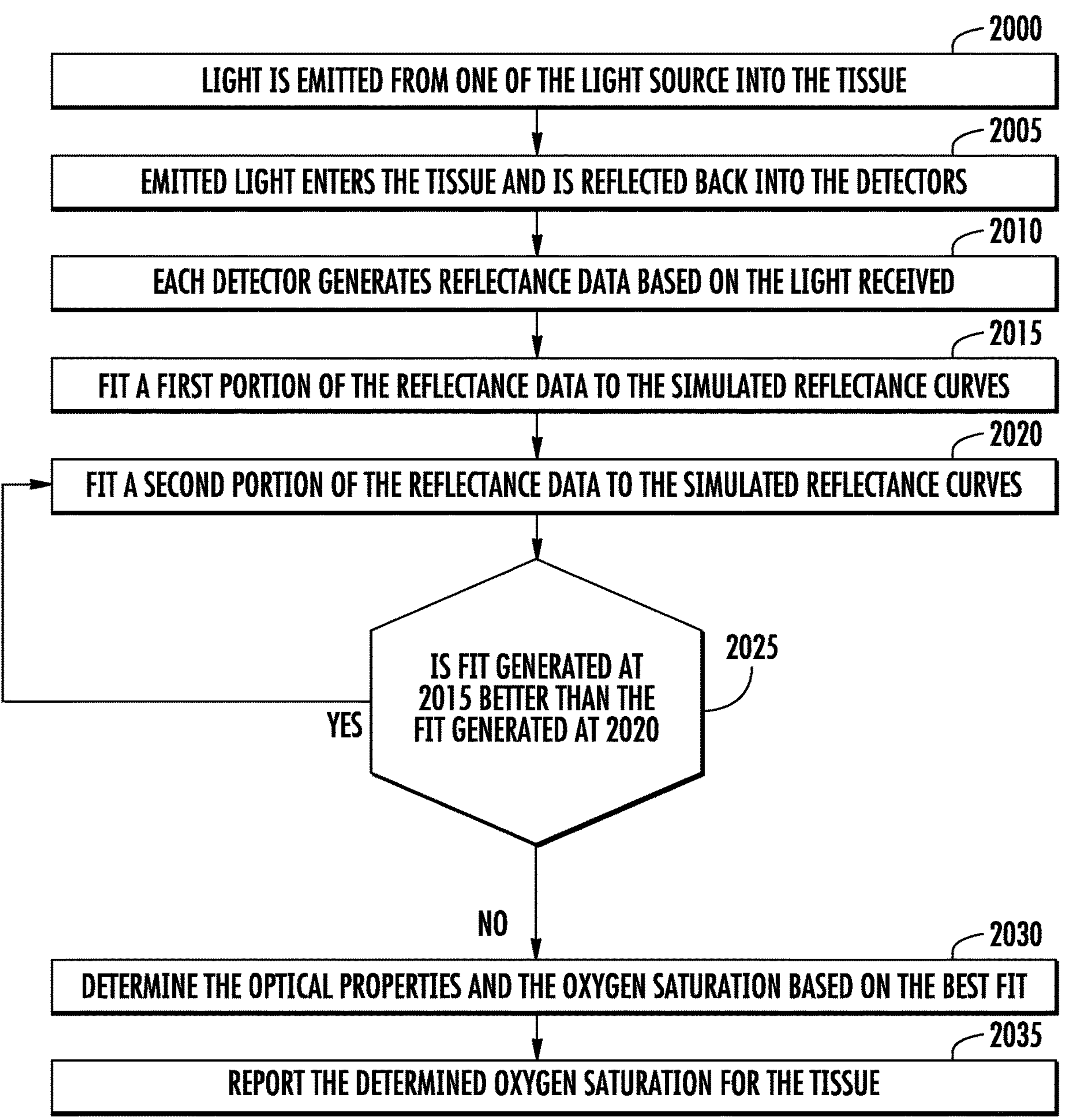
FIG. 20 is a high-level flow diagram of a method for weighting reflectance data generated by select light detectors.

FIG. 20 is a high-level flow diagram of a method for weighting reflectance data generated by select light detectors 170. The high-level flow diagram represents one example embodiment. Steps can be added to, removed from, or combined in the high-level flow diagram without deviating from the scope of the embodiment.

At 2000, tissue oximetry device 100 emits light from one of the light sources, such as light source 150*a* into tissue. After the emitted light reflects from the tissue, light detectors 170 detect the light, step 2005, and generate reflectance data for the tissue, step 2010. Steps 2000, 2005, and 2010 can be repeated for multiple wavelengths of light and for one or more other light sources, such as light source 150*b*. At 2015, control processor 200 fits a first portion of the reflectance data to the simulated reflectance curves.

The first portion of the reflectance data is generated by a first portion of detectors that are less than a threshold distance from the light source. The threshold distance can be the average distances (e.g., approximate mid-range distance) between the light sources and the light detectors. At 2020, reflectance data for a second portion of the reflectance data is fitted to the simulated reflectance curves. The second portion of reflectance data is generated by the first portion of the light detectors and another light detector that is at the next largest source-to-detector distance from the light source compared to the threshold distance. For example, if the first portion of light detectors includes light detectors 170*c*, 170*d*, 170*e*, and 170*f*, then the light detector that is at the next largest source-to-detector distance is detector 170*g* (e.g., closer to light source 150*a* than detector 170*c*, see FIGS. 9A and 9B).

At 2025, the fit generated at step 2015 is compared to the fit generated at step 2020 to determine whether the fit generated at step 2020 is better than the fit generated at 2015. As will be understood by those of skill in the art, a "closeness" of a fit of data to a curve is quantifiable based on a variety of parameters, and the closeness of fits are directly comparable to determine the data having a closer fit (closer fit) to a curve. As will be further understood, a closer fit is sometimes also referred to as a better fit or a tighter fit.

If the fit generated at step 2020 is better than the fit generated at step 2015, then steps 2020 and 2025 are repeated with reflectance data that is generated by light detectors that include an additional light detector (according to the example being considered, light detector 170*c*) that is positioned at a next increased source-to-detector distance from the source. Alternatively, if the fit generated at step 2020 is not better than the fit generated at step 2015, then the reflectance data for light detectors 170 that are positioned at source-to-detector distances that are greater than the threshold distance are not used in the fit. Thereafter, control processor 200 uses the fit generated at 2015 or step 2020 (if better than the fit determined at step 2015) to determine the optical properties and the oxygen saturation of the tissue, step 2030. Thereafter, oxygen saturation is reported by tissue oximetry device 110, such as on display 125, step 2035.

According to an alternative embodiment, if the fit generated at step 2020 is not better than the fit generated at step 2015, then the reflectance data are weighted by a weighting factor for light detectors that have source-to-detector distances that are greater than the threshold distance so that this weighted reflectance data has a decreased influence on the fit. Reflectance data that is not used in a fit can be considered as having a zero weight and can be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the light detectors, and the amount of noise can scale as the square root of the magnitude of the reflectance data.

According to a further embodiment, control processor 200 iteratively weights the reflectance data based on the amount of noise associated with the measurements of the reflectance data. Specifically, the reflectance data generated by light detectors having relatively large source-to-detector distances generally have lower signal-to-noise ratio compared to the reflectance data generated by light detector having relatively short source-to-detector distances. Reducing the weighting of the reflectance data generated by light detectors having relatively large source-to-detector distances allows for this data to influence to the fit less than other reflectance data.

Calibration

According to one embodiment, tissue oximetry device 100 is calibrated utilizing a number (e.g., three to thirty) of tissue phantoms that have known optical properties. Tissue oximetry device 100 can be used to probe the tissue phantoms and collect reflectance data for the tissue phantoms. The reflectance data for each tissue phantom can be fitted to simulated reflectance curves 600. The reflectance data generated for each tissue phantom should fit a simulated reflectance curve, which has the same optical properties as the tissue phantom. If the reflectance data does not fit well to the simulated curve that matches the optical properties of the tissue phantom, then a calibration function can be generated by control processor 200 to improve the fit. One or more of the calibration functions or an average of the calibration functions can be stored in memory device 205. The one or more calibration functions can be applied to reflectance data generated for real tissue that is probed by tissue oximetry device 100 so that the reflectance data for the real tissue will fit to one of the simulated reflectance curves that has optical properties that are a substantially accurate match to the optical properties of the real tissue. Thereafter, the optical properties for the matched simulated reflectance curve can be used to calculate and report the oxygenation saturation of the real tissue.

Pressure Sensor

As described briefly above, probe tip 300 may include at least one pressure sensor 175. Pressure sensor 175 can be located on a face of probe tip 300, between various components of sensor head 250 (e.g., between probe tip 300 and disk shaped end 105*d* of housing 105), between various components of probe tip 300, or the like. Pressure sensor 175 is configured to detect the pressure at which probe tip 300 is pressed against tissue that is being probed. Pressure sensor 175 may detect pressures from about 0 millimeters of mercury to about 100 millimeters of mercury. In other implementations, the pressure sensor can be omitted.

Figure 21:
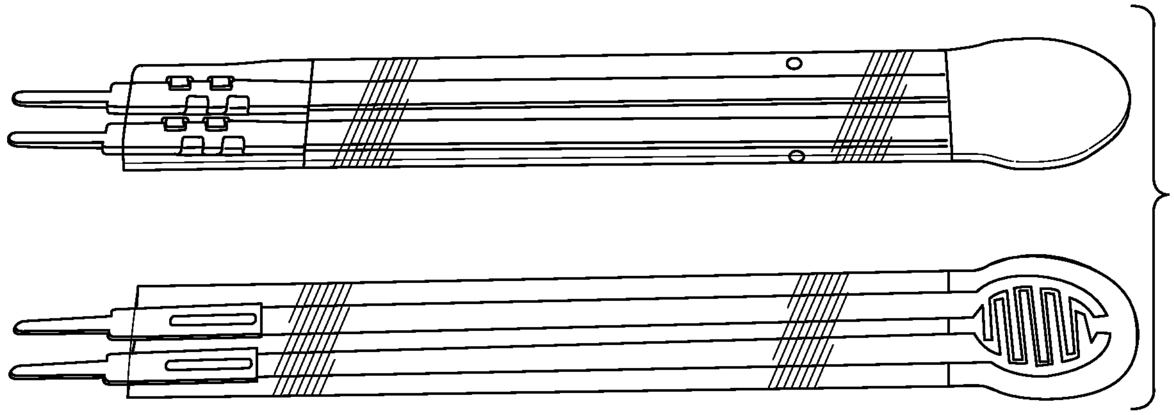
FIG. 21 shows back and front views of a force sensing resistor.

Pressure sensor 175 can be a force sensing resistor (FSR), a piezoelectric pressure sensor, a capacitive pressure sensor, an inductive pressure sensor, a load cell, or the like, or may include one or more of these sensors in combination, such as an FSR and a load cell. According to one specific embodiment, pressure sensor 175 is an FSR produced by Interlink Electronics and is sold under the brand name Standard 400 FSR. FIG. 21 shows back and front views of an FSR that can be used with tissue oximetry device 100. The FSR can be produced by Interlink Electronics and sold under the brand name Standard 400 FSR. The FSR includes a pressure sensing regions and a set of traces in a PCB for transmitting electrical signal from the FSR to acquisition module 115, measurement module 120, or both.

In one implementation, a non-zero preload force is applied to pressure sensor 175 by components of probe tip 130, sensor head 250, housing 105, or a combination of these. Further, acquisition module 115, measurement module 120, or both may perform a tare operation on pressure sensor 175 after tissue oximetry device 100 is turned on. Taring pressure sensor 175 after tissue oximetry device 100 is turned on corrects for pressure changes on the pressure sensor that may have occurred during assembly, shipping, storage, or other causes.

Figure 22A:
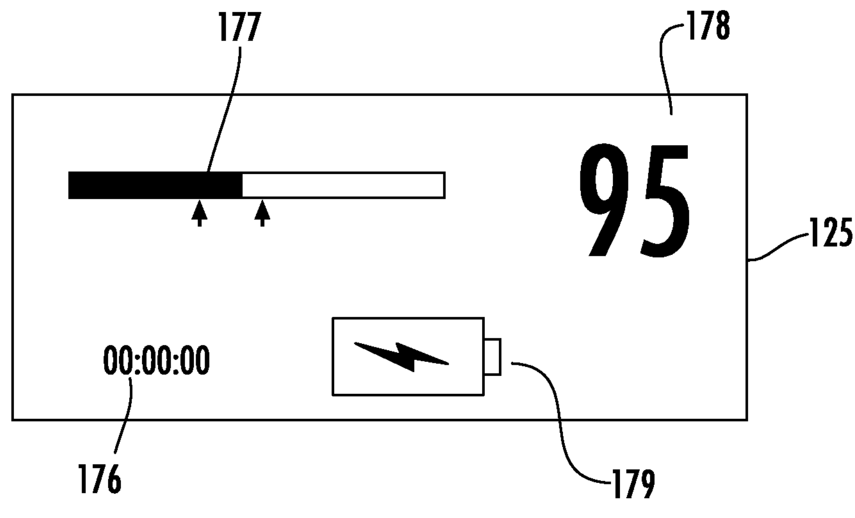
FIGS. 22A and 22B are simplified images of the display.

FIG. 22A is a simplified image of display 125, which can be configured to display a pressure indicator 177 that indicates the amount of pressure sensed by pressure sensor 175. Pressure indicator 177 may include a numerical indicator (now shown), a graphical indictor (shown in FIG. 22A), or both for indicating pressure detected by pressure sensor 175. The numerical indicator may display the detected pressure in millimeters of mercury, pound per square inch, grams per square centimeter, or other units. Alternatively, the numerical indicator may display the force applied by tissue oximetry device 100 on tissue being probed.

In one embodiment, the graphical indicator is a one-dimensional graph, such as a one-dimensional bar graph, a two-dimensional graph, or the like that graphically indicates the detected pressure. For example, if the graphical indicator is a one-dimensional bar graph as shown in FIG. 22A, the percentage of the bar graph filled in (e.g., with a given color) indicates the detected pressure.

The graphical indicator may include additional graphical marks (e.g., arrows shown in FIG. 22A) to indicate that the detected pressure is in an optimal pressure range. For example, the portion of the bar graph between the arrows may indicate the optimal pressure range. Optimal pressure ranges are described in further detail below.

Pressure indicator 177 or a portion thereof can be displayed in a unique manner if the detected pressure is in the optimal pressure range. For example, the numerical indicator and/or the graphical indicator can be displayed in a first color (e.g., red) if the detected pressure is not in the optimal pressure range, and can be displayed in a second color (e.g., green) if the detected pressure is in the optimal pressure range. According to another example, the portion of the one-dimensional bar graph for the optimal pressure range and the graphical marks (e.g., arrows) that indicate the optimal pressure range can be displayed in the second color (e.g., green) to indicate that optimal pressure is detected, and other portions of the one-dimensional bar graph outside of the graphical marks can be displayed in the first color (e.g., red) to indicate that the optimal pressure is not detected.

While display 125 is described herein as being configured to display an indicator 178 for oxygen saturation and an indicator 177 for applied pressure, other display devices can be configured to display these indicators, such as the display of a detached base unit or an external display that is configured to wire or wirelessly communicate with tissue oximetry device 100.

Turning now to the optimal pressure range, the optimal pressure range is a range in which valid oxygen saturation measurements can be made by tissue oximetry device 100. Pressures applied within the optimal pressure range are sufficiently large enough to seal probe tip 300 against tissue being probed so that light from ambient sources does not leak into light detectors 170. Further, pressures applied within the optimal pressure range are also sufficiently small so that blood within tissue being probed is not pressed from the tissue or inhibited from flowing into the tissue so that oxygen saturation measurements are not skewed. More specifically, applied pressures above an upper limit of the optimal pressure range may indicate that the pressure of probe tip 300 on tissue is relatively high and is pressing blood from the tissue such that an oxygen saturation measurement will be adversely affected by these pressures.

The optimal range of applied pressure for probe tip 300 on tissue can be different for different patients. For example, the optimal range of applied pressure can be lower for a patient with diabetes as compared to a normally healthy patient without diabetes. For example, the optimal pressure range for a normally healthy patient can be from about 10 millimeters of mercury to about 30 millimeters of mercury, whereas the optimal pressure range for a patient with diabetes can be from about 5 millimeters of mercury to about 25 millimeters of mercury.

One or more optimal pressure ranges can be empirically predetermined and information for the one or more optimal pressure ranges can be stored in memory device 205. Tissue oximetry device 100 may include one or more of a variety of devices that can be used to select the information for one of the optimal pressure ranges stored in memory device 205. For example, one or more of the input controllers 130 can be configured for switching between the various optimal pressure ranges. Alternatively, display 125 can be a touch screen and can be configured to display one or more display buttons (e.g., a specific example of one of the input controllers 130) where the display buttons can be touched and/or pressed for selecting one of the optimal pressure ranges. Display 125 may also display an indicator for the particular optimal pressure range selected. The indicator for the particular optimal pressure range selected may include a "condition" indicator that indicates the condition (i.e., normal, diabetic, or other conditions) that is associated with the particular optimal pressure range selected.

Display 125 may also display a total time 176 of use of tissue oximetry device 100. The use time can be tracked by measurement module 120 for display on display 125. Display 125 can also display a low battery indicator 179 if the battery power is low. In another alternative, display 125 can display a power meter (not shown) that indicates the charge remaining in batteries 220.

Figure 23:
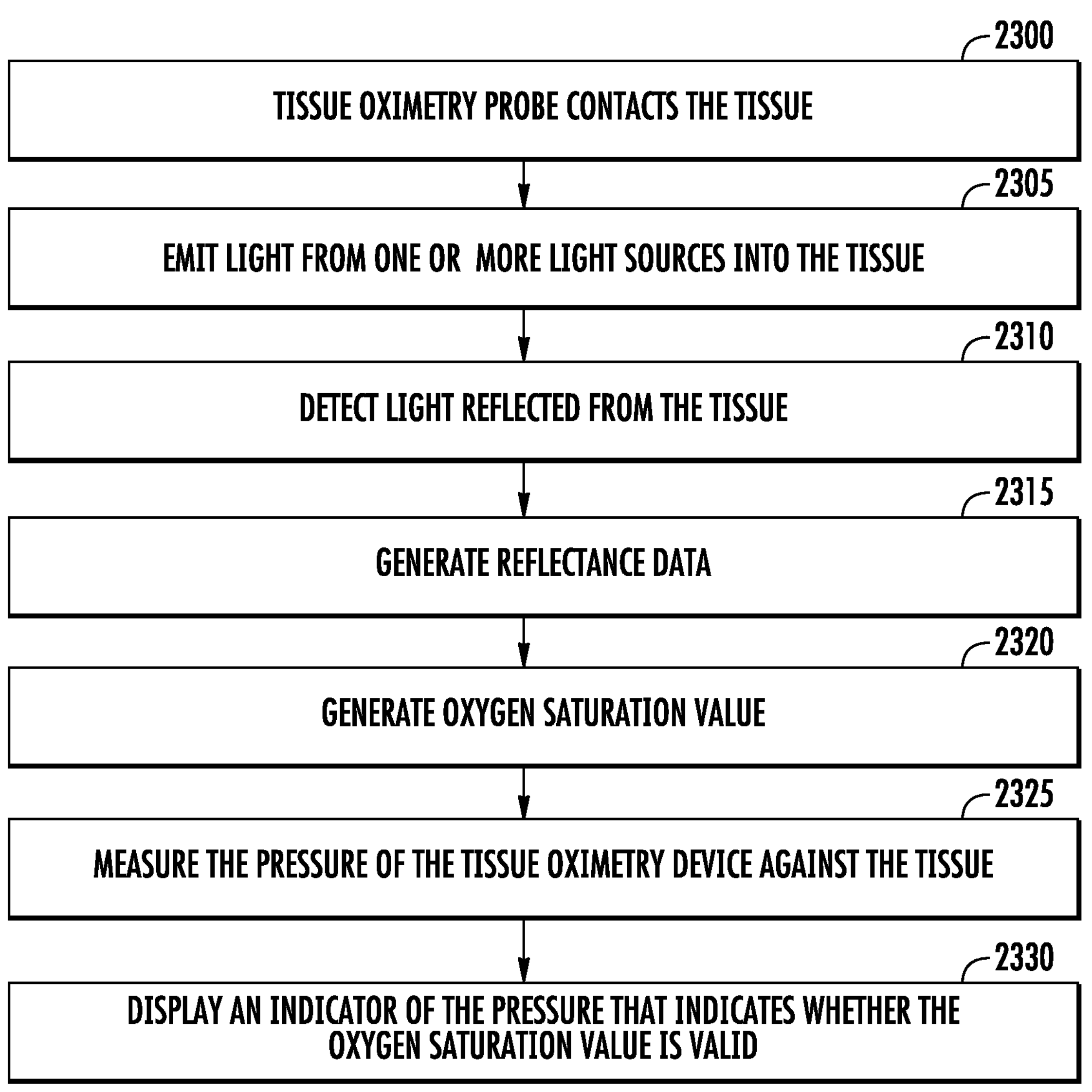
FIG. 23 is a high-level flow diagram of a method for measuring the pressure of the probe tip against tissue being probed.

FIG. 23 is a high-level flow diagram of a method for measuring the pressure of probe tip 300 against tissue being probed and for indicating whether a tissue oximetry measurement of the tissue oximetry device 100 is valid based on the pressure. The high-level flow diagram represents one example embodiment. Steps can be added to, removed from, or combined in the high-level flow diagram without deviating from the scope of the embodiment.

Figure 22B:
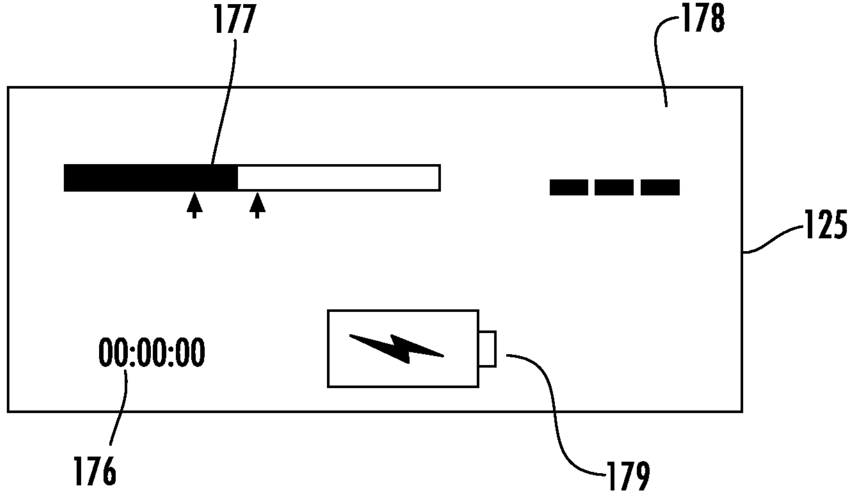

At 2300, probe tip 300 contacts the tissue. Light (e.g., near infrared light) is emitted from one or more of the light sources 150, step 2305, into the tissue and at least some of the light is reflected back by the tissue. Each light detector 170 receives a portion of the light reflected from the tissue, step 2310, and each light detector generates reflectance data (i.e., a response) for the portion of reflected light received, step 2315. At 2320, control processor 200 determines an oxygen saturation value for the tissue based on the reflectance data. At 2325, pressure sensor 175 measures the pressure (or force) of probe tip 300 on the tissue. At 2330, display 125 displays pressure indicator 177 and displays an indicator for the oxygen saturation. Pressure indicator 177 indicates whether the oxygen saturation measured is valid or invalid based on the pressure. For example, pressure indicator 177 can be displayed in the second color (e.g., green) if the pressure is within an optimal pressure range for which valid oxygen saturation measurements can be made, and in the first color (e.g., red) if the pressure is not within the optimal pressure range. While the utilization of color is described for indicating whether the oxygen saturation measurement is valid, other indicators can be used for such indication, such as flashing text or graphics, changed fonts, use of dashed lines for indicator 178 (see FIG. 22B) for the oxygen saturation, or other indications. The mark (e.g., dashed lines) for indicating that a valid oxygen saturation cannot be made, can be displayed for a variety of conditions described herein.

The steps of the pressure-sensing method can be substantially continuously repeated so that a user using tissue oximetry device 100 receives updated feedback (i.e., pressure indicator 177) as the user increases or decreases the pressure applied to the tissue so that a pressure within the optimal pressure range is applied and so that valid tissue oximetry measurements are made.

Tissue Marking

Figure 24:
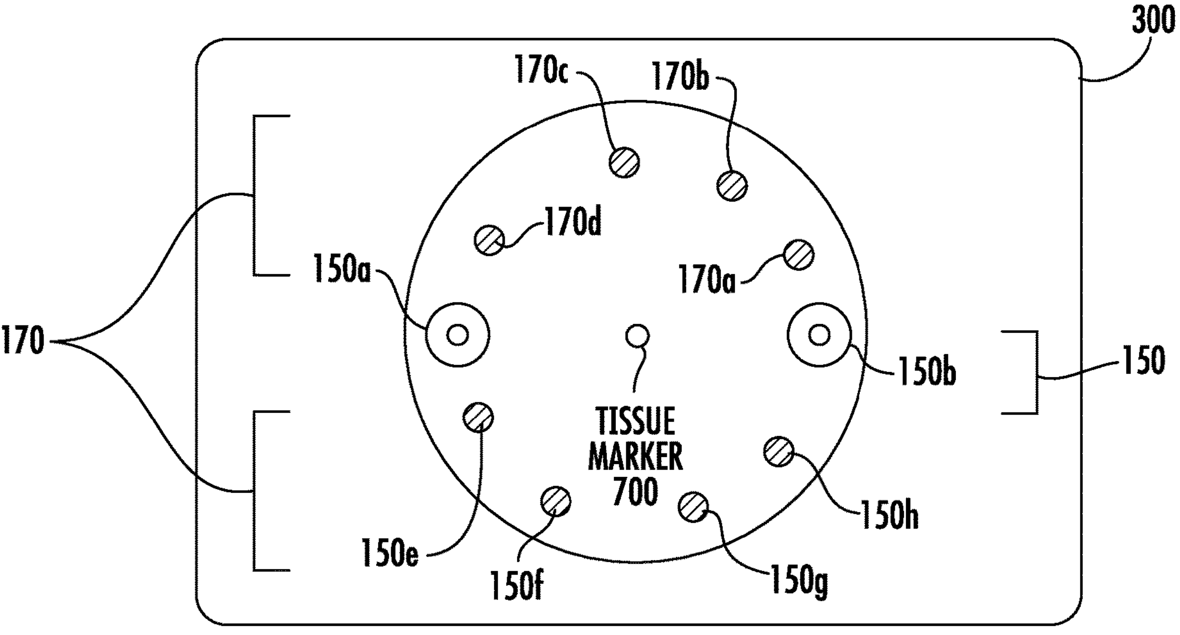
FIG. 24 shows an embodiment of the probe tip where the probe tip 300 includes at least a dispenser portion of a tissue marker.

According to one embodiment, tissue oximetry device 100 includes a tissue marker that is configured to mark tissue. FIG. 24 shows an embodiment of probe tip 300 where the probe tip 300 includes at least a dispenser portion 700 of the tissue marker. The dispenser portion of the tissue marker can be located at a variety positions on the face of probe tip 300. According to one specific embodiment, the dispenser portion is located between light sources 150*a* and 150*b*, and can be located at the approximate center of the circular arrangement of detectors 170. With the dispenser at the approximate center of light sources 150 and detectors 170, a mark made by the dispenser will be substantially at a center of the local tissue region that has been probed by tissue oximetry device 100. With the mark at the center of the probed tissue region, the mark is not displaced from the location on the local tissue region probed.

According to one implementation, the tissue marker includes one or more dispensers that can be located at different positions of probe tip 200. For example, two dispensers can be located "outside" of light sources 150 and light detectors 170. That is, the dispensers can be located at the ends of radii that are longer than the radii of the locations of light sources 150 and detectors 170. Further, the dispensers may lie on a line that passes through the center of the circle of the circular arrangement of light detectors 170.

With the dispensers located along such a line, marks made by these dispensers allow a user to readily identify the region between the marks as the local tissue region that has been probed by tissue oximetry device 100.

While the dispenser is shown in FIG. 24 as being relatively localized devices (e.g., pen, pens, inker, inkers, and the like) that can be configured to mark tissue with relatively small marks (e.g., dots), a dispenser can be an extended device configured to make an extended mark, such as a line. For example, a dispenser can be an extended device configured to mark tissue with a circle or other closed shape, or may mark tissue with an open shape, such as a u-shape, a v-shape, or others.

The dispenser can be fixed within probe tip 300 or can be configured to be lowered when tissue is marked. Various mechanical or electromechanical devices can be utilized by probe tip 300 for lowering the dispenser. Such mechanical and electro-mechanical devices are well understood by those of skill in the art and are not described in detail herein.

The tissue marker may mark tissue with a variety of inks having a variety of colors, such as gentian violet, which is the tissue marking ink approved by the FDA. One or more of the ink colors utilized by tissue oximetry device 100 may indicate one or more oxygen saturation ranges. For example, the tissue marker can be configured to: (i) mark tissue with a first color of ink if the tissue's oxygen saturation is at or below a first threshold, (ii) mark the tissue with a second color of ink if the tissue's oxygen saturation is above the first threshold and at or below a second threshold, and (iii) mark the tissue with a third color of ink if the tissue's oxygen saturation is above the second threshold. The foregoing example describes the use of three colors of ink for marking tissue for visually identifying three ranges of oxygen saturation, however more or fewer colors can be utilized by the tissue marker for identifying more or fewer oxygen saturation ranges.

Control processor 200 may determine the oxygen saturation of a local tissue region based on an analysis of the reflection data as described above, and may control the tissue marker to mark the local tissue region with a select color of ink that identifies the range that the oxygen saturation is within. The tissue marker may include a variety of devices that provide marking material having one or more colors, such as ink reservoirs, pens, or the like. U.S. patent application Ser. 12,178,359, filed Jul. 23, 2008, of Heaton, titled "Oximeter with Marking Feature," which is incorporated by reference, describes a variety of devices that are configured for marking tissue with one or more colors of marking material.

A reservoir of the tissue marker can be connected to the dispenser, such as through tubing or channels, and may contain ink or other fluids (e.g., ink) dispensed through the dispenser. Ink can be moved from the reservoir to and through the dispenser and deposited on skin through pressure or low-frequency sound (such using a piezoelectric transducer). The reservoir can be contained within housing 105. For the disposable probe, the reservoir may not be refillable.

According to one alternative, the tissue marker, under control of processor 116, marks tissue for one or more oxygen saturation ranges, but does not mark the tissue for one or more other oxygen saturation regions. For example, the tissue marker can mark a local tissue region if the oxygen saturation of the local tissue region is at or below a threshold level, or alternatively does not mark the local tissue region if the oxygen saturation level is above the threshold level. Markings that are made on tissue according to the above method allow a user to relatively quickly identify tissue that can have a low chance of viability if the threshold level is relatively low. Alternatively, the tissue marker can mark a local tissue region if the oxygen saturation of the local tissue region is at or above a threshold level, and might not mark the local tissue region if the oxygen saturation level is below the threshold level. Marks made from this method allow a user to relatively quickly identify tissue that can have a relatively high chance of viability if the threshold level is relatively high.

Information for the foregoing described threshold levels (i.e., ranges) can be stored in memory device 205 and accessed by control processor 200 for use. The threshold levels can be stored in memory device 205 during manufacture of tissue oximetry device 100, or can be stored in the memory thereafter. For example, tissue oximetry device 100 can be configured to receive a user input for one or more user defined threshold levels and store information for these threshold levels in memory device 205. One or more input controllers 130 (or the like) can be configured to receive a user input for a user defined threshold level and for storing the user defined threshold level in memory device 205.

Figure 25:
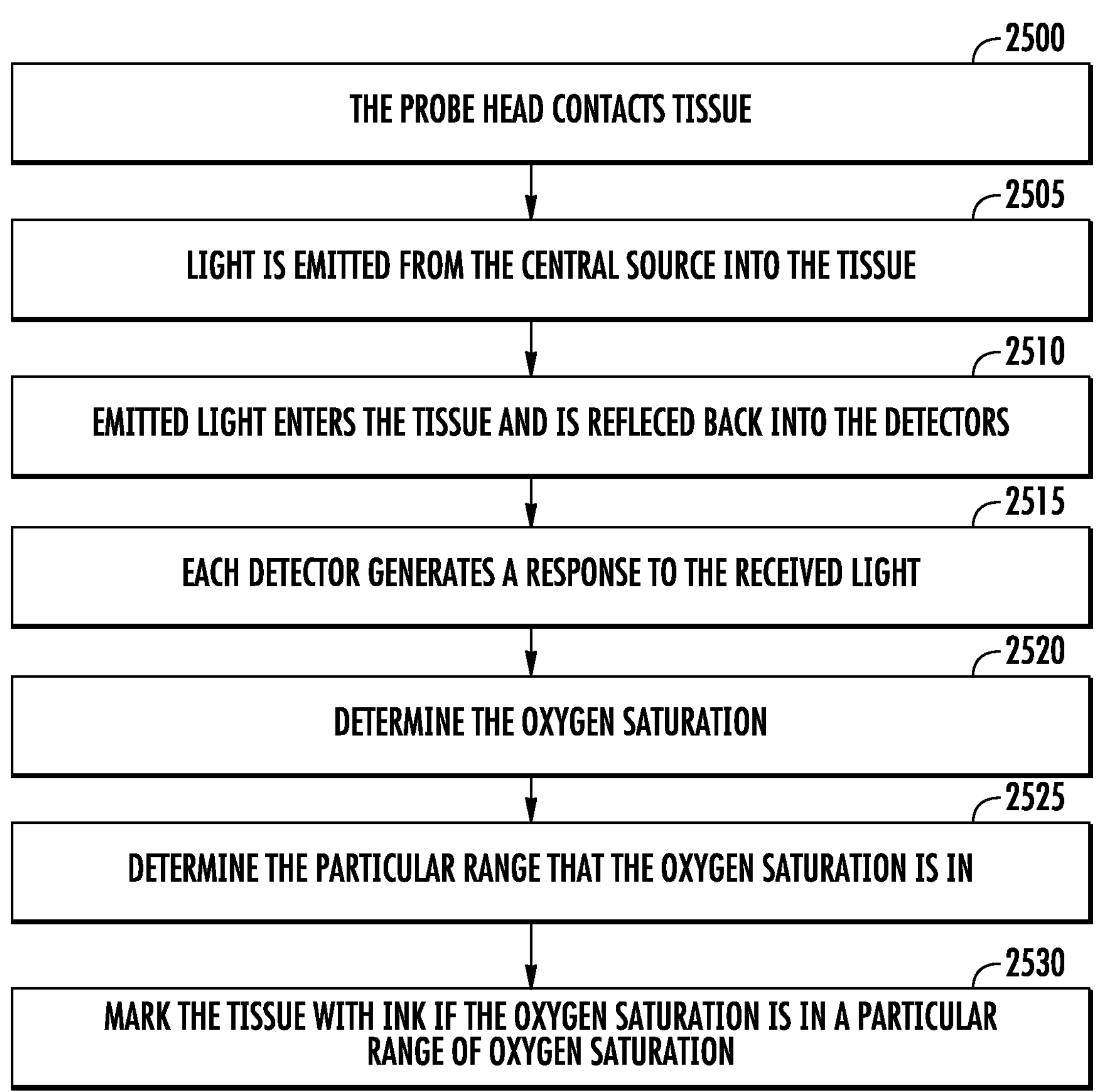
FIG. 25 is a high-level flow diagram of a method for marking tissue to indicate ranges of oxygen saturation of the tissue.

FIG. 25 is a high-level flow diagram of a method for marking tissue to indicate ranges of oxygen saturation of the tissue. The high-level flow diagram represents one example embodiment. Steps can be added to, removed from, or combined in the high-level flow diagram without deviating from the scope of the embodiment.

At 2500, probe tip 300 contacts the tissue. Light (e.g., near infrared light) is emitted from one or more of the light sources 150, step 2505, into the tissue and at least some of the light is reflected back by the tissue. Each light detector 170 receives a portion of the light reflected from the tissue, step 2510, and each light detector generates reflectance data (i.e., a response) for the portion of reflected light received, step 2515. At 2520, control processor 200 determines an oxygen saturation value for the tissue based on the reflectance data as described above.

At 2525, control processor 200 determines a range of oxygen saturation from a plurality of ranges of oxygen saturation in which the oxygen saturation lies. At 2530, control processor 200 controls the tissue marker to mark the tissue with ink based on a range in which the oxygen saturation is in. For example, the control processor can be configured to control the dispenser to mark the tissue with ink if the oxygen saturation is in a first range of oxygen saturation, but not mark the tissue if the oxygen saturation in a second range of oxygen saturation where the first range and second range are different, such as not overlapping ranges. While the foregoing example embodiment, discusses the utilization of two ranges of oxygen saturation by the tissue oximetry device, the tissue oximetry device may utilize more than two ranges of oxygen saturation for determining whether to mark the tissue with ink.

According to one embodiment, control processor 200 may control the dispenser to mark the tissue with a specific color of ink based on the range of oxygen saturation that the oxygen saturation is in. The particular color of ink allows a user to relatively quickly determine the ranges of oxygen saturation for the tissue without the need for re-probing the tissue or looking at a chart of the tissue that includes oxygen saturation values and matching the chart to the tissue.

Tissue oximetry device 100 can be configured to allow a user to manually control the tissue oximetry device to mark tissue, allow control processor 200 to control marking the tissue, or both. Tissue oximetry device 100 can be switched between the processor controlled method of marking tissue and the manually controlled method (e.g., by activating one of the input controllers 130) of marking tissue.

Laparoscopy

In one application of tissue oximetry probe 100, the tissue oximetry probe can be used by a physician for a laparoscope procedure to measure the oxygen saturation of tissues within a patient. In a laparoscope procedure, probe tip 300 of tissue oximetry probe 100 may be inserted into a relatively small incision (e.g., about 0.5 centimeters to about 2 centimeters) in a patient (e.g., in the patient's abdomen or pelvis) and pressed into contact with tissue for which an oxygen saturation measurement is to be made. In some use cases, probe head 250, tip portion 105*c* of housing 105, or both may also be inserted into the incision if the probe tip is to be moved further into the incision.

In this application, tissue oximetry probe 100 can be used in combination with a lighting system and a camera system that can be configured to be inserted in a different incision from the incision used for the tissue oximetry probe or the same incision. For example, probe tip 300 can be coupled to the lighting system and the camera system for insertion into a single incision. Probe tip 300 can be configured to be placed in or on a laparoscope tube that houses the lighting system and the camera system. In this embodiment, probe tip 300 may be coupled to tissue oximetry device 100 by a variety of devices. For example, probe tip 300 may be optically coupled by extended waveguides that are in-turn optically coupled to light sources, light detector, or both in housing 105. According to another example, probe tip 300 may be electrically coupled to acquisition module 115 by extended electrical wires, traces, or the like. The camera system might include a telescopic rod lens system that is connected to a video camera that is located outside of the patient's body, or might include a digital laparoscope where a miniature digital video camera is placed at the end of the digital laparoscope that is positioned in the patient during the laparoscope procedure.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. An oximeter device comprising:

a housing of the oximeter device, wherein the housing encloses a first printed circuit board and a battery, and the first printed circuit board comprises a processor;

a display, wherein the display is coupled to the printed circuit board and is visible from an exterior side of the housing, wherein the housing comprises:

a back surface of the housing which during use, is positioned between a thumb and forefinger of the hand, a top surface of the housing comprising the display, wherein the top surface and display are angled at a nonzero angle relative to the back surface, a bottom structure of the housing, wherein the bottom structure will retain a sensor head, and a tubular hand grip region, comprising the back surface, positioned between the top surface and the bottom structure, wherein the sensor head, retained by the bottom structure, comprises a relatively planar surface comprising sensor openings, the relatively planar surface is angled at a nonzero angle relative to the back surface, and the sensor head is accessible from the exterior side of the enclosure.

2. The device of claim 1 wherein the sensor head comprises at least a first sensor opening, a second sensor opening, a third sensor opening, and a fourth sensor opening, a first distance is between the first and second sensor openings, a second distance is between the first and third sensor openings, and a third distance is between the first sensor opening and the fourth sensor opening, and the first distance is different from the second distance, and the third distance is greater than the first distance and the second distance.

3. The device of claim 2 comprising:

a first light source for the first sensor opening, wherein the first sensor opening is coupled via an optical fiber to the first light source;

light detectors for the second and the third sensor openings, wherein the second and the third sensor openings are coupled via channels to the light detectors, and the optical fiber has a length that is longer than each of the channels; and a second light source for the fourth sensor opening, wherein the fourth sensor opening is coupled via an optical fiber to the second light source.

4. The device of claim 2 comprising:

a first light source for the first sensor opening, wherein the first sensor opening is coupled via an optical fiber to the first light source;

light detectors for the second and the third sensor openings, wherein the second and the third sensor openings are coupled via channels to the light detectors, and the optical fiber has a length that is longer than each of the channels; and a second light source for the first sensor opening, wherein the first sensor opening is coupled via an optical fiber to the second light source.

5. The device of claim 2 wherein the sensor head is configured to receive first data associated with the first and the second sensor openings, the sensor head is configured to receive second data associated with the first and the third sensor openings, and the processor is configured to perform spatially-resolved spectroscopy using the first and the second data to determine an oxygen saturation value.

6. The device of claim 2 wherein a fourth distance is between the second and fourth sensor openings, and a fifth distance is between the third and fourth sensor openings, the fourth distance is different from the first distance, and the fifth distance is different from the second distance.

7. The device of claim 5 wherein the sensor head is configured to receive third data associated with the second sensor and fourth sensor openings, the sensor head is configured to receive fourth data associated with the third sensor and fourth sensor openings, and the processor is configured to perform spatially-resolved spectroscopy and is further configured to also use the third and fourth data in determining the oxygen saturation value.

8. The device of claim 1 wherein the housing comprises a front surface, and the front surface is coupled between the top surface and the tubular hand grip region.

9. The device of claim 8 comprising:

a button, coupled to the front surface.

10. An oximeter device comprising:

a housing comprising:

a processor, contained within the housing;

a battery, contained within the housing, wherein the battery is coupled to the processor;

a display, coupled to the processor, wherein the display is visible from an exterior of the housing;

a back surface of the housing;

a top surface of the housing comprising the display, wherein the display is angled at a nonzero angle relative to the back surface; and a sensor module, coupled to the processor, wherein the sensor module comprises a probe face that is retained by a tip portion of the housing at a relatively fixed position with respect to the housing and that is placed against and faces tissue to be measured, and the probe face comprises:

a first source structure and a second source structure, formed on the probe face;

a first detector structure, formed on the probe face, wherein a first distance is from the first detector structure to the first source structure, a second distance is from the first detector structure to the second source structure, and the first distance is greater than the second distance;

a second detector structure, formed on the probe face, wherein a third distance is from the second detector structure to the first source structure, a fourth distance is from the second detector structure to the second source structure, and the fourth distance is greater than the third distance, and the first distance is the same as the fourth distance, and the second distance is the same as the third distance;

a third detector structure, formed on the probe face, wherein a fifth distance is from the third detector structure to the first source structure, a sixth distance is from the third detector structure to the second source structure, the fifth distance is different from the first distance and the second distance, and the sixth distance is different from the first distance and the second distance; and a fourth detector structure, formed on the probe face, wherein a seventh distance is from the fourth detector structure to the first source structure, an eighth distance is from the fourth detector structure to the second source structure, the seventh distance is different from the first, second, and fifth distances, and the eighth distance is different from the first, second, and sixth distances, and the first distance is greater than the second, third, fifth, sixth, seventh, and eighth distances, and the second distance is less than the fifth, sixth, seventh, and eighth distances.

11. The device of claim 10 wherein in operation, the processor collects first information from the first detector structure in response to radiation emitted from the first source structure.

12. The device of claim 11 wherein the first information is reflective of the tissue to be measured at a first depth below a surface of the tissue.

13. The device of claim 12 wherein in operation, the processor collects second information from the second detector structure in response to radiation emitted from the first source structure.

14. The device of claim 13 wherein the second information is reflective of the tissue to be measured at a second depth below the surface of the tissue.

15. The device of claim 14 wherein the second depth is less than the first depth.

16. The device of claim 15 wherein the tissue to be measured at the first depth is above a subcutaneous fat layer and muscle layer that are below the surface of the tissue.

17. The device of claim 10 wherein the sensor module comprises:

a first source diode and a second source diode;

a first optical fiber, coupled between the first source structure and the first source diode; and a second optical fiber, coupled between the second source structure and the second source diode.

18. The device of claim 10 wherein the first detector structure comprises a first photodetector positioned on the probe face, the second detector structure comprises a second photodetector positioned on the probe face, the third detector structure comprises a third photodetector positioned on the probe face, and the fourth detector structure comprises a fourth photodetector positioned on the probe face.

19. The device of claim 10 wherein the sensor module comprises:

a first photodetector, a second photodetector, a third photodetector, and a fourth photodetector;

a first waveguide, coupled between the first detector structure and the first photodetector;

a second waveguide, coupled between the second detector structure and the second photodetector;

a third waveguide, coupled between the third detector structure and the third photodetector; and a fourth waveguide, coupled between the fourth detector structure and the fourth photodetector.

20. The device of claim 10 wherein the sensor module comprises a temperature sensing unit configured to generate temperature information that represents the temperature of the first source structure.

21. The device of claim 20 wherein the processor is configured to adjust a duty cycle of an oscillating control signal supplied to the first source structure to adjust the luminosity generated by the first source structure based on the temperature information if the temperature of the first source structure changes.

22. The device of claim 19 wherein the first waveguide extends from the probe face of the sensor module through the first detector structure to the first photodetector.

23. The device of claim 22 wherein the second waveguide extends from the probe face of the sensor module through the second detector structure to the second photodetector.

24. The device of claim 23 wherein the third waveguide extends from the probe face of the sensor module through the third detector structure to the third photodetector.

25. The device of claim 24 wherein the fourth waveguide extends from the probe face of the sensor module through the fourth detector structure to the fourth photodetector.

26. The device of claim 2 comprising a first waveguide and a first light source for the first sensor opening, wherein the first waveguide extends from the planar surface of the sensor head through the first sensor opening to the first light source.

27. The device of claim 26 comprising a second waveguide and a first photodetector for the second sensor opening, wherein the second waveguide extends from the planar surface of the sensor head through the second sensor opening to the first photodetector.

28. The device of claim 2 comprising a first waveguide and a first photodetector for the first sensor opening, wherein the first waveguide extends from the planar surface of the sensor head through the first sensor opening to the first photodetector.

29. The device of claim 28 comprising a second waveguide and a first light source for the second sensor opening, wherein the second waveguide extends from the planar surface of the sensor head through the second sensor opening to the first light source.

30. An oximeter device comprising:

a housing of the oximeter device, wherein the housing encloses a first printed circuit board and a battery, and the first printed circuit board comprises a processor;

a display, wherein the display is coupled to the printed circuit board and is visible from an exterior side of the housing, wherein the housing comprises:

a back surface of the housing which during use, is positioned between a thumb and forefinger of the hand, a top surface of the housing comprising the display, wherein the top surface is angled at a nonzero angle relative to the back surface, a bottom structure of the housing, wherein the bottom structure will retain a sensor head, and a tubular hand grip region, comprising the back surface, positioned between the top surface and the bottom structure, wherein the sensor head, retained by the bottom structure, comprises at least a first sensor opening and a relatively planar surface comprising sensor openings, the relatively planar surface is angled at a nonzero angle relative to the back surface, and the sensor head is accessible from the exterior side of the enclosure; and a first waveguide and a first photodetector for the first sensor opening, wherein the first waveguide extends from the planar surface of the sensor head through the first sensor opening to the first photodetector.

31. The device of claim 30 comprising a second waveguide and a second photodetector for a second sensor opening, wherein the second waveguide extends from the planar surface of the sensor head through the second sensor opening to the second photodetector.

* * * * *